(12) United States Patent
Wang et al.

(10) Patent No.: US 11,944,624 B2
(45) Date of Patent: Apr. 2, 2024

(54) PEPTIDE AND SMALL MOLECULE AGONISTS OF EPHA AND THEIR USES

(71) Applicant: CASE WESTERN RESERVE UNIVERSITY, Cleveland, OH (US)

(72) Inventors: Bingcheng Wang, Solon, OH (US); Bin Su, Cleveland, OH (US); Aaron Petty, Parma, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/628,990

(22) PCT Filed: Jul. 3, 2018

(86) PCT No.: PCT/US2018/040715
§ 371 (c)(1),
(2) Date: Jan. 6, 2020

(87) PCT Pub. No.: WO2019/010180
PCT Pub. Date: Jan. 10, 2019

(65) Prior Publication Data
US 2020/0222405 A1    Jul. 16, 2020

Related U.S. Application Data

(60) Provisional application No. 62/529,399, filed on Jul. 6, 2017.

(51) Int. Cl.
| | | |
|---|---|---|
| *C07D 239/95* | (2006.01) | |
| *A61K 31/517* | (2006.01) | |
| *C07D 403/04* | (2006.01) | |
| *A61K 45/06* | (2006.01) | |

(52) U.S. Cl.
CPC .......... *A61K 31/517* (2013.01); *C07D 403/04* (2013.01); *A61K 45/06* (2013.01)

(58) Field of Classification Search
CPC ................. C07D 239/95; C07D 403/04; A61K 31/517
See application file for complete search history.

(56) References Cited

U.S. PATENT DOCUMENTS

| | | | | |
|---|---|---|---|---|
| 3,511,836 A | * | 5/1970 | Hess | C07D 403/04 544/402 |
| 4,001,237 A | * | 1/1977 | Partyka | C07D 239/95 544/286 |
| 4,060,615 A | * | 11/1977 | Matier | C07D 405/12 544/291 |
| 4,189,484 A | * | 2/1980 | Mizogami | C07D 239/95 514/218 |
| 4,426,382 A | * | 1/1984 | Sato | C07D 239/95 514/218 |
| 5,110,927 A | * | 5/1992 | Pitha | C07D 409/12 544/291 |
| 2009/0048265 A1 | | 2/2009 | Chen et al. | |
| 2017/0165322 A1 | | 6/2017 | Wang | |

FOREIGN PATENT DOCUMENTS

| | | | |
|---|---|---|---|
| JP | 56103180 | * | 8/1981 |
| WO | 2006002088 A2 | | 1/2006 |
| WO | 2009008901 A2 | | 1/2009 |

OTHER PUBLICATIONS

Schriabine et al. (Experientia (1968), 24(11), 1150-1). Abstarct.*
Cohen (Journal of Clinical Pharmacology and the Journal of New Drugs (1970), 10(6), 408-17). Abstarct.*
Bottini et al. (Chemical Biology & Drug Design (2015), 86(4), 663-673).*
Bolognesi et al. (Journal of Medicinal Chemistry (2001), 44(3), 362-371). Abstract.*
Giardina, D et al., "Doxazosin-Related alpha1-Adrenoceptor Antagonists With Prostate Antitumor Activity", Journal of Medicinal Chemistry 52, pp. 4951-4954, 2009.
Kenny, BA et al., "Evaluation of the pharmacological selectivity profile of alpha1 adrenoceptor antagonists at prostatic alpha1 adrenoceptors: binding, functional and in vivo studies", British Journal of Pharmacology 118, pp. 871-878, 1996.
Martin, DJ et al., "Comparative Alpha-1 Adrenoceptor Subtype Selectivity and Functional Uroselectivity of Alpha-1 Adrenoceptor Antagonists", The Journal of Pharmacology and Experimental Therapeutics 282(1), pp. 228-235, 1997.
Applicant: Case Western Reserve University; "Peptide and Small Molecule Agonists of EPHA and Their Uses"; European Patent Application No. 18827735; Mar. 4, 2021; 13 pgs.
Bottini Angel et al: "Targeting Influenza 2-4,9-14 A Virus RNA Promoter", Chemical Biology & Drug Design, vol. 86, No. 4, 2015, pp. 663-673, XP055779152.
Petty Aaron et al: "Design and synthesis of small molecule agonists of EphA2 receptor", European Journal of Medicinal Chemistry, vol. 143, Oct. 10, 2017, pp. 1261-1276, XP085305966.
Applicant: Case Western Reserve University; "Peptide and Small Molecule Agonists of EPHA and Their Uses"; European Patent Application No. 18827735; Extended European Search Report; 12 pgs.

* cited by examiner

*Primary Examiner* — Bruck Kifle
(74) *Attorney, Agent, or Firm* — TAROLLI, SUNDHEIM, COVELL & TUMMINO, LLP

(57) ABSTRACT

A method of treating cancer in a subject includes administering to the subject a therapeutically effective amount of a compound, the small molecule having a general formula: A-L-X—Z (I).

6 Claims, 45 Drawing Sheets

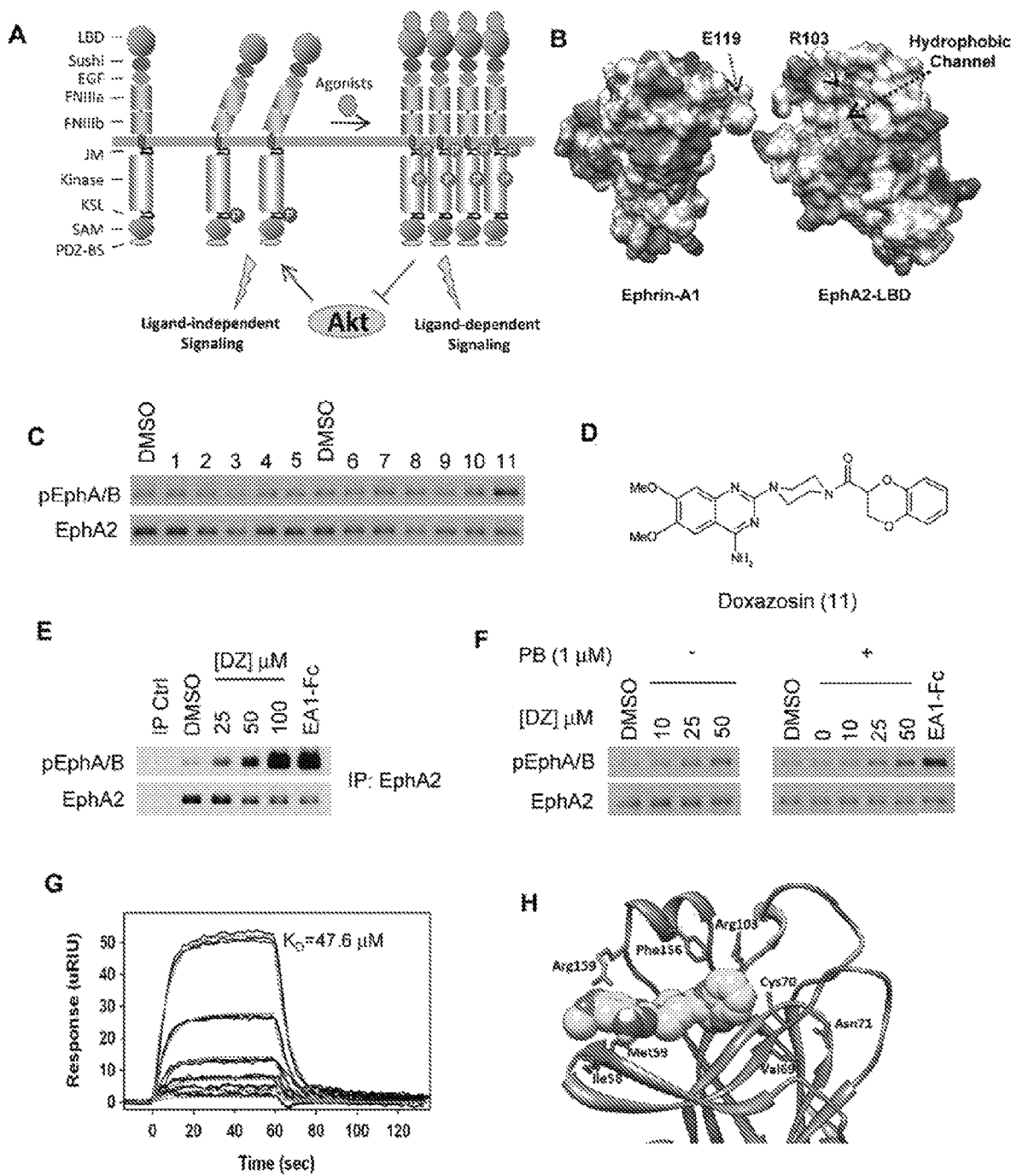
Figs. 1A-H

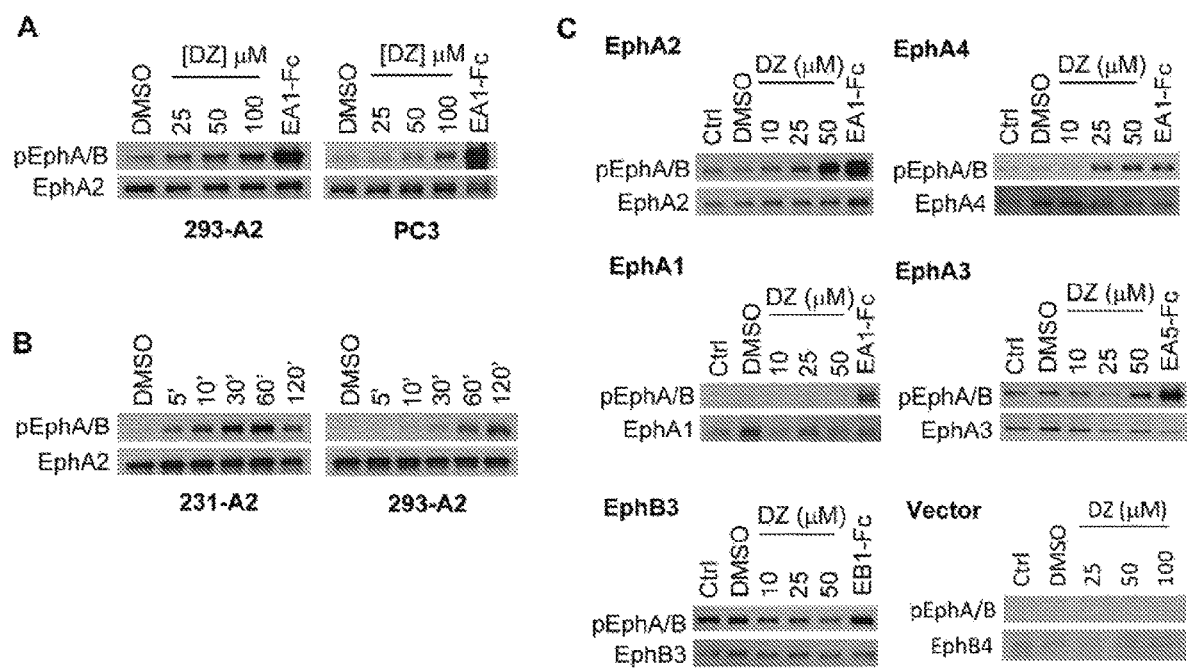
Figs. 2A-C

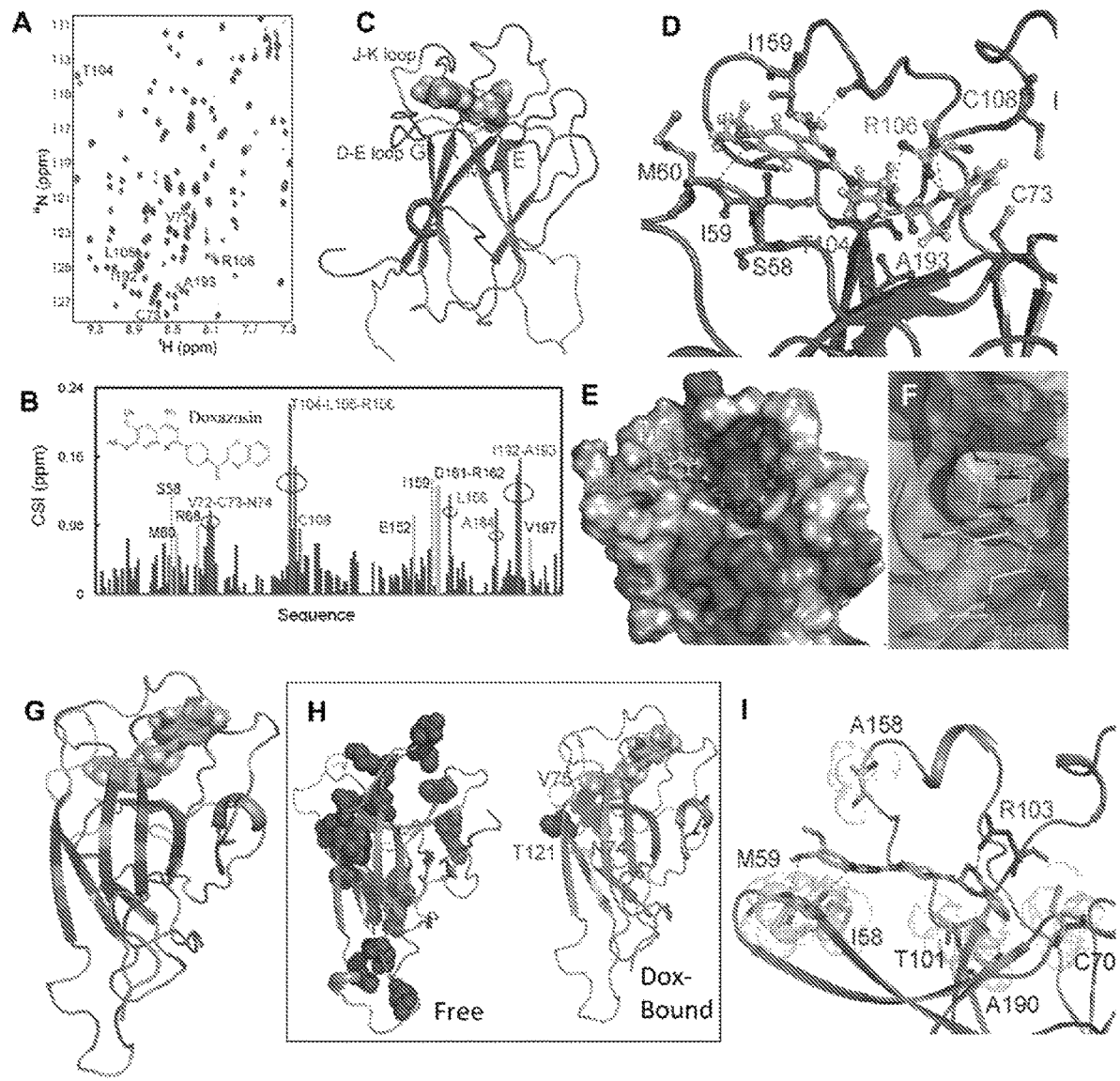
Figs. 3A-I

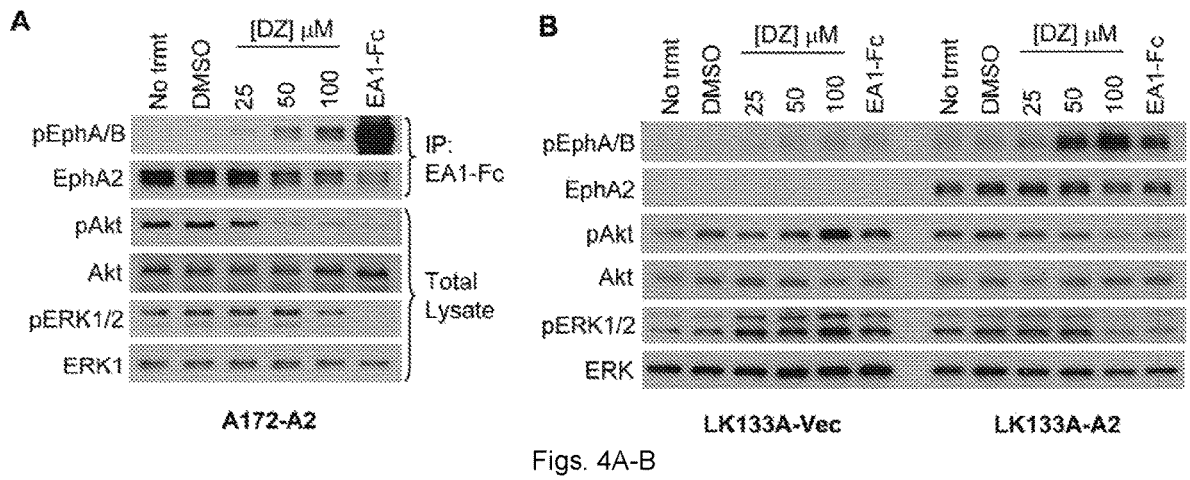
Figs. 4A-B
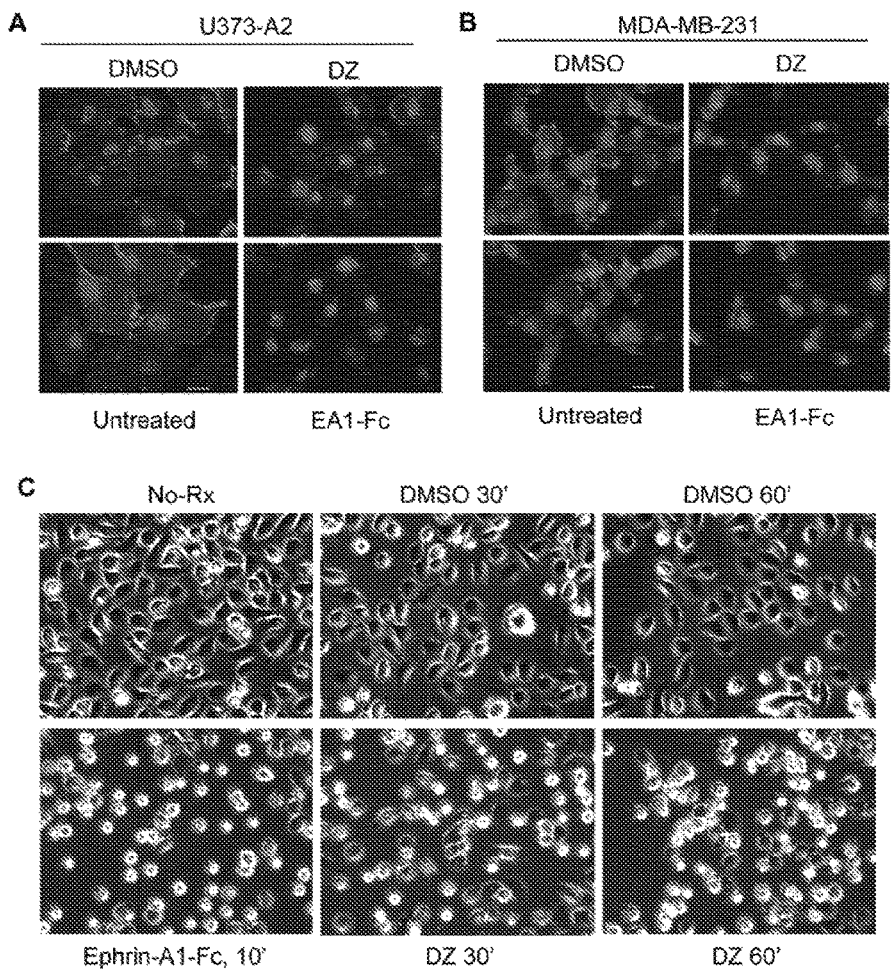
Figs. 5A-C

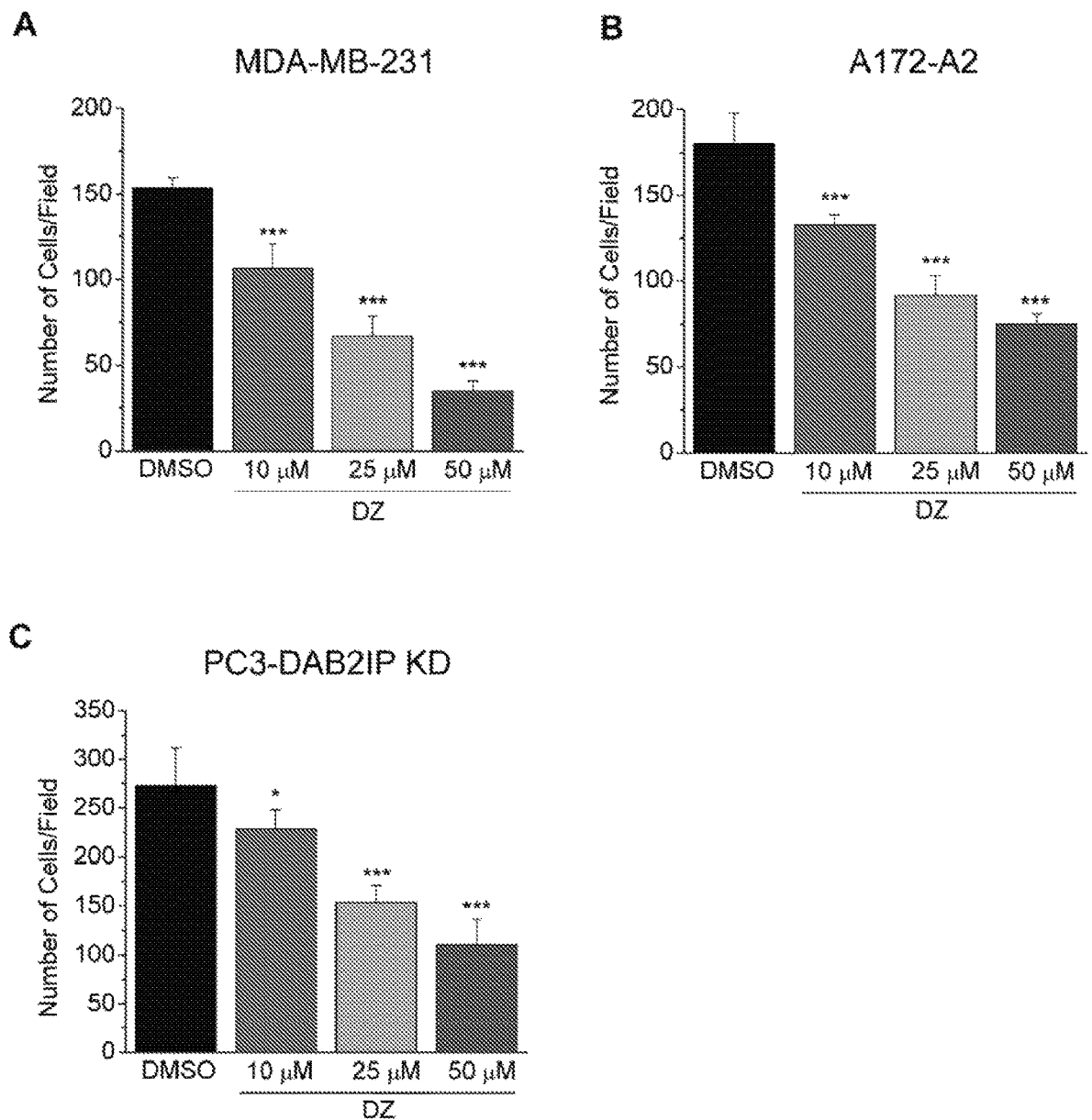
Figs. 6A-C

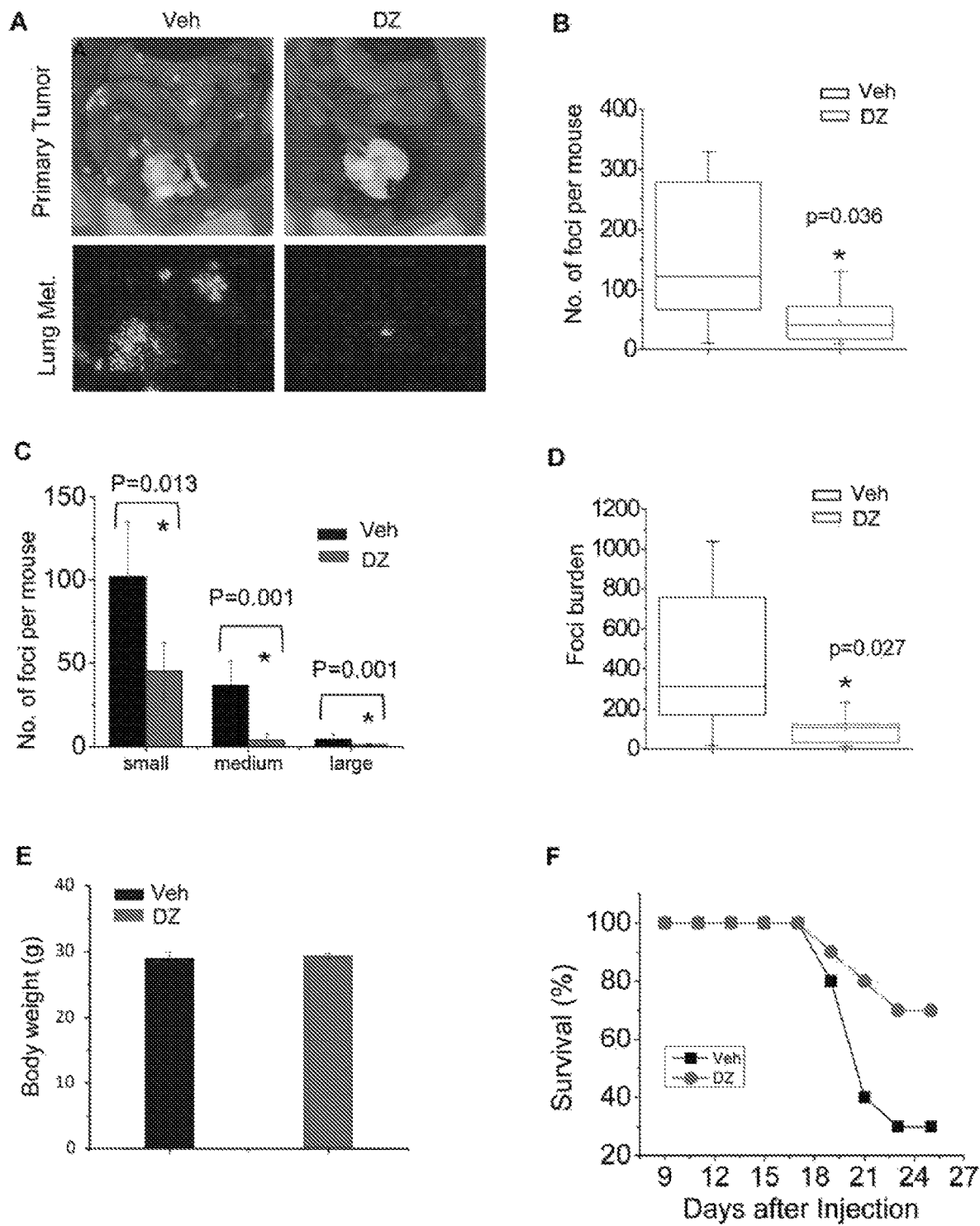
Figs. 7A-F

— Began treatment on day 13 post-implantation
— Treated with 50 mg/kg DZ
— Vehicle = 10% Cremophor/5% DMSO/PBS

GFP-positive primary tumors
Vehicle
DZ
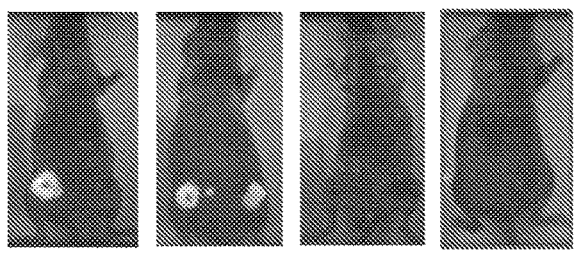
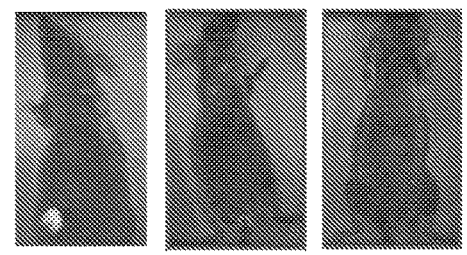
Red box = mice without primary tumor at sacrifice
-Mice treated for 24 and 26 days
Fig. 9

EphA2 activation in primary tumor lysates of metastasis-free mice

| Vehicle | DZ |
|---|---|
| 1/10 | 3/9 |

Fig. 11 # of mice with lung metastasis

| Severity of lung metastasis | None | + | ++ |
|---|---|---|---|
| Vehicle | 1 | 4 | 5 |
| DZ | 3 | 4 | 2 |

+ = < 20 cells, single cells

++ = > 20 cells, 1-3 cell clusters

Fig. 12

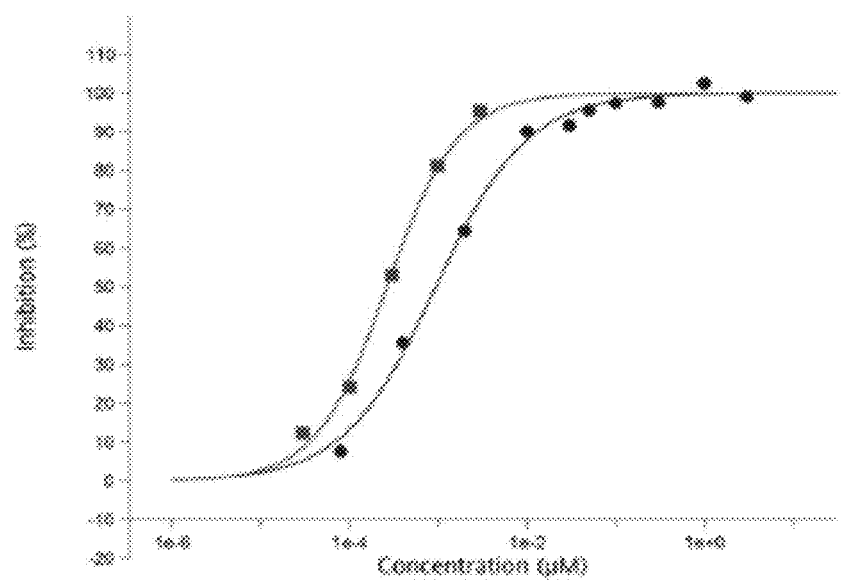
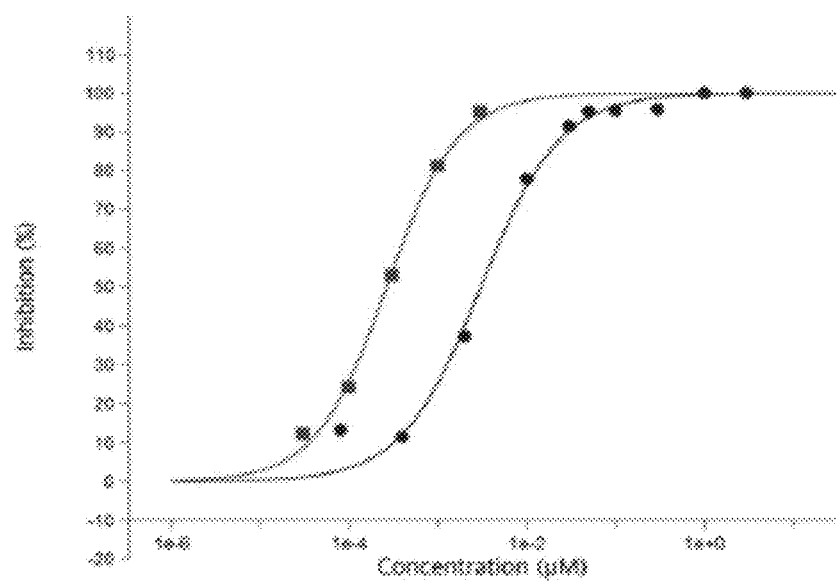
Fig. 16

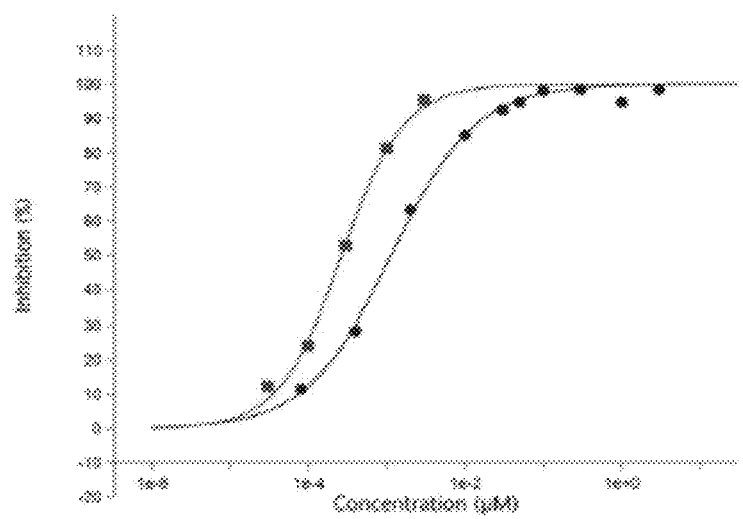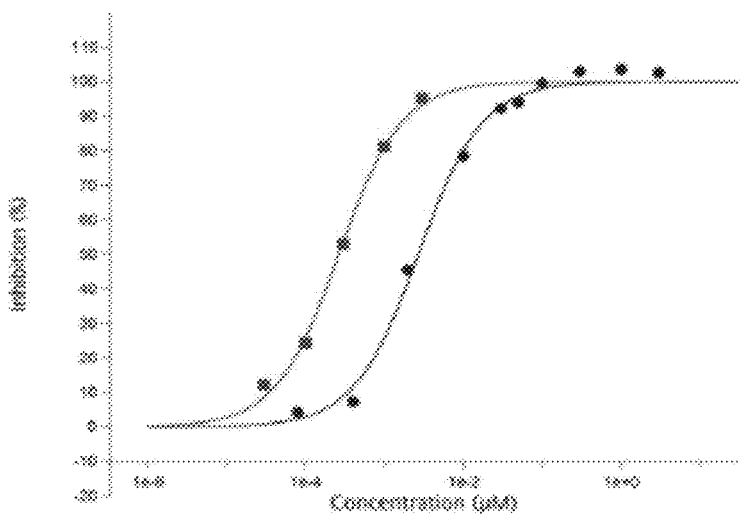
Fig. 16 (Continued)

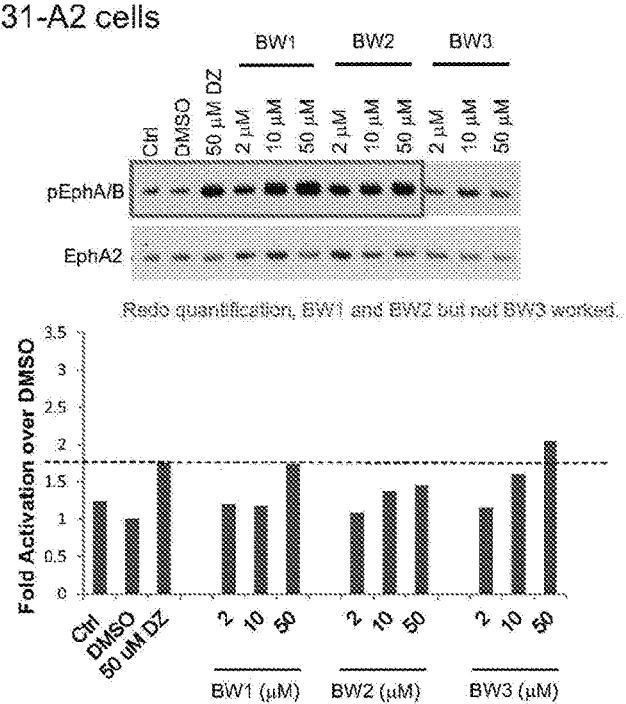
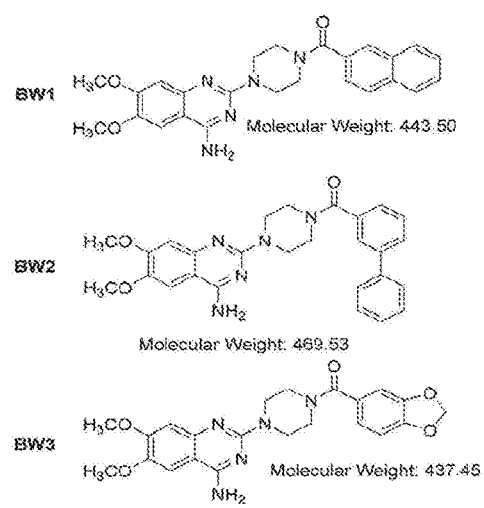
Fig. 17

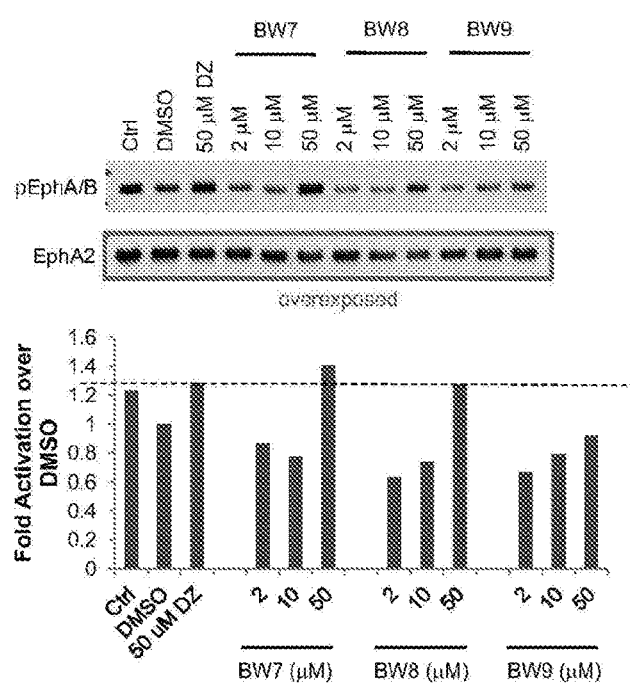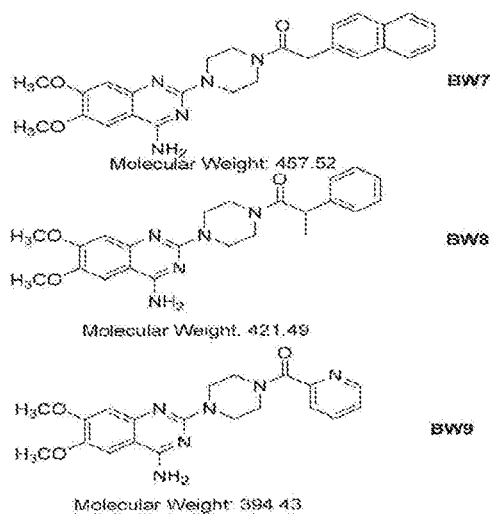
Fig. 18

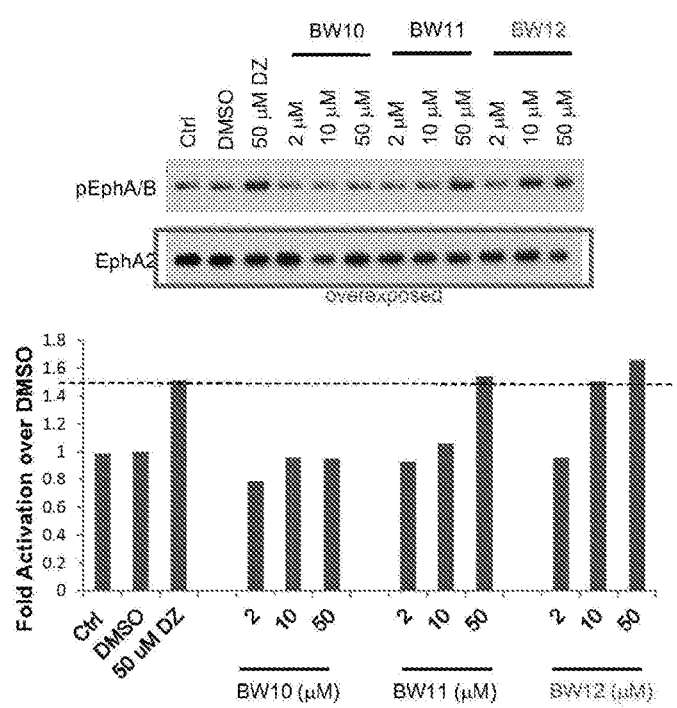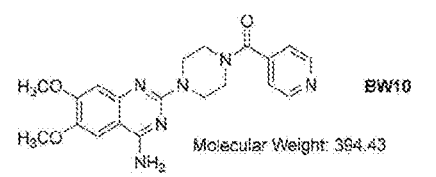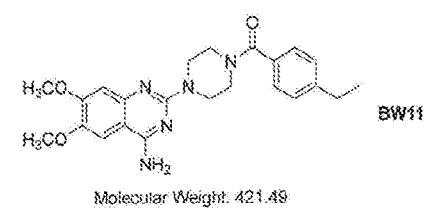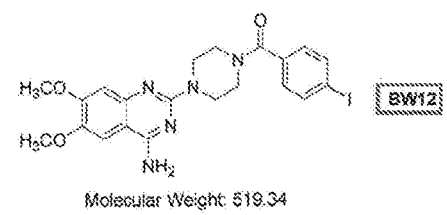
Fig. 20

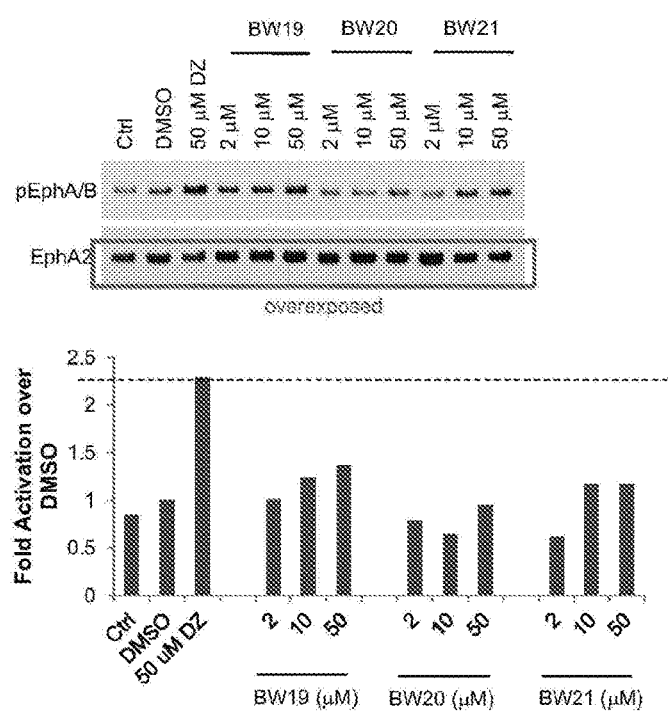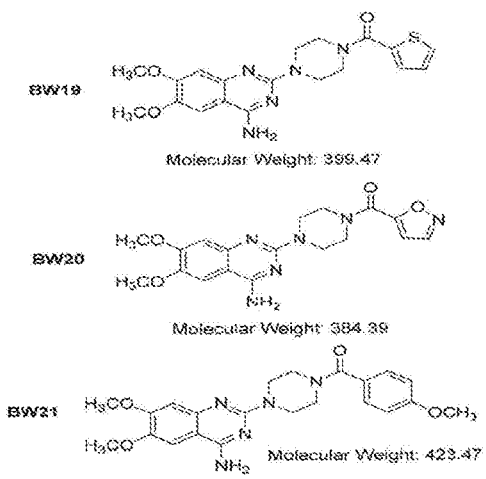
Fig. 23

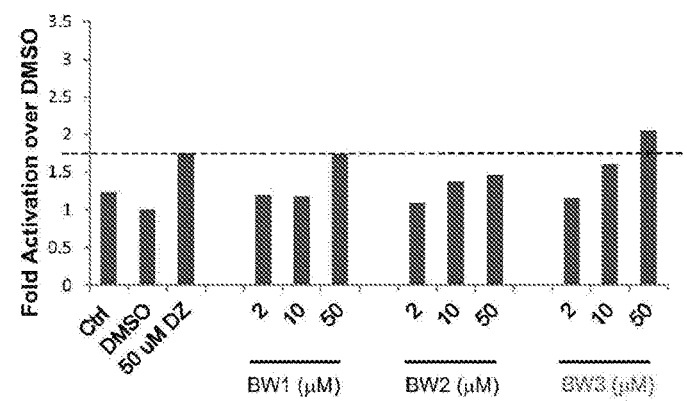
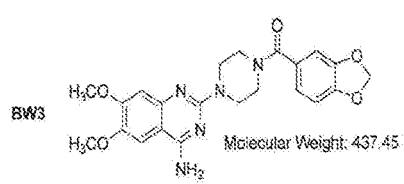
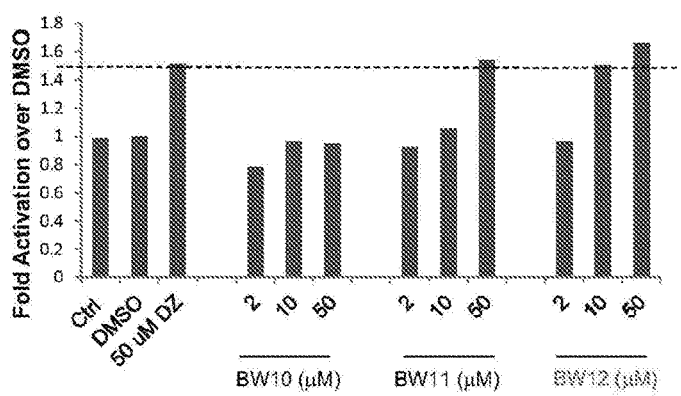
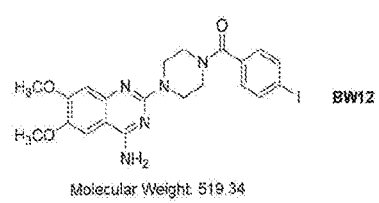
Fig. 25

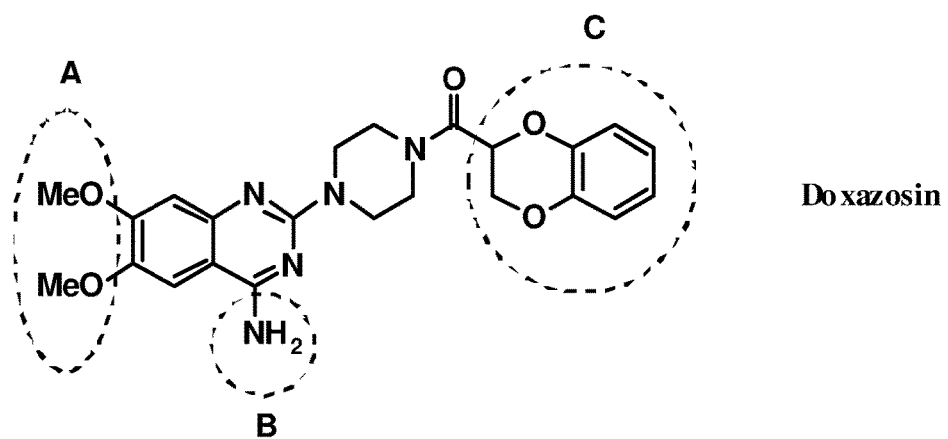 Doxazosin
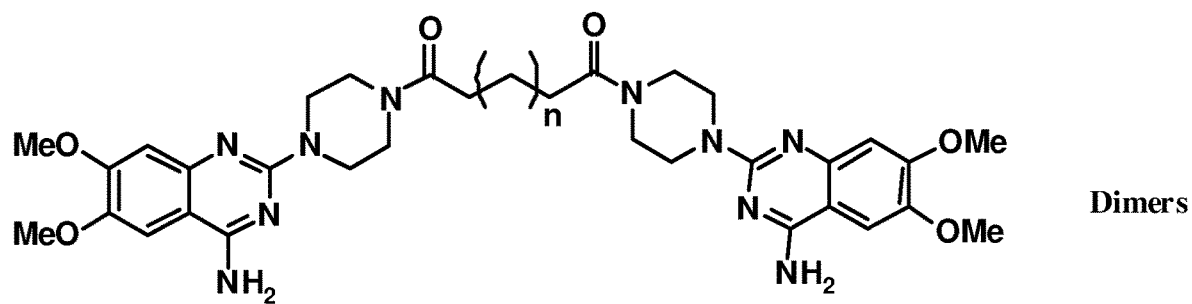 Dimers
Fig. 26

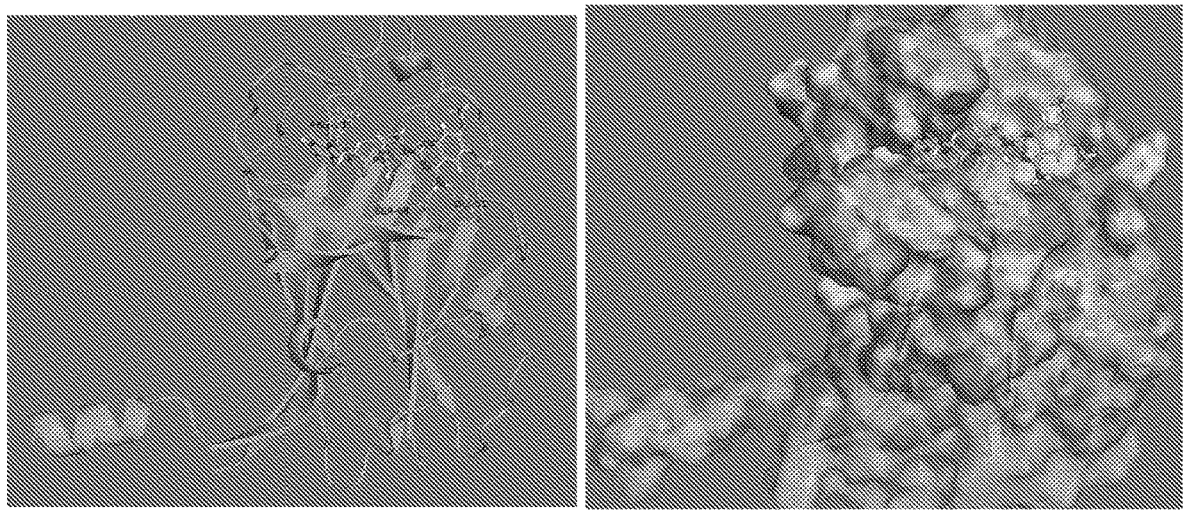
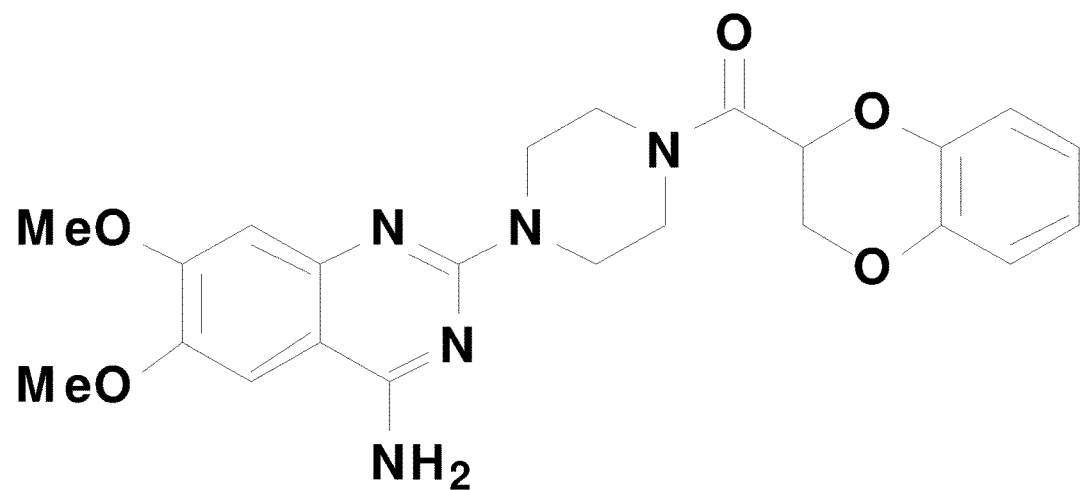
Doxazosin
Fig. 30

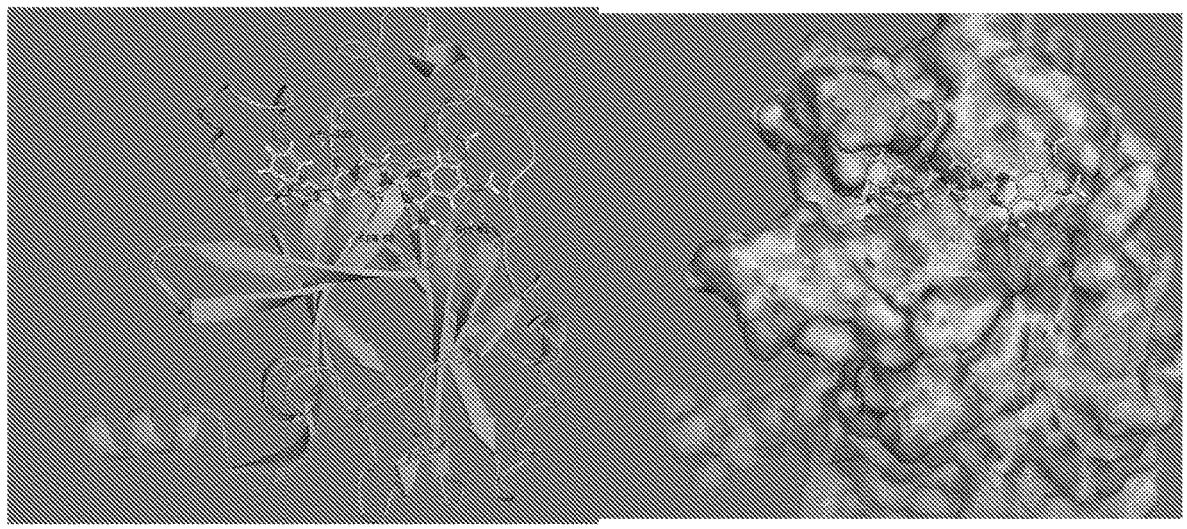
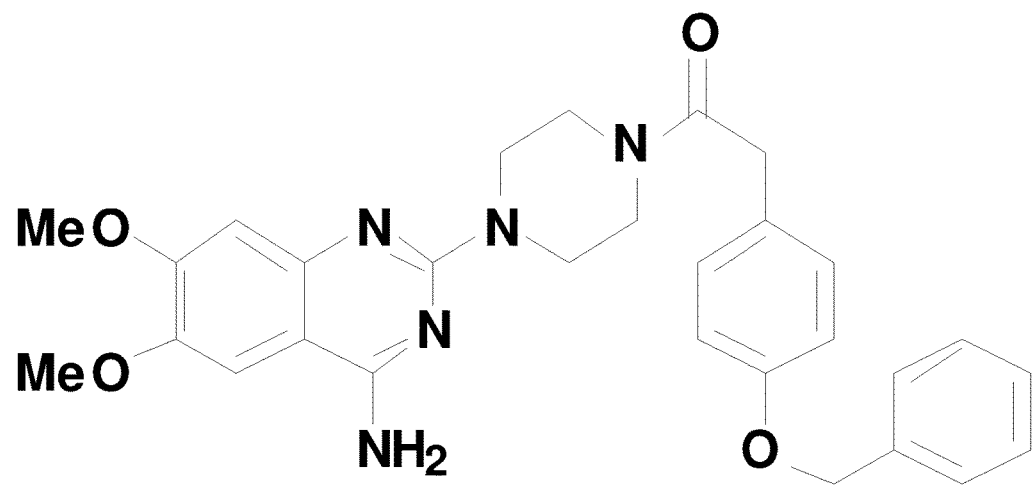
Compound 24
Fig. 30 (Continued)

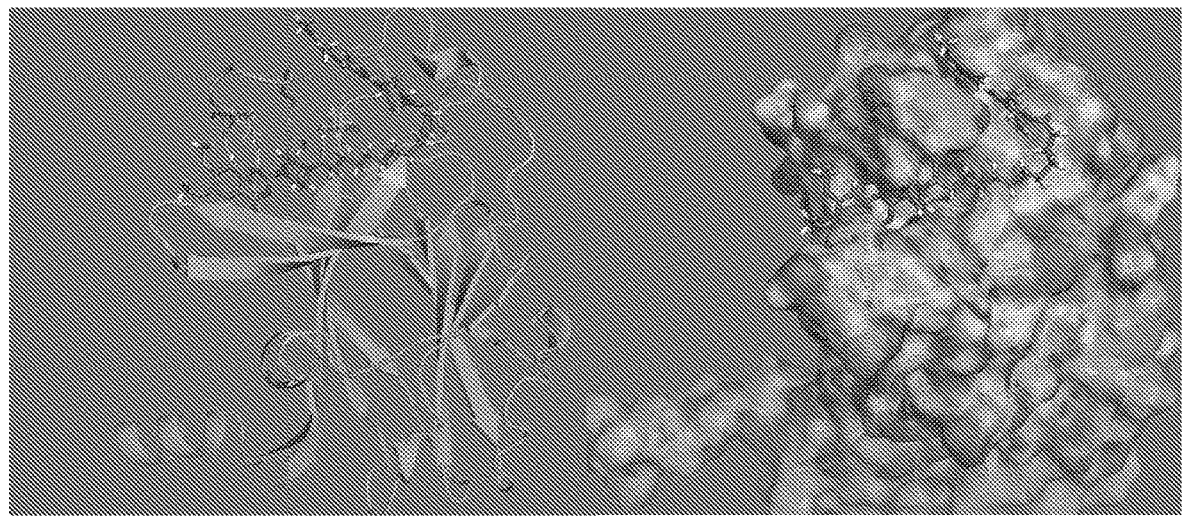
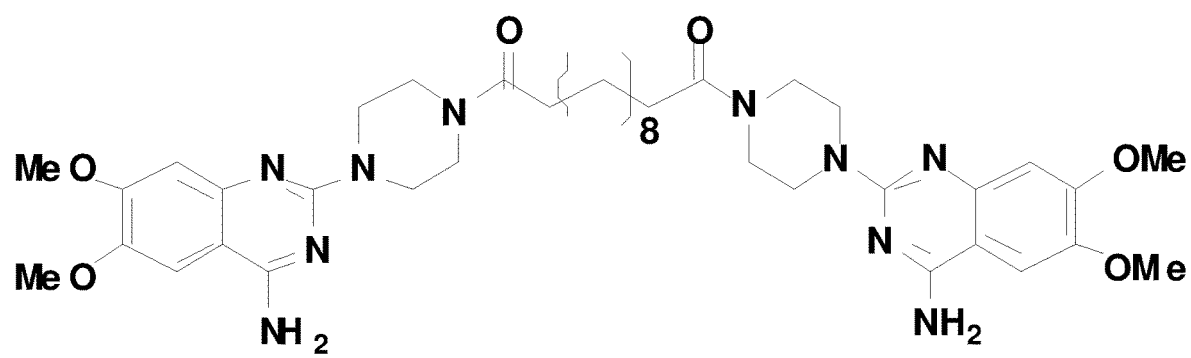
Compound 27
Fig. 30 (Continued)

PEPTIDE AND SMALL MOLECULE AGONISTS OF EPHA AND THEIR USES

RELATED APPLICATION

This application claims priority from U.S. Provisional Application No. 62/529,399, filed Jul. 6, 2017, the subject matter of which is incorporated herein by reference in its entirety.

GOVERNMENT FUNDING

This invention was made with government support under CA092259 and CA096533 awarded by the National Institutes of Health; and DAMD17-99-1-9019 awarded by the Department of Defense. The government has certain rights in the invention.

BACKGROUND

As a member of the erythropoietin-producing hepatocellular (Eph) subfamily of receptor tyrosine kinases (RTKs), EphA2 was originally called epithelial cell kinase, or Eck, due to its widespread expression in epithelial cells in vitro and in vivo. Subsequent studies revealed that EphA2 was overexpressed in human cancers, and that overexpression was correlated with malignant progression and poor prognosis.

A large number of studies have demonstrated that EphA2 overexpression and activation promote tumorigenesis, suggesting a potential role as an oncogene. Overexpression of EphA2 in breast epithelial cells induced morphological transformation, while in prostate cancer and glioma cell lines, elevated EphA2 expression caused increased chemotactic cell migration and invasion. Contrasting the pro-oncogenic roles, many studies have shown that EphA2 activation by its ligand, ephrin-A1, regulates cellular behaviors in a manner more consistent with it being a tumor suppressor, including induction of apoptosis, inhibition of cell proliferation, and suppression of cell migration.

It has been further revealed that the EphA2 receptor has diametrically opposite roles in tumorigenesis. For example, upon ligand stimulation, EphA2 inhibits cell migration in keeping with the well-established repulsive roles of Eph receptors in regulating cell motility. In direct contrast, in the absence of ligand, EphA2 promotes cell migration, which is correlated with its expression level. EphA2 overexpression is often accompanied by loss of expression or mislocalization of ephrin-A1 in breast cancer, glioma and skin tumors. The reduced ephrin-A expression coupled with increased EphA2 expression and frequent Akt activation provide a permissive environment to promote ligand-independent pro-invasive Akt-EphA2 crosstalk, which may be in part responsible for EphA2 overexpression during tumor progression and the correlation of EphA2 expression and unfavorable prognosis. Other tumor suppressor functions of EphA2 are also activated upon ligand-induced EphA2 activation, including inactivation of the Ras/ERK pathway. The ligand dependent signaling culminates in the inhibition of cell migration and proliferation, although the specific responses are modulated by cellular context, such as Ras activation status in a given tumor cell type.

SUMMARY

Embodiments described herein relate to compositions and methods for treating cancer in a subject. The methods include administering to the subject a therapeutically effective amount of a compound. The compound can include a small molecule agonist of EphA2 receptor protein. In some embodiments, the compound can have a general formula:

$$\text{A-L-X—Z} \tag{I},$$

wherein A is a substituted or unsubstituted aryl or heteroaryl;

L is

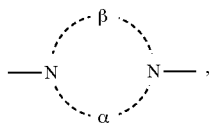

wherein α and β can each individually represent $(CH_2)_m$ (m is an integer from 2 to 4) and β is optionally present;

X is C=O or $SO_2$; and

Z is $-Y-(R^1)_n$, wherein Y is a substituted or unsubstituted $C_1$-$C_{24}$ alkyl, $C_2$-$C_{24}$ alkenyl, $C_2$-$C_{24}$ alkynyl, aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl), wherein Z is not a 1,4 benzodioxin when A is an 4-Amino-6,7-dimethoxy-2-quinazolinyl, $R^1$ is optionally present and if present is a structurally similar monomer of A-L-X and is linked to X via Y, and n is an integer from 0-10, thereby forming a dimer, trimer, or dendrimer molecule of A-L-X monomers, and pharmaceutically acceptable salts thereof.

In some embodiments, the compound can have the formula (II):

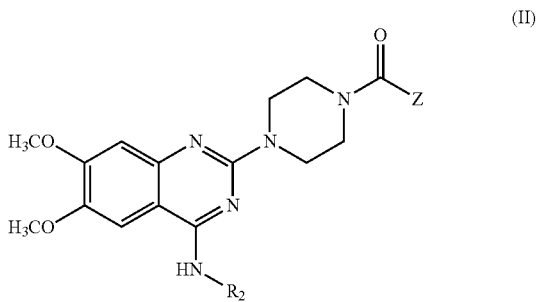

wherein Z is $-Y-(R^1)_n$, $R^2$ is selected from H, an alkoxy (e.g., acetyl) or a $C_{1-6}$alkyl (e.g., methyl) group, Y is a substituted or unsubstituted $C_1$-$C_{24}$ alkyl, $C_2$-$C_{24}$ alkenyl, $C_2$-$C_{24}$ alkynyl, aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl), $R^1$ is optionally present and if present is a structurally similar monomer of formula (III):

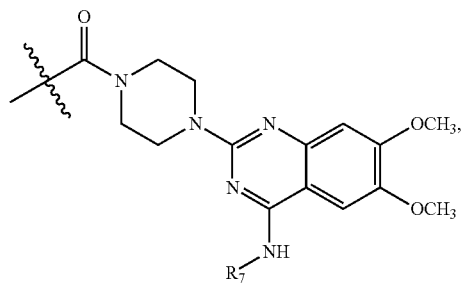

(III)

$R^7$ is selected from H, an alkoxy (e.g., acetyl) or a $C_{1-6}$ alkyl (e.g., methyl) group, and n is an integer from 0-10, and pharmaceutically acceptable salts thereof.

Examples of compounds include the following:

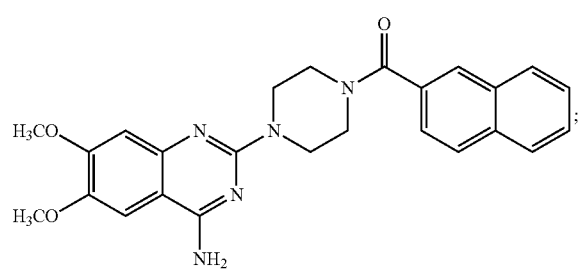

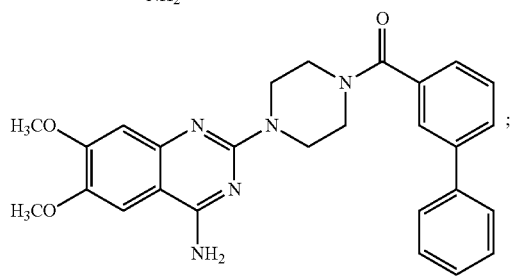

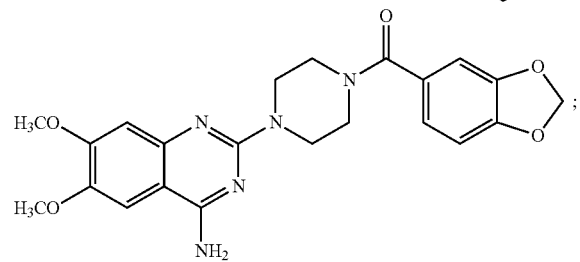

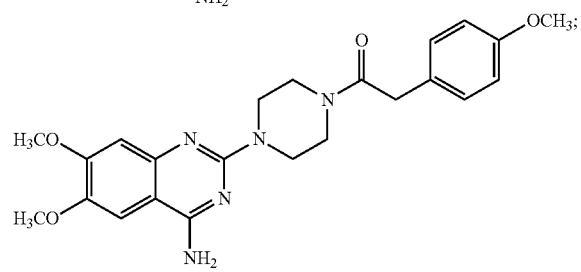

-continued

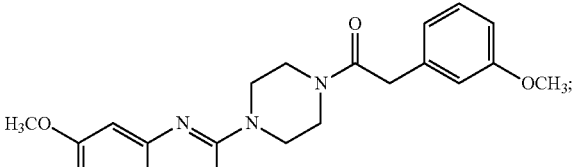

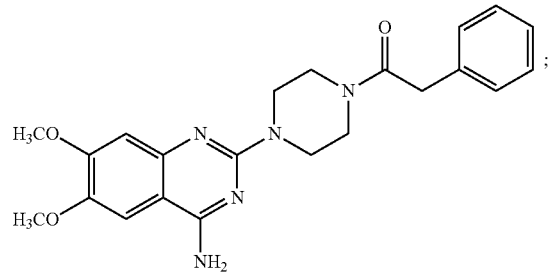

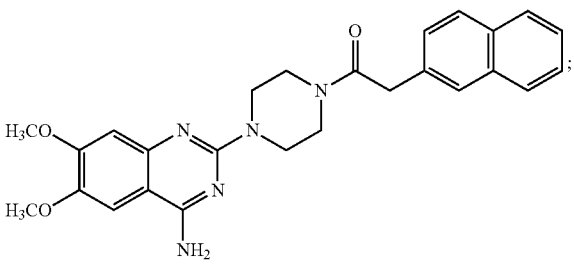

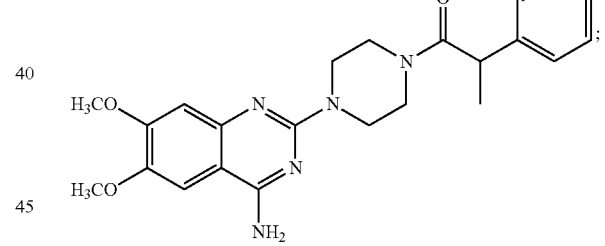

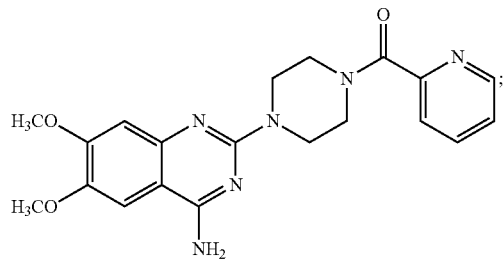

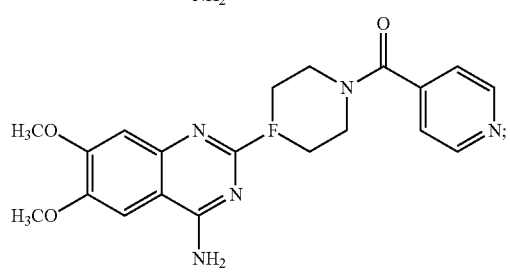

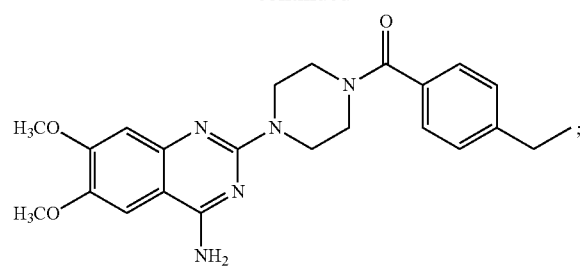
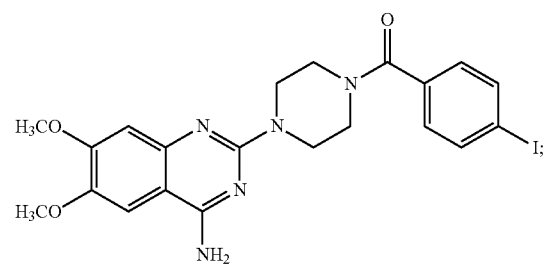
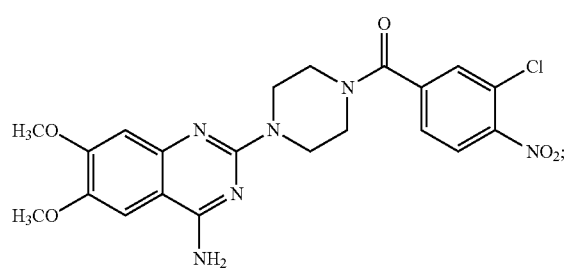
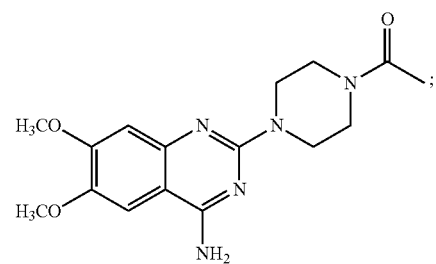
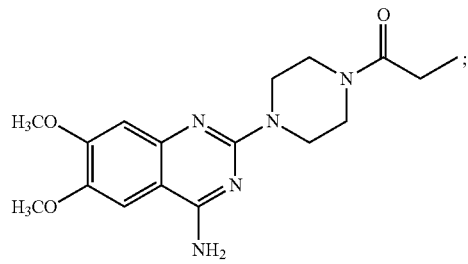
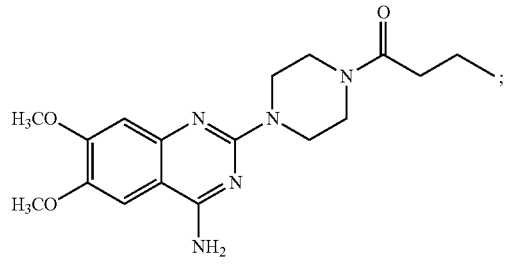
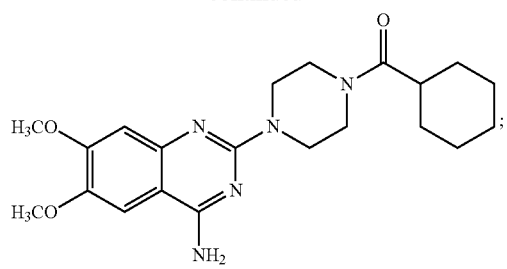
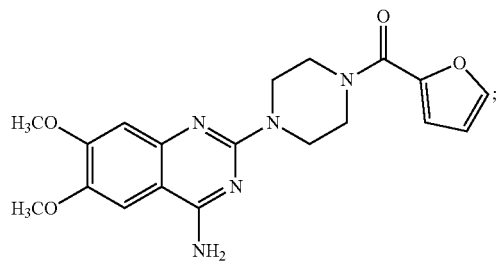
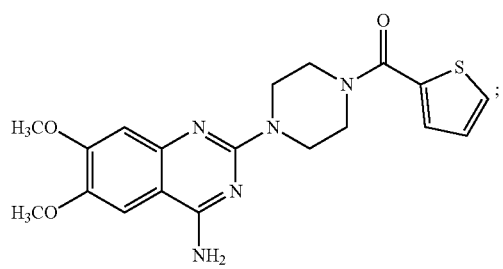
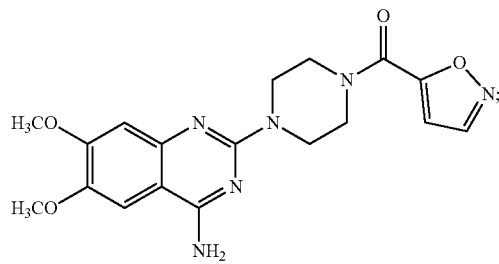
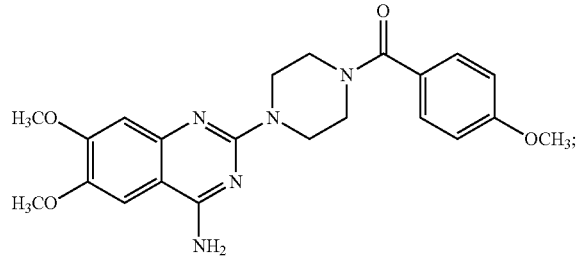
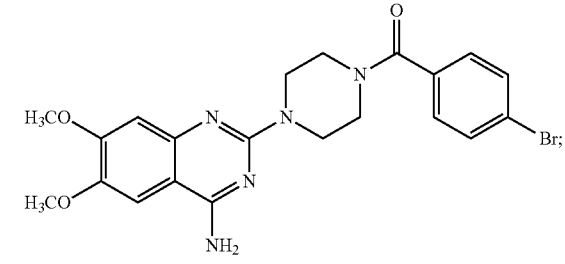

-continued

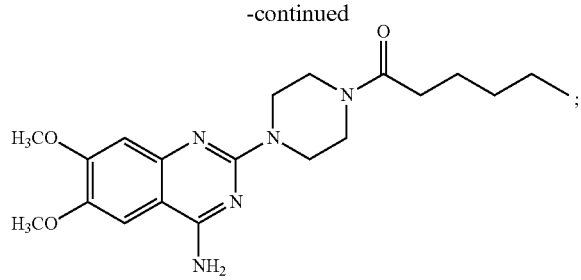

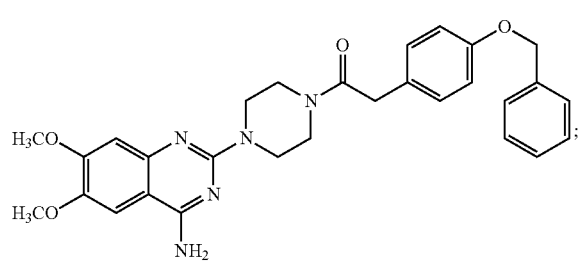

and pharmaceutically acceptable salts thereof.

In particular embodiments, the compound is not doxazosin.

In some embodiments, the compound has a lower α-adrenoreceptor binding affinity than doxazosin.

In some embodiments, the therapeutically effective amount of a compound is the amount effective to activate and internalize EphA2 receptors in cancer cells of the subject. In some embodiments, the therapeutically effective amount of a compound is the amount effective to inhibit tumor growth associated with EphA2 tumorgenesis in the subject.

In some embodiments, the cancer can be characterized by the overexpression of EphA2 in cancer cells of the subject. In some embodiments, the cancer can be selected from breast cancer, prostate cancer, carcinoma, and glioma.

Another aspect relates to a pharmaceutical composition including a compound having the formula (II):

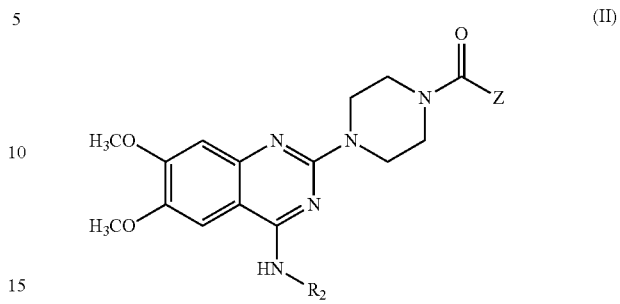

wherein Z is —Y—($R^1$)$_n$, $R^2$ is selected from H, an alkoxy or a $C_{1-6}$ alkyl group, Y is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl), wherein Z is not a 1,4 benzodioxin when A is an 4-Amino-6,7-dimethoxy-2-quinazolinyl, $R^1$ is optionally present and if present is a structurally similar monomer of formula (III):

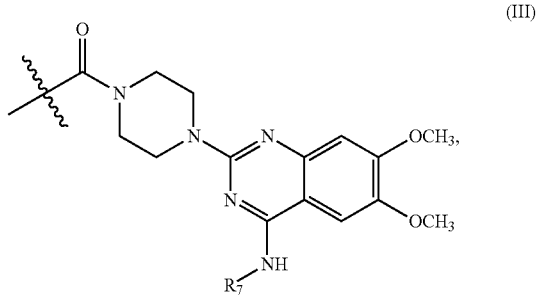

$R^7$ is selected from H, an alkoxy (e.g., acetyl) or a $C_{1-6}$ alkyl (e.g., methyl) group, and n is an integer from 0-10, and pharmaceutically acceptable salts thereof; and a pharmaceutically acceptable carrier.

In some embodiments, the compound is selected from the group consisting of:

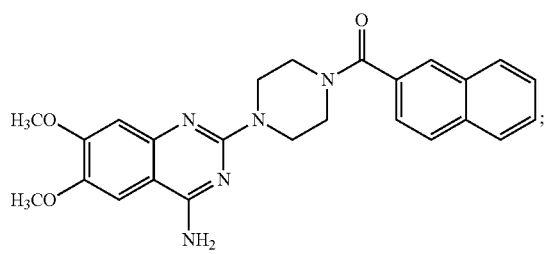

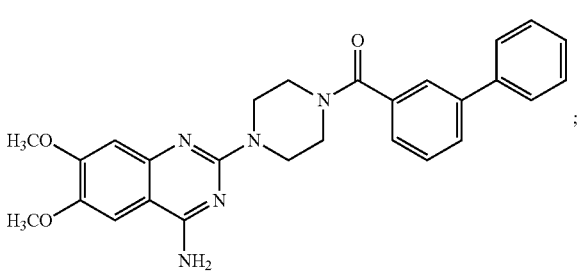

-continued
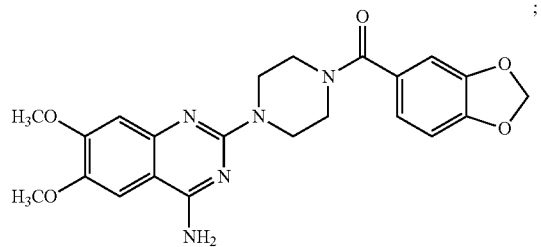
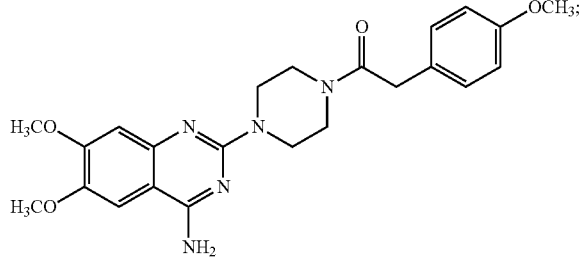
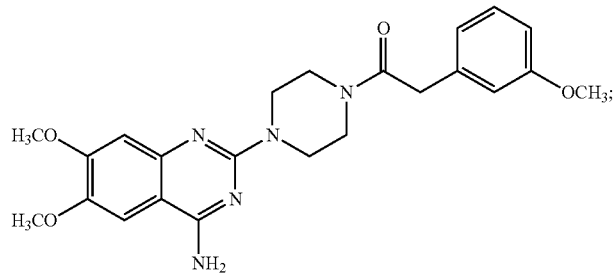
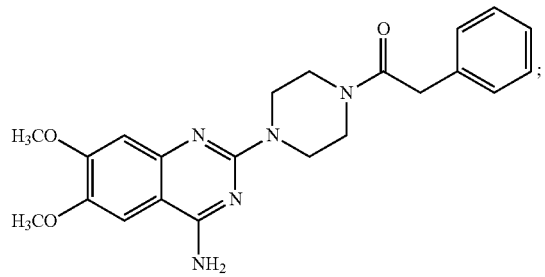
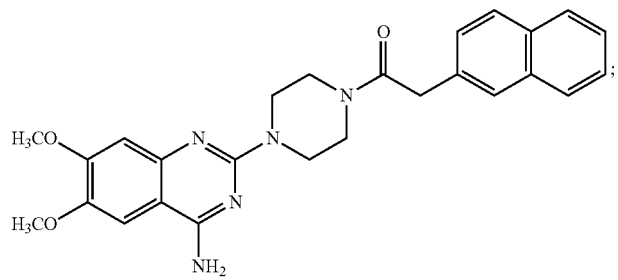
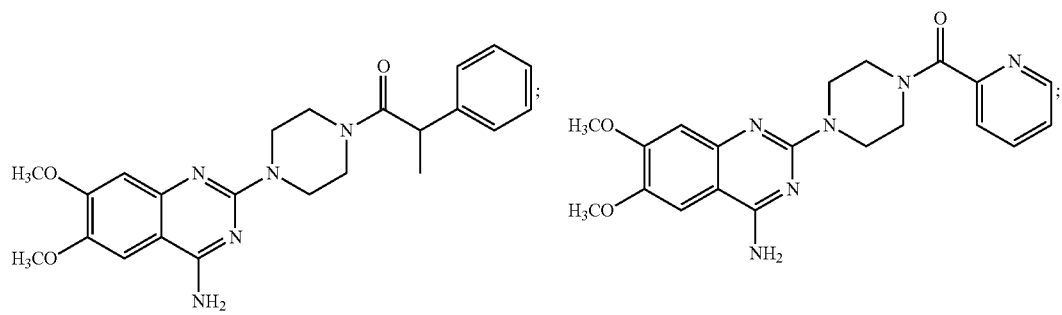
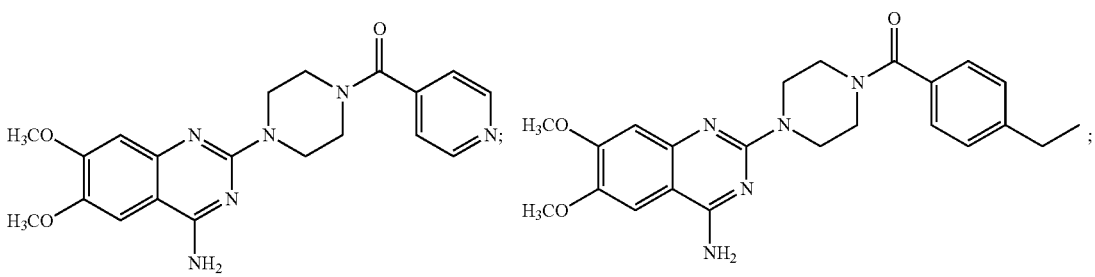

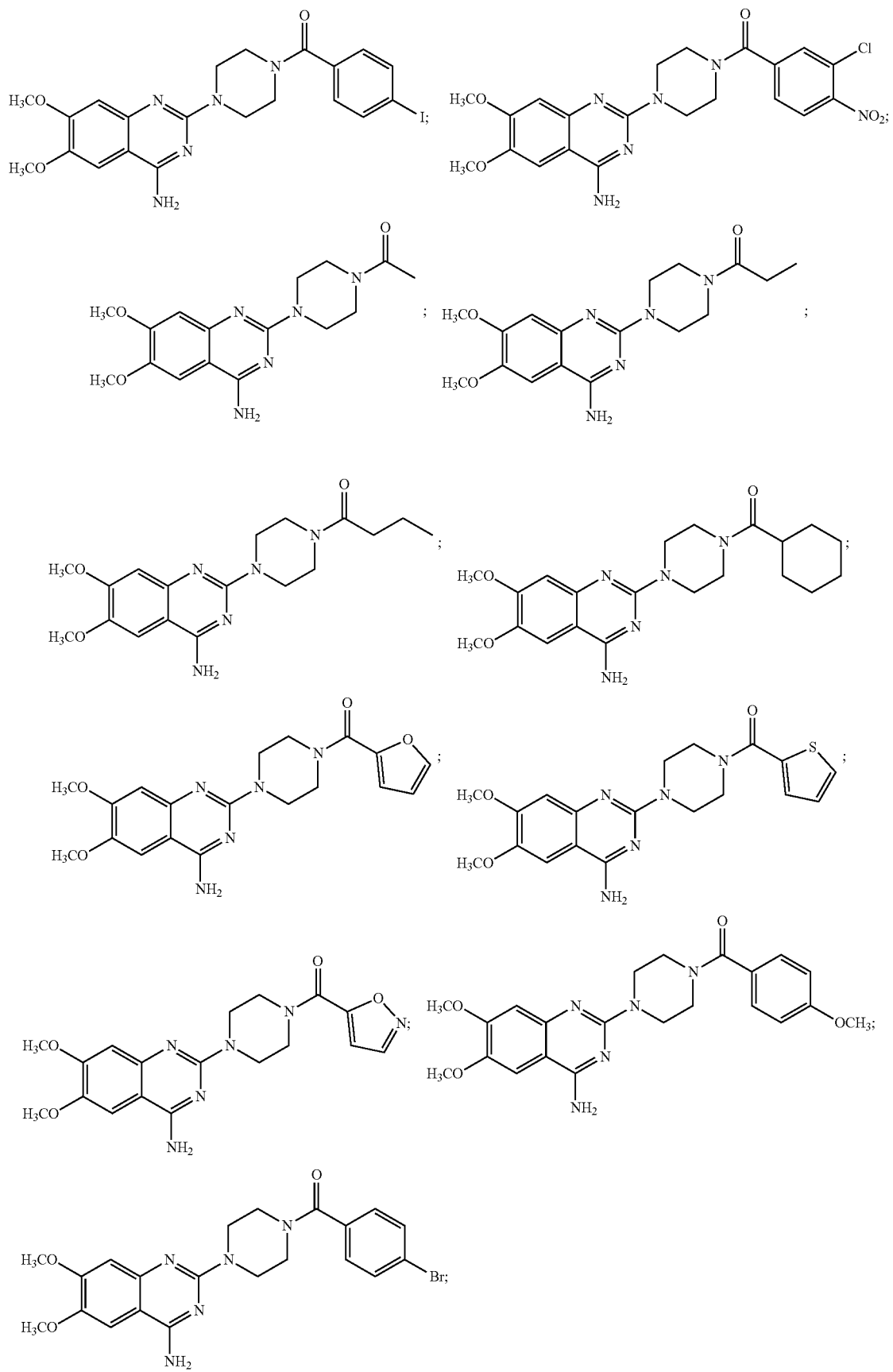

-continued
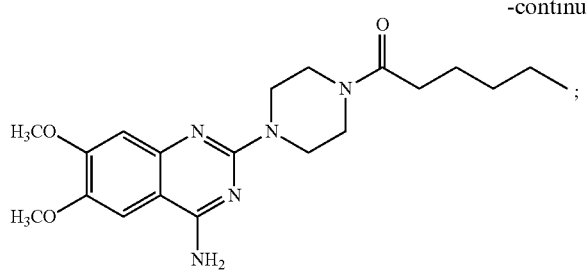
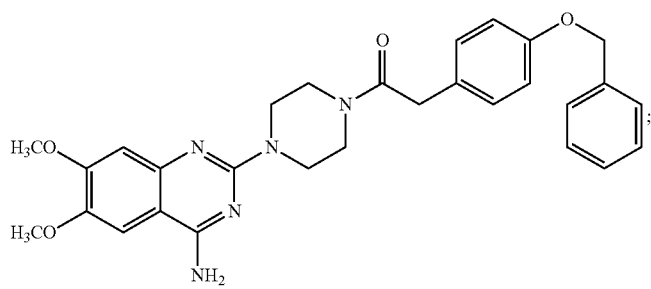
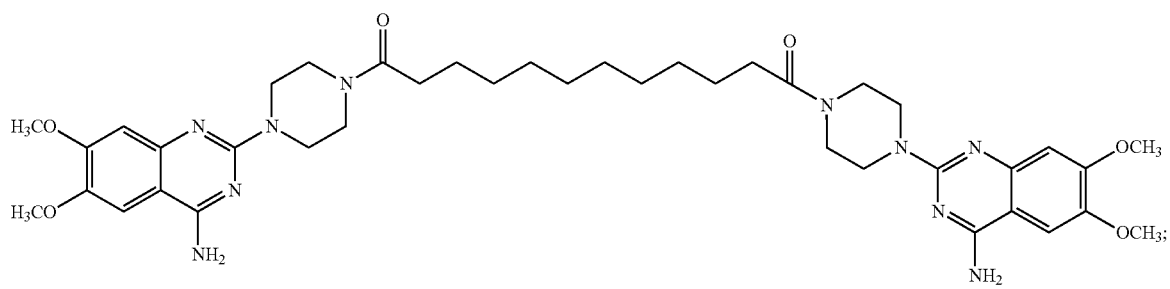
and pharmaceutically acceptable salts thereof; and a pharmaceutically acceptable carrier.
In some embodiments, the compound can have the formula:
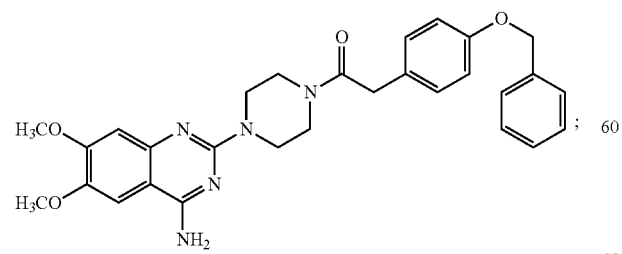
or a pharmaceutically acceptable salt thereof.

In other embodiments, the compound can have the formula:

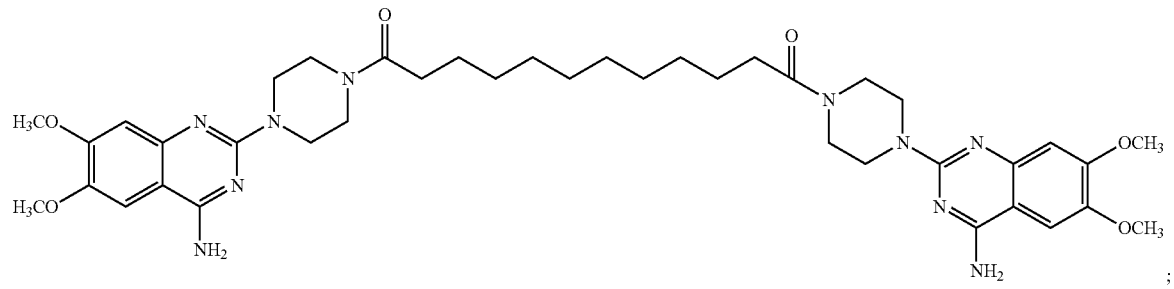 [SMILES: COc1cc2nc(N3CCN(C(=O)CCCCCCCCCCC(=O)N4CCN(c5nc(N)c6cc(OC)c(OC)cc6n5)CC4)CC3)nc(N)c2cc1OC]

or a pharmaceutically acceptable salt thereof.

BRIEF DESCRIPTION OF THE DRAWINGS

FIGS. 1(A-H) illustrate in silico screening identifies doxazosin as a novel agonist for EphA2 receptor. (A) Schematic illustration of the predicted effects of small molecule agonists in inducing ligand-dependent signaling. (B) Crystal structure of the EphA2 ligand binding domain (LBD) in complex with ephrin-A1. Highlighted are the hydrophobic pocket and arginine 103 of the EphA2-LBD that interact with the G-H loop of ephrin-A1 and glutamate 119 of ephrin-A1, respectively. EphA2-LBD was rotated ~10° counter-clockwise to better reveal the binding pocket. (C) Small molecule screening identifies doxazosin (Compound 11) as a novel EphA2 agonist. MDA-231 A2 cells were treated with Compounds 1-11 (50 µM in 0.2% DMSO) for 30 minutes and cell lysates were subject to immunoblot for phosphorylated EphA/B kinases (pEphA/B) and total EphA2. (D) Chemical structure of doxazosin (DZ). (E) Dose-response of EphA2 activation by DZ. MDA-231-A2 cells were treated with the indicated doses of DZ for 30 minutes and lysates were immunoprecipitated with an EphA2-specific antibody and blotted as in (C). Treatment with 1 µg/ml ephrin-A1-Fc (EA1-Fc) for 10 minutes served as a positive control. Note decreasing amount of EphA2 following ephrin-A1 and doxazosin treatment. (F) Immunoblots for pEphA/B on lysates from MDA-231-A2 cells pretreated with 1 µM phenoxybenzamine and then treated for 1 hour with indicated doses of DZ. Treatment with 1 µg/ml ephrin-A1-Fc (EA1-Fc) served as a positive control. Treatment with 0.2% DMSO for either 1 hour (left), or 5 hours (right) served as vehicle controls. (G) Representative plot from Surface Plasmon Resonance (SPR) analysis of DZ binding to the recombinant ligand binding domain of EphA2. Curves from bottom to top represent concentrations of 1.56, 3.13, 6.25, 12.5, 25, 50 mM. Determined $K_D$ value is shown within plot. (H) Molecular modeling of surface area diagram indicating amino acids of EphA2 potentially involved in direct interaction with doxazosin. The four amino acids of the ephrin-A1 loop are shown in red.

FIGS. 2(A-C) illustrate doxazosin activates EphA2 receptor in different cell types. (A) Immunoblots for pEphA/B on lysates from PC-3 and HEK 293-A2 (293-A2) cell lines treated for 30 minutes with indicated doses of doxazosin (DZ). (B) Immunoblots for pEphA/B on lysates from MDA-231-A2 (231-A2) and 293-A2 cell lines treated with 50 µM DZ in 0.2% DMSO for indicated times. (C) Doxazosin selectively activates EphA2 and EphA4 receptors. Immunoblots for pEphA/B on lysates from HEK 293 cell lines expressing given Eph receptors following treatment with indicated doses of doxazosin (DZ) for 60 minutes. Treatment with 1 µg/ml ephrin-A1-Fc ligand (EA1-Fc) for 10 minutes (EphA2) and 30 minutes (Vector, EphA1, EphA4), as well as 30 minute treatment with ephrin-A5-Fc (EA5-Fc) (EphA3) and ephrin-B1-Fc (EB1-Fc) (EphB3) served as positive controls. Blotting for total Eph kinases served as loading controls.

FIGS. 3(A-I) illustrate structure and dynamics of the EphA4-doxazosin complex. (A) $^1$H-$^{15}$N NMR HSQC spectra of the EphA4 LBD in the absence (blue) and in the presence (red) of doxazosin (DZ) at a molar ratio of 1:5 (EphA4:DZ). Several residues located over the convex surface of the EphA4 ephrin binding channel are labeled. (B) Residue-specific chemical shift index (CSI) of the EphA4 LBD in the presence of doxazosin at a molar ratio of 1:5 (EphA4:DZ). Significantly shifted residues shared with C1 are colored in bright brown, while the residues significantly shifted only by doxazosin binding are in red. (C) The docking model of the EphA4-doxazosin complex in ribbon. Binding regions identical to those for the C1-binding were colored in brown, while those unique for the doxazosin binding in red. G, K, M and E are used to donate b-strands of the convex surface of EphA4/ephrin-binding channel. (D) EphA4 residues having direct contacts with doxazosin. Residues on D-E and J-K loops are in brown, those on the convex surface in violet, and Arg106 in cyan. Green dashed lines indicate hydrogen bonds between doxazosin and EphA4 residues. (E)-(F) The same docking model with the electrostatic potential of the EphA4 LBD displayed. (G) EphA4 LBD in free and doxazosin-bound states display different squared generalized order parameter $S^2$. Blue: $S^2$ difference ≤−0.01; red: $S^2$ difference ≥0.01; brown: no significant change or $S^2$ values not determined. (H) Conformational exchanges of EphA4 in free (left panel) and doxazosin-bound states (right panel). Residues with $R_{ex}$>5 are displayed in balls and colored in red. (I) A docking model of the EphA2-doxazosin complex. Contact residues in D-E and J-K loops are labeled in brown, on the convex surface in cyan, and Arg103 in violet. The violet dash is used to indicate the hydrogen bonds between doxazosin and EphA2 residues.

FIGS. 4(A-B) illustrate doxazosin inhibits activation of ERK1/2 and Akt in an EphA2-dependent manner (A) Immunoblot of lysates from A172-A2 cells treated with indicated doses of doxazosin (DZ) in 0.2% DMSO for 90 minutes. Treatment with 1 µg/ml ephrin-A1-Fc ligand for 10 minutes served as a positive control. Lysates were immunoprecipitated with ephrin-A1-Fc (IP: EA1-Fc) as given in Methods, and probed for pEphA/B and total EphA2. Total cell lysates were probed for phosphorylated forms of ERK1/2 and Akt, as well as total ERK1/2 and Akt. (B) Immunoblot of total cell lysates from LK133A-Vec and LK133A-A2 cells treated with indicated doses of doxazosin (DZ) in 0.2% DMSO for 90 minutes. Treatment with 1 μg/ml ephrin-A1-Fc for 10 minutes served as a positive control. Lysates were probed for phosphorylated forms of EphA/B, Akt, and ERK1/2, as well as total EphA2, Akt, and ERK1/2.

FIGS. 5(A-C) illustrate doxazosin treatment causes EphA2 receptor internalization and induces cell rounding. (A) Immunofluorescence staining of U373-A2 cells for EphA2 receptor (red) after treatment for 60 minutes with 50 μM DZ in 0.2% DMSO. Treatment with 1 μg/ml ephrin-A1-Fc and DMSO served as positive and negative controls, respectively. DAPI nuclear staining is shown in blue. (B) Immunofluorescence staining of MDA-MB-231 cells for EphA2 receptor (red) after treatment for 120 minutes with 50 μM DZ in 0.2% DMSO. Controls are as given above. Scale bars, 25 μm. (C) Images from cell rounding analysis of PC-3 cells stimulated with 50 μM doxazosin for 30 or 60 min. Stimulation with 2 μg/ml ephrin-A1-Fc for 10 min or 0.2% DMSO served as positive and negative controls, respectively. Cells were seeded on 6-well plates and stimulated after 24 hours.

FIGS. 6(A-C) illustrate integrin-mediated cell migration toward fibronectin is suppressed by doxazosin in a dose-dependent manner MDA-MB-231 (A), A172-A2 (B), and PC3-DAB2IP KD (C) cells were subject to haptotactic cell migration toward fibronectin as described previously (see Methods). Doxazosin at indicated concentrations was presented at the lower chamber of the Transwells. Cells were allowed to migrate toward fibronectin for 4 hours. Data represent average numbers of migrating cells from 6 randomly selected fields. DMSO was used as vehicle control.

FIGS. 7(A-F) illustrate doxazosin inhibits distal metastasis of human prostate cancer cells from orthotopic xenograft and prolongs survival. (A) Fluorescent images of prostate tumors and lung metastases resulting from GFP-tagged PC3-DAB2IP KD cells after 10 days of treatment with either vehicle, or 50 mg/kg doxazosin. Tumors in the prostate gland were imaged in a GFP light box, while lung metastatic foci were visualized under an inverted fluorescence microscope. (B) Graph comparing total number of metastatic lung foci in individual vehicle-treated (n=7) and doxazosin treated (n=8) mice. (C) Quantitative analyses of total number of metastatic lung foci from different size categories. Categories were based on foci diameter measured in number of cells (small=1-3 cells, medium=4-6 cells, large=7-10 cells). (D) Comparison of total metastatic burden (number of foci×foci diameter) in mice treated with vehicle control vs. those treated with doxazosin. (E) Graph comparing bodyweights of vehicle- and doxazosin-treated mice. Bars represent mean bodyweights. Error bars represent the SEM. Experiment was repeated three times with similar results. (F) Kaplan-Meier Plot showing prolonged survival in mice treated with doxazosin (n=8) compared with those treated with vehicle control (n=9). Mice were injected with the PC3-DAB2IP KD cells and treated as in (A) and closely monitored for survival. Those that became moribund were sacrificed. Similar results were obtained from three independent experiments.

FIG. 9 is an image of GFP-positive primary tumors in DZ treated mice compared to vehicle control. Mice are treated for 24 and 26 days.

FIG. 11 illustrates the amount of metastasis-free mice when treated with DZ compared to vehicle control.

FIG. 12 illustrates the number and severity of mice with lung metastasis when treated with DZ compared to vehicle control.

FIG. 16 is a series of graphs illustrating adrenoceptor antagonist activities of the BW25, BW22, BW26 and BW27.

FIG. 17 illustrates the EphA activation by compounds BW1-3 in 231-A2 cells.

FIG. 18 illustrates the EphA activation by compounds BW7-9 in 231-A2 cells.

FIG. 20 illustrates the EphA activation by compounds BW10-12 in 231-A2 cells.

FIG. 23 illustrates the EphA activation by compounds BW19-21 in 231-A2 cells.

FIG. 25 illustrates the EphA activation by compounds BW1, BW2, BW3, BW10, BW11, and BW12.

FIG. 26 illustrates modifications of Doxazosin.

FIG. 30 illustrates compounds 27, 24 and Doxazosin docking with EphA2. EphA2 (PDB:3FL7) out membrane part was used to perform the docking study. The original identified Doxazosin binding site was used to fit the compounds. Compound 24 and Doxazosin share the similar binding mode, whereas compound 27 shows a different binding characteristic.

DETAILED DESCRIPTION

Figure 8:
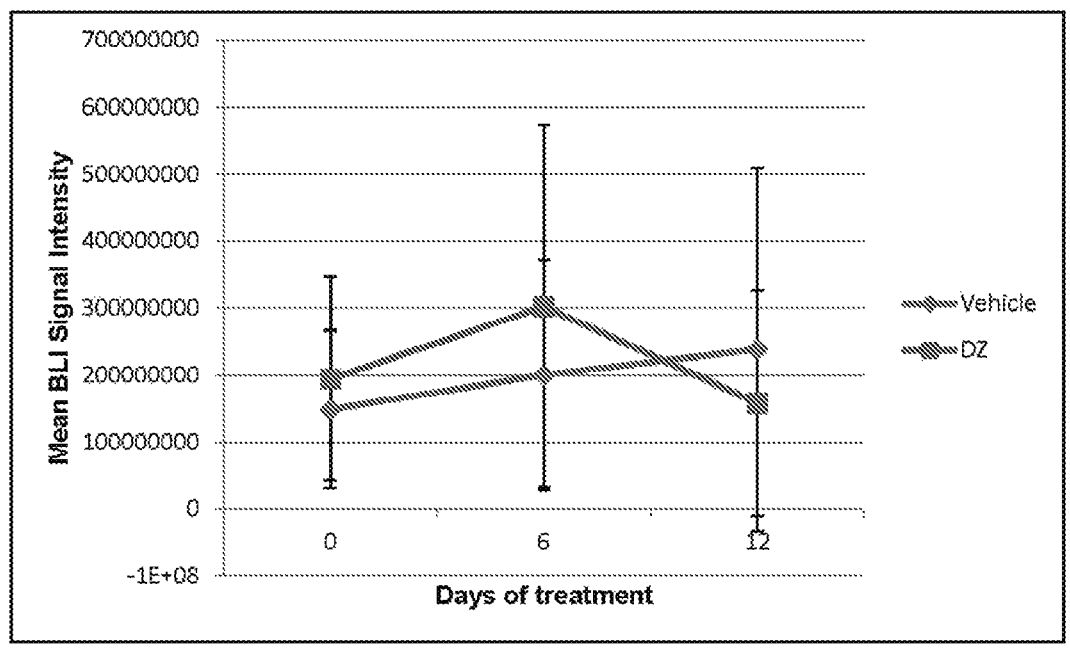
FIG. 8 is a graph illustrating the change in primary tumor size with DZ treatment compared to vehicle control. Treatment began on day 13-post-implantation. Treated with 50 mg/kg DZ. Vehicle=10% Cremophor/5% DMSO/PBS.
Figure 10:
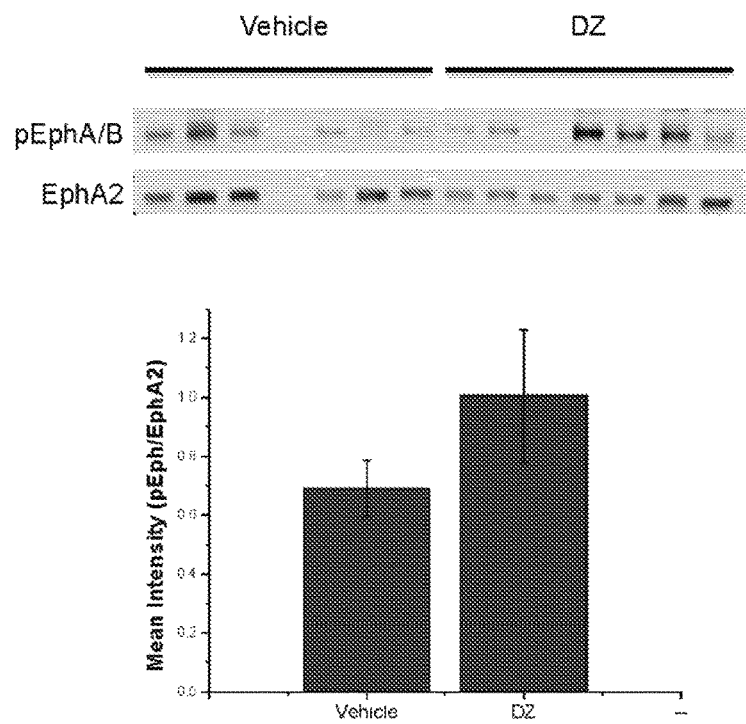
FIG. 10 illustrates EphA2 activation in primary tumor lysates treated with DZ compared to vehicle control.
Figure 13:
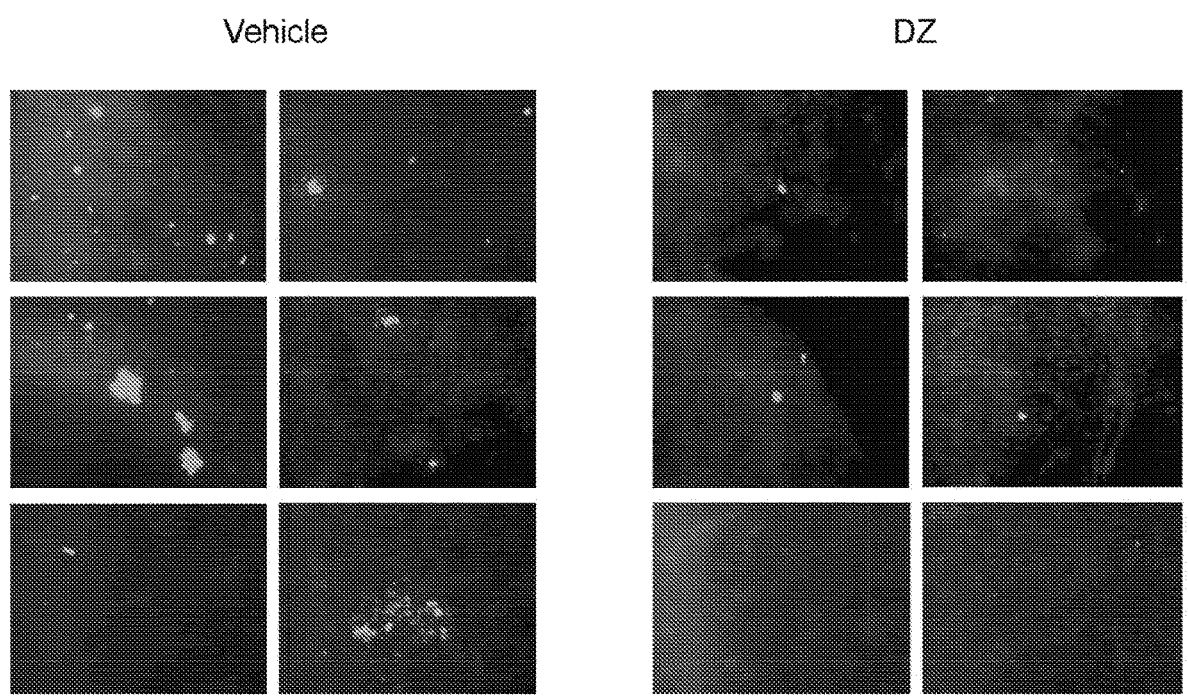
FIG. 13 illustrates GFP-positive lung metastases in DZ treated mice compared to vehicle control.
Figure 14:
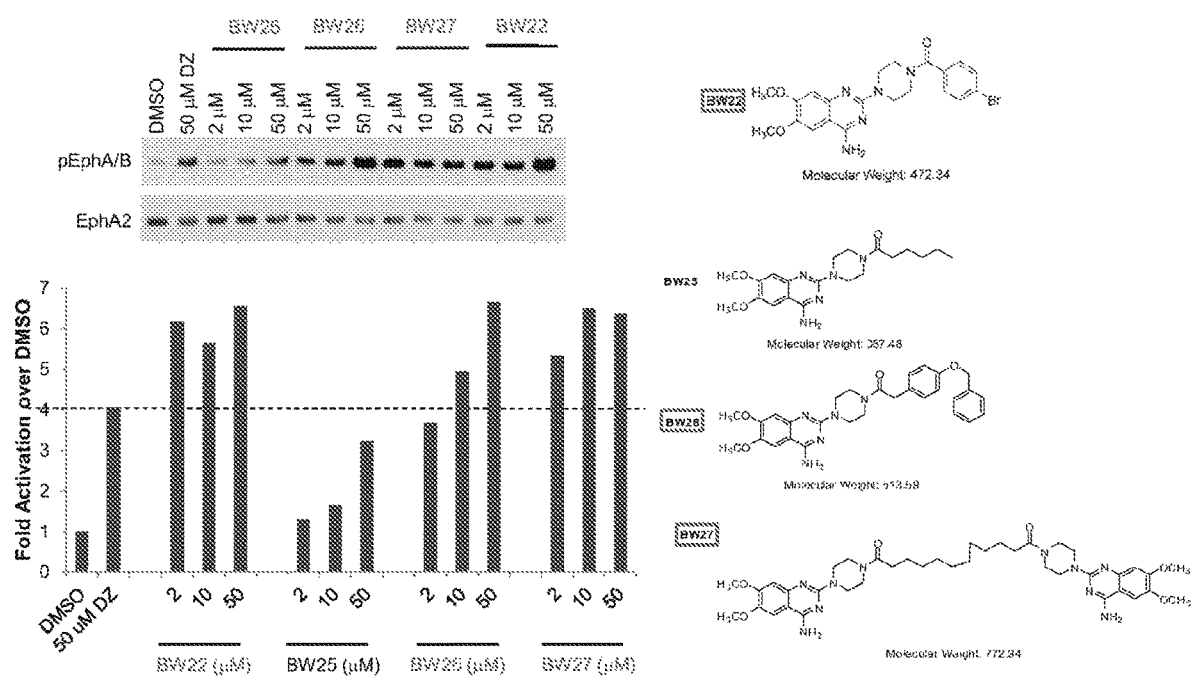
FIG. 14 illustrates three derivatives of DZ are at least 25-fold more potent that DZ.
Figure 15:
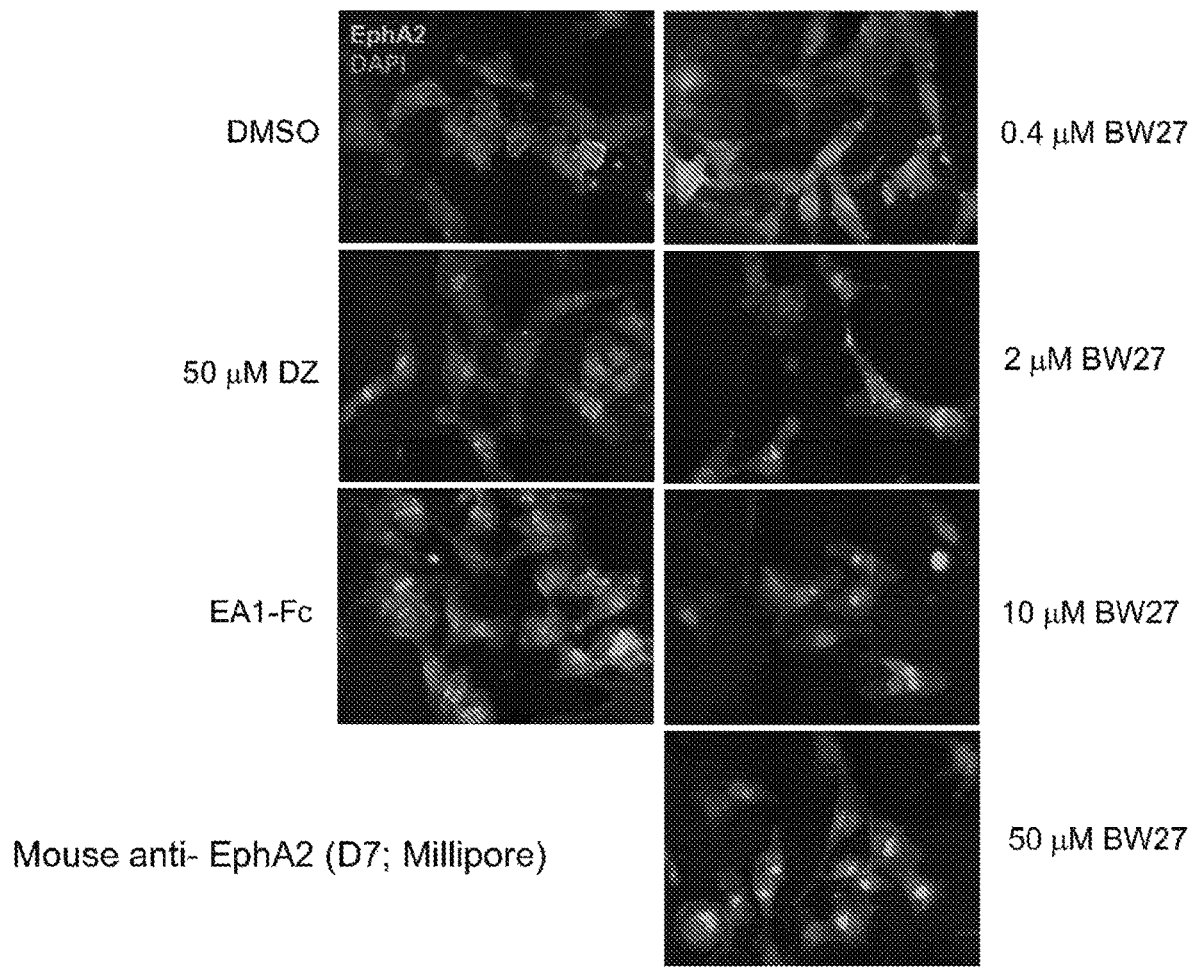
FIG. 15 is a series of images showing EphA2 internalization by BW27.
Figure 19:
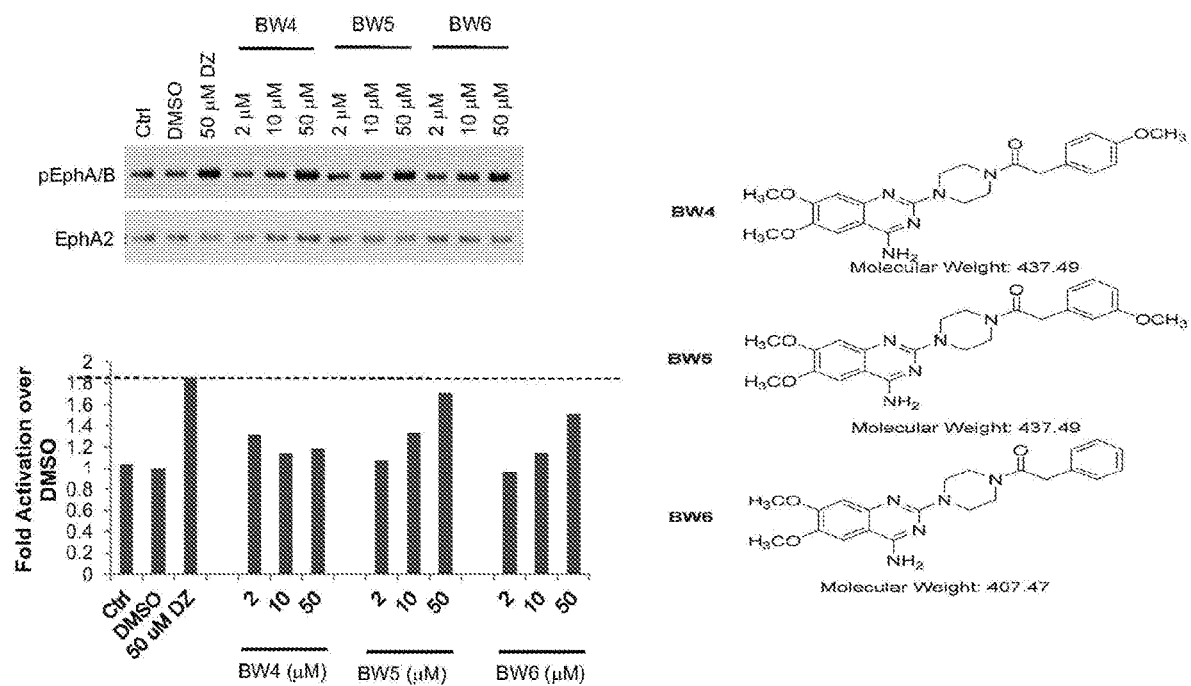
FIG. 19 illustrates the EphA activation by compounds BW4-6 in 231-A2 cells.
Figure 21:
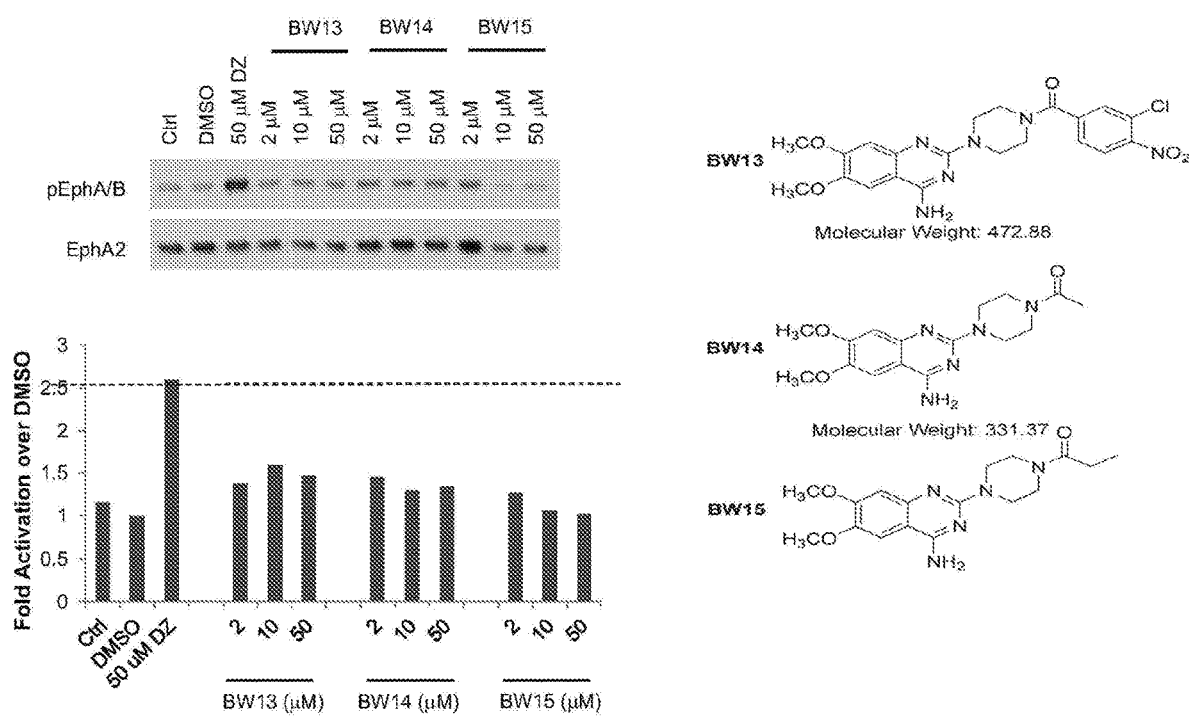
FIG. 21 illustrates the EphA activation by compounds BW13-15 in 231-A2 cells.
Figure 22:
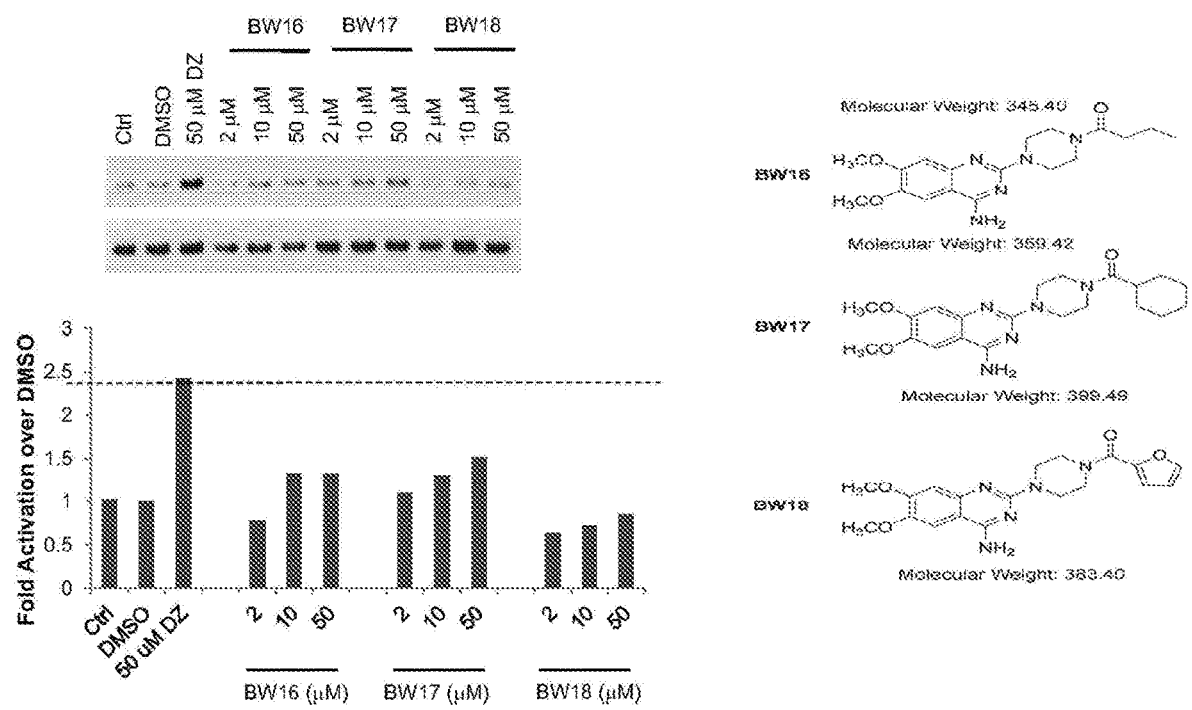
FIG. 22 illustrates the EphA activation by compounds BW16-18 in 231-A2 cells.
Figure 24:
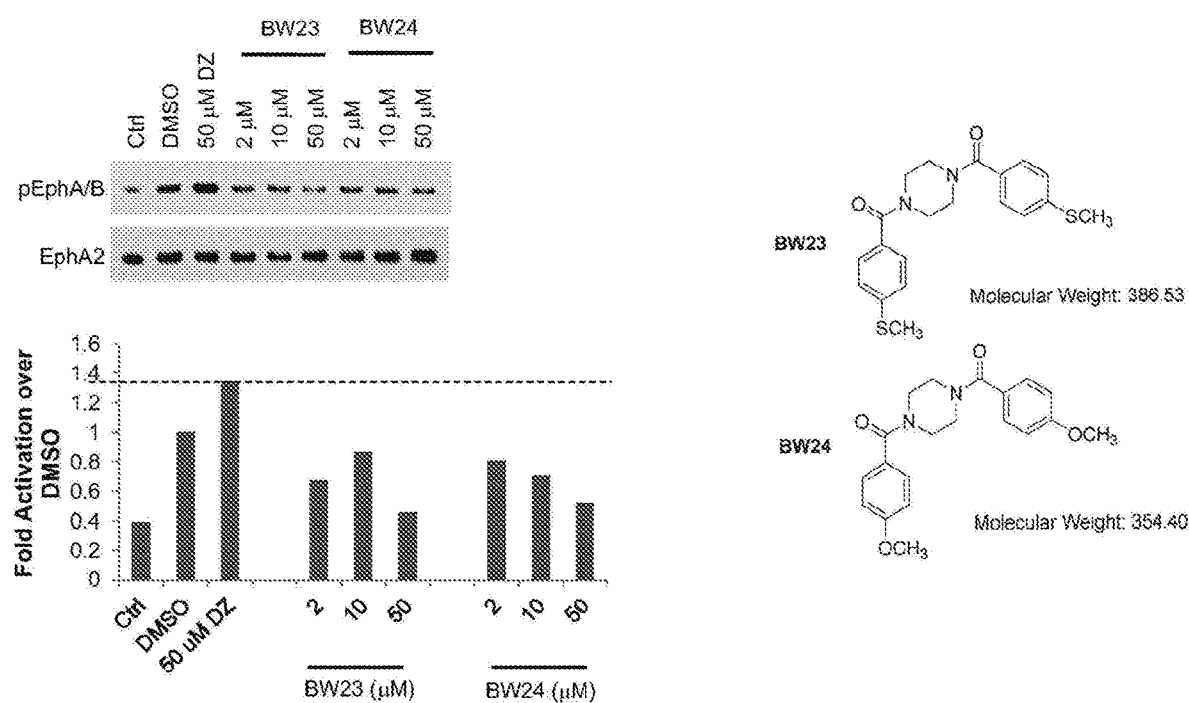
FIG. 24 illustrates the EphA activation by compounds BW23-24 in 231-A2 cells.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same.

"Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3rd ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H2O, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "IC50," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., C1-6), it is meant to encompass each number within the range as well as all intermediate ranges. For example, "C1-6 alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, C1-6 alkyl is intended to include C1, C2, C3, C4, C5, and C6 alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., C1-C6 for straight chain, C3-C6 for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —CH2CH2—, i.e., a C2 alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "C1-C6 alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF3, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-(C1-C24 alkyl)-substituted carbamoyl (—(CO)—NH(C1-C24 alkyl)), di-(C1-C4 alkyl)-substituted carbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (-CN), isocyano (—N+C—), cyanato (—O—CN), isocyanato (—ON+C—), isothiocyanato (—S—CN), azido (—N=N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C6-C20 arylamido (—NH—(CO)-aryl), imino (—CR=NH where R=hydrogen, C1-C24 alkyl, C5-C20 aryl, C6-C24 alkaryl, C6-C24 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO2), nitroso (—NO), sulfo (—SO2—OH), sulfonato (—SO2—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO2-aryl), phosphono (—P(O)(OH)2), phosphonato (—P(O)(O—)2), phosphinato (—P(O)(O—)), phospho (—PO2), and phosphino (—PH2); and the hydrocarbyl moieties C1-C24 alkyl, C2-C24 alkenyl, C2-C24 alkynyl, C5-C20 aryl, C6-C24 alkaryl, and C6-C24 aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

Embodiments described herein relate to methods and compositions that provide for the treatment, inhibition, and management of diseases and disorders associated with the expression or overexpression of EphA2 and/or cell hyperproliferative diseases and disorders. It has been shown using structure-based virtual screening and cell-based assays that Doxazosin functions as a small molecule agonist for EphA2 that is capable of inhibiting cancer cell growth and metastasis. It was found that analogues of Doxazosin, which were identified using in silico screening assays and cell based assays described herein, have enhanced affinity and specificity to EphA2 compared to Doxazosin, and can be used to treat cancer cells that overexpress EphA2.

In some embodiments, the EphA2 agonists described herein can inhibit cancer cell proliferation, invasion, and survival, particularly those cancer cells that overexpress EphA2 or cancer cells that have a hyperactive Ras/Raf/Mek/ERK1/2 and/or PI3/AKT signaling pathway. The EphA2 agonists described herein can be used in methods and as therapeutic agents for the treatment, inhibition or management of metastases of cancers of epithelial cell origin, especially human cancers of the breast, lung, skin, prostate, bladder, and pancreas, and renal cell carcinomas and melanomas EphA2 Agonists Generally, the EphA2 agonists include, but are not limited to, small molecules that have a molecular weight of about 50 daltons to about 2,500 daltons. In certain aspects, the EphA2 agonists can include a small molecule compound; such as those which activate EphA2 kinase function as well as those that suppress AKT kinase function and MAPK/ERK1/2 function. As illustrated in FIG. 1A, such agonists may not only sever the pro-oncogenic Akt-EphA2 crosstalk, but also reactivate intrinsic ligand-dependent tumor suppressor functions of EphA2. In some embodiments, the EphA2 agonist has a lower α-adrenoreceptor binding affinity than doxazosin.

As described herein, small molecule EphA2 agonists may comprise functional groups necessary for structural interaction with proteins, particularly hydrogen bonding, and typically include at least an amine, carbonyl, hydroxyl, sulfhydryl or carboxyl group. These small molecule compounds are also referred to herein as EphA2 agonistic compounds. Optionally, these agonistic compounds can specifically target the ligand-binding domain of EphA2 kinase.

In some embodiments, the small molecule EphA2 agonist compounds have the general formula:

A-L-X—Z       (I), wherein A is a substituted or unsubstituted aryl or heteroaryl;
L is

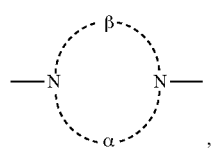

wherein α and β can each individually represent $(CH_2)_m$ (m is an integer from 2 to 4) and β is optionally present;
X is C=O or $SO_2$; and
Z is —Y—$(R^1)_n$, wherein Y is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl), wherein Z is not a 1,4 benzodioxin when A is an 4-Amino-6,7-dimethoxy-2-quinazolinyl, $R^1$ is optionally present and if present is a structurally similar monomer of A-L-X and is linked to X via Y, and n is an integer from 0-10, thereby forming a dimer, trimer, or dendrimer molecule of A-L-X monomers, and pharmaceutically acceptable salts thereof.

In some embodiments, A is selected from a 6,7-di-alkoxy substituted 4-quinazolinamine having the formula:

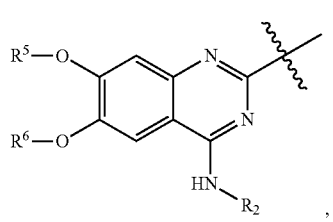

wherein $R^2$, $R^5$, and $R^6$ are independently selected from H, an alkoxy (e.g., acetyl) or a $C_{1-6}$alkyl (e.g., methyl) group.

In certain embodiments, A is selected from:

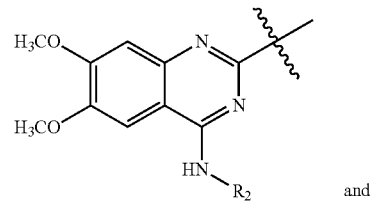

and

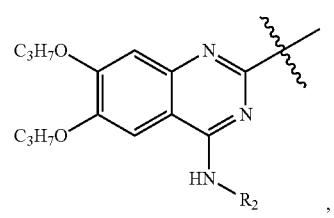

, wherein $R^2$ is independently selected from H, an alkoxy (e.g., acetyl) or a $C_{1-6}$alkyl (e.g., methyl) group.

In other embodiments, A is selected from:

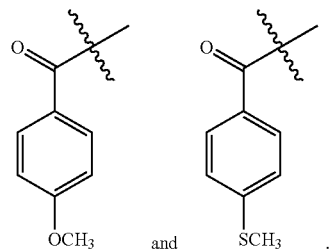 [SMILES: *C(=O)c1ccc(OC)cc1 ; *C(=O)c1ccc(SC)cc1]

In some embodiments L is:

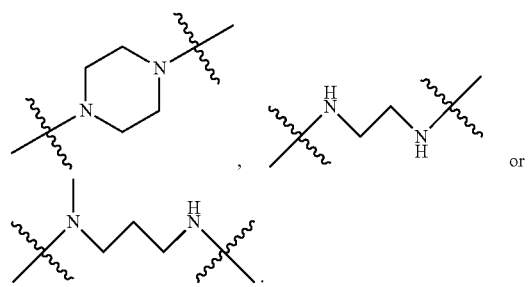

In some embodiments, the EphA2 agonist can also include a small molecule having the formula:

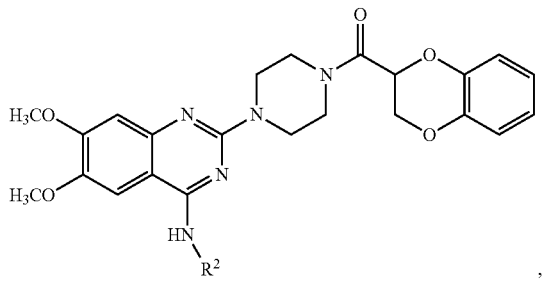

wherein $R^2$ is selected from H, an alkoxy (e.g., acetyl) or a $C_{1-6}$alkyl (e.g., methyl) group.

In other embodiments, the EphA2 can include a small molecule having the formula (II):

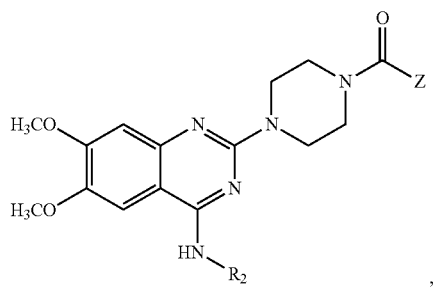

(II)

wherein Z is —Y—$(R^1)_n$, $R^2$ is selected from H, an alkoxy (e.g., acetyl) or a $C_{1-6}$alkyl (e.g., methyl) group, Y is a substituted or unsubstituted $C_1$-$C_{24}$ alkyl, $C_2$-$C_{24}$ alkenyl, $C_2$-$C_{24}$ alkynyl, aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl), $R^2$ is selected from H, an alkoxy (e.g., acetyl) or a $C_{1-6}$alkyl (e.g., methyl) group, $R^1$ is optionally present and if present is a structurally similar monomer of formula (III):

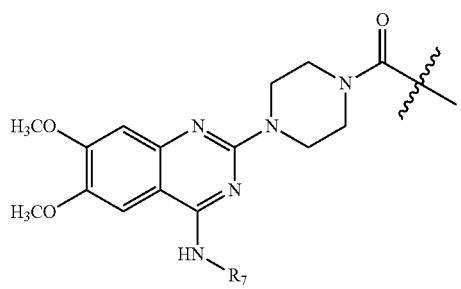

(III)

$R^7$ is selected from H, an alkoxy (e.g., acetyl) or a $C_{1-6}$ alkyl (e.g., methyl) group and n is an integer from 0-10, thereby forming a dimer, trimer, or dendrimer molecule of monomers, and pharmaceutically acceptable salts thereof.

In some embodiments, the EphA2 agonist have formula (II) can include a small molecule having the formula:

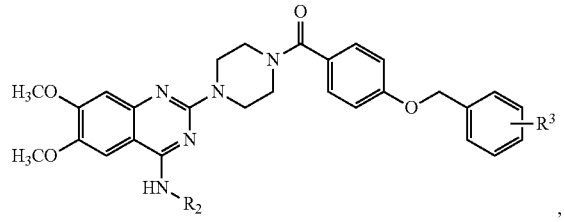

wherein $R^2$ is selected from H, an alkoxy (e.g., acetyl) or a $C_{1-6}$alkyl (e.g., methyl) group, and $R^3$ is selected from H, halogen, $C_{1-6}$alkyl, $C_{1-6}$aralkyl, $C_{1-6}$heterocyclylalkyl, and $C_{1-6}$carbocyclylalkyl.

The EphA2 agonist of formula can also include a small molecule having the formula:

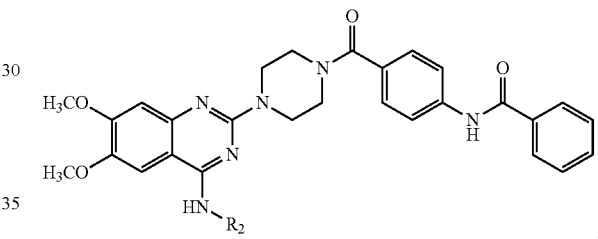

wherein $R^2$ is selected from H, an alkoxy (e.g., acetyl) or a $C_{1-6}$alkyl (e.g., methyl) group, and $R^4$ is selected from H, halogen, $C_{1-6}$ alkyl, $C_{1-6}$ aralkyl, $C_{1-6}$ heterocyclylalkyl, and $C_{1-6}$ carbocyclylalkyl.

In other embodiments, an EphA2 agonists having formula (II) can be selected from the group consisting of:

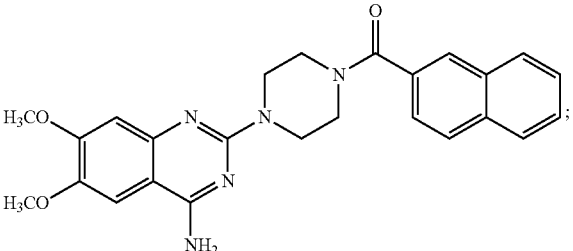

;

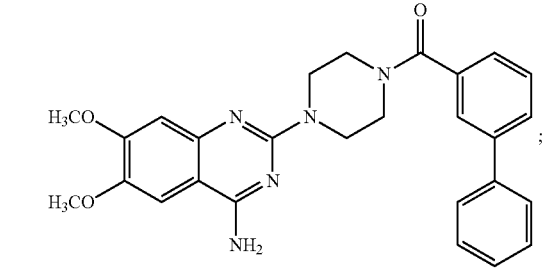

;

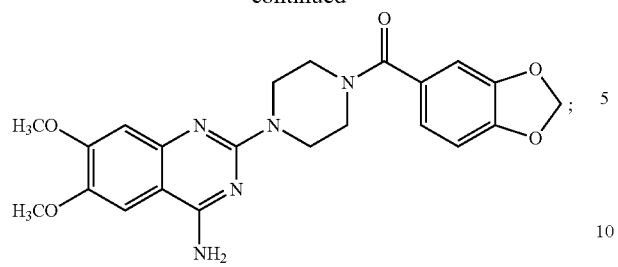
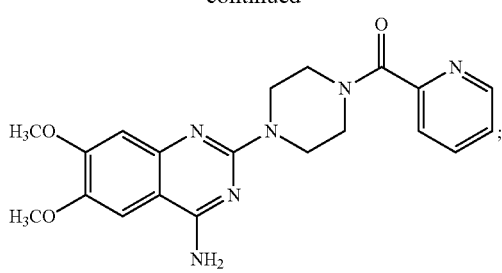
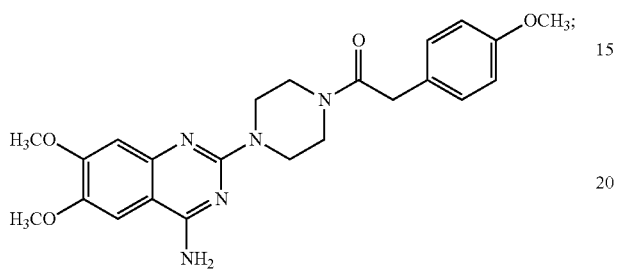
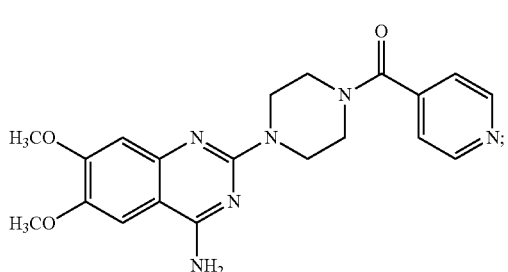
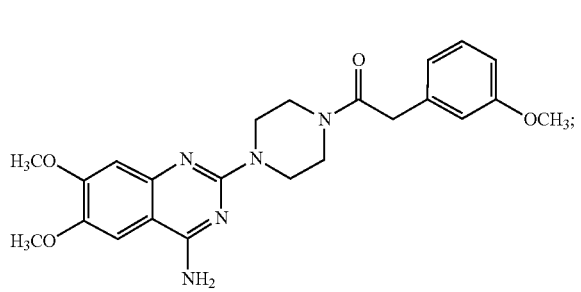
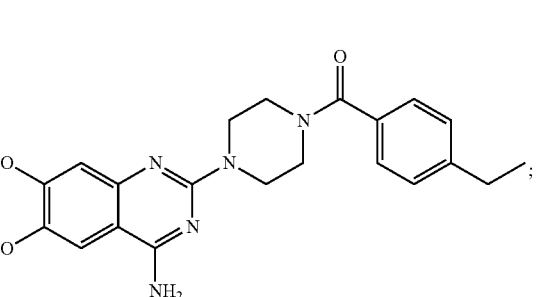
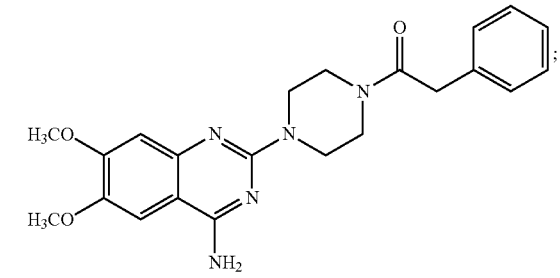
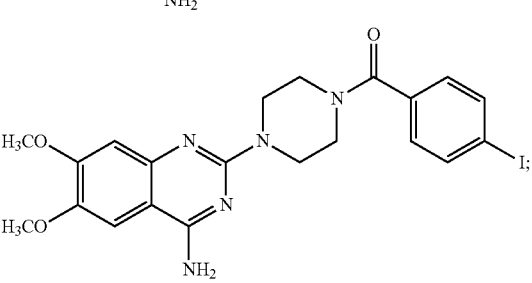
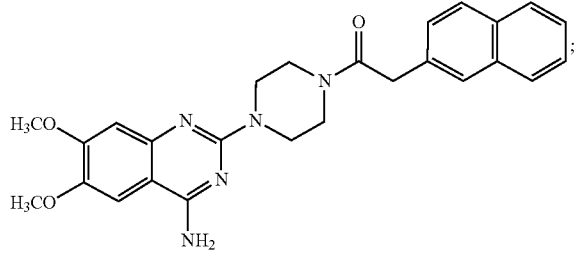
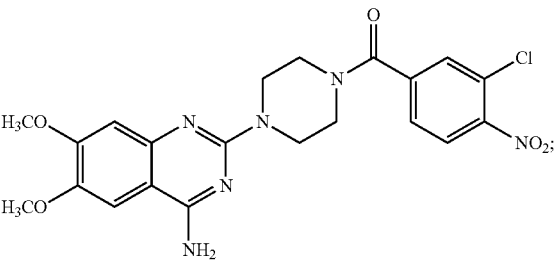
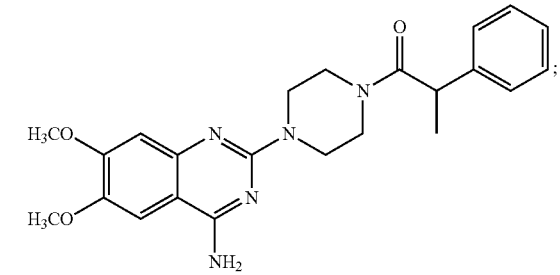
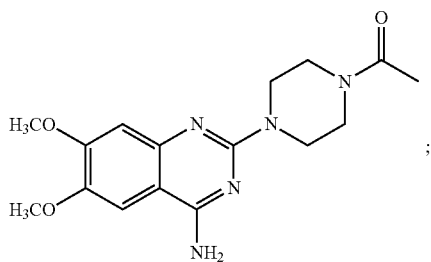

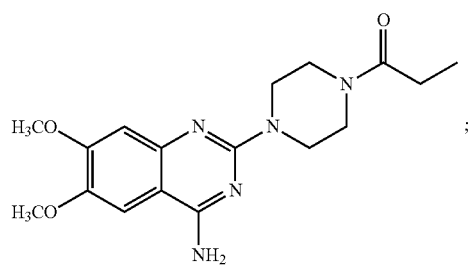
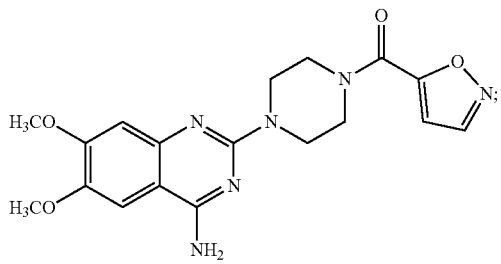
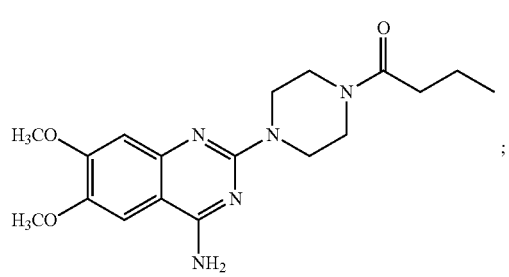
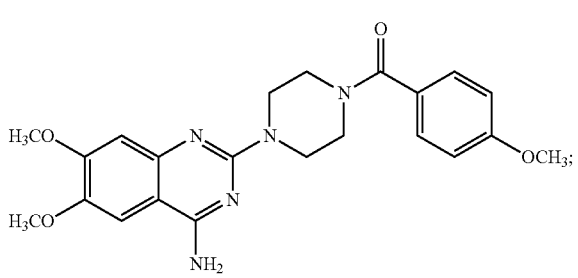
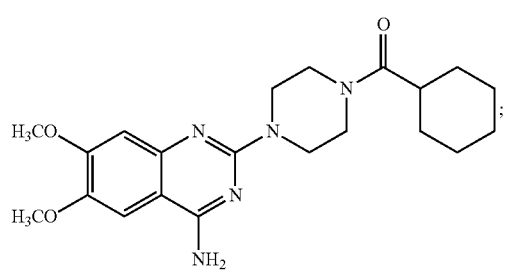
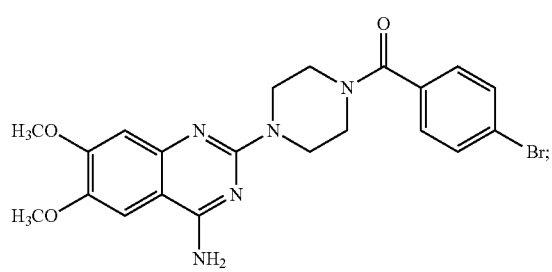
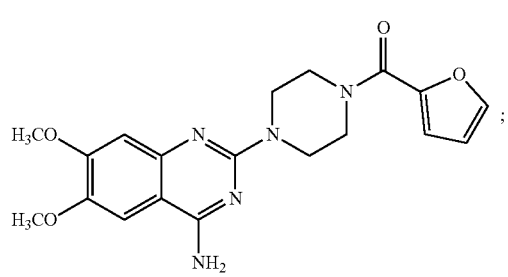
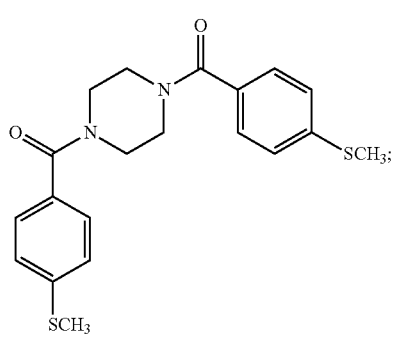
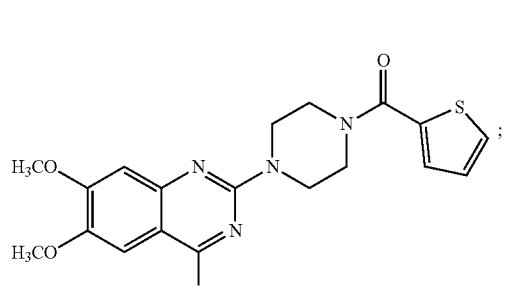
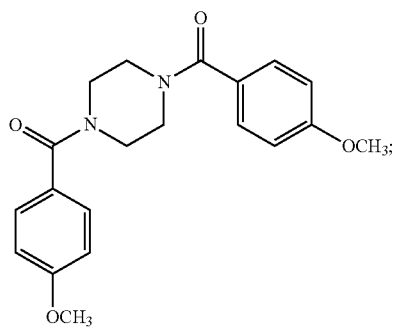

-continued

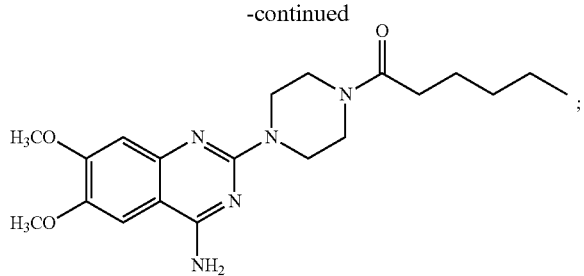

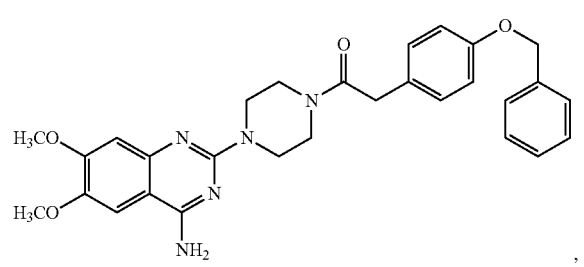 [SMILES: COc1cc2nc(N3CCN(C(=O)Cc4ccc(OCc5ccccc5)cc4)CC3)nc(N)c2cc1OC]

(compound 24), and pharmaceutically acceptable salts thereof.

(compound 24) or a pharmaceutically acceptable salt thereof.

In certain embodiments, the EphA2 agonist is not doxazosin.

In some aspects, the EphA2 agonist can include a dimer, trimer, or dendrimer molecule that includes two or more substantially similar monomers having the formula A-L-X described above. In certain aspects, A-L-X monomers can be linked by Y. Y can be, for example, a substituted or unsubstituted $C_1$-$C_{24}$ alkyl, $C_2$-$C_{24}$ alkenyl, $C_2$-$C_{24}$ alkynyl, aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl).

In other aspects, the dimer molecule can be a homodimer molecule. Examples of homodimer EphA2 agonist can have the formula:

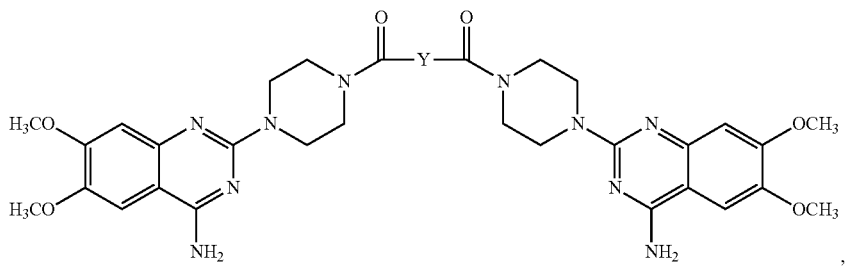

In some embodiments, the EphA2 agonist having formula (II) is

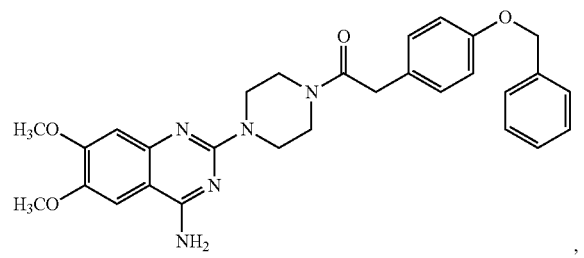

wherein Y is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), or $C_6$-$C_{20}$ arylcarbonato (—O—(CO)—O-aryl).

For example, a homodimer EphA2 agonist can include a small molecule having the formula:

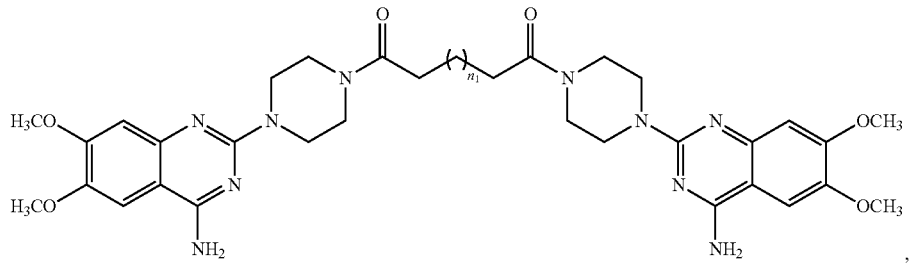

wherein $n_1$ is an integer from 1-20. In one particular embodiment, a homodimer EphA2 agonist has the formula:

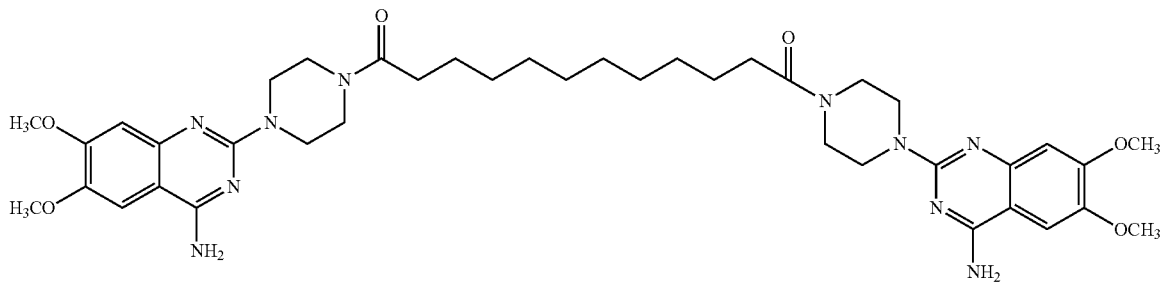 [SMILES: COc1cc2nc(N3CCN(C(=O)CCCCCCCCCCC(=O)N4CCN(c5nc(N)c6cc(OC)c(OC)cc6n5)CC4)CC3)nc(N)c2cc1OC]

(compound 27) or a pharmaceutically acceptable salt thereof.

In other embodiments, a homodimer EphA2 agonist can include a small molecule having the formula:

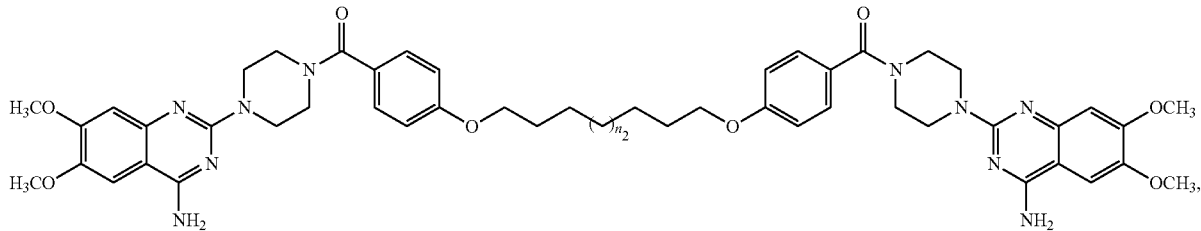

wherein $n_2$ is an integer from 1-18 or a pharmaceutically acceptable salt thereof.

Small molecule EphA2 agonist compounds described herein can be further modified through conventional chemical, physical, and biochemical means. For example, EphA2 agonist compounds described herein may be subjected to directed or random chemical modifications, such as acylation, alkylation, esterification, and amidification, to produce structural analogs.

In other embodiments, an EphA2 agonist compounds described herein can be included in a small molecule based proteolysis-targeting chimera (PROTAC) where the EphA2 agonist is coupled to a moiety that specifically recruits an E3 ligase. A small molecule PROTAC including an EphA2 agonist and a moiety that specifically recruits an E3 ligase can form a ternary complex upon binding to both its E3 ligase target and EphA2. Since the EphA2 functions as an oncogene in late stage malignant tumors, the EphA2 functions as an oncogene in late stage malignant tumors, without being bound by theory it is believed that small molecule based PROTAC including an EphA2 agonist linked to a moiety that specifically recruits an E3 ligase can: 1) activate the intrinsic tumor suppressor function of EphA2; and 2) induce EphA2 degradation after it is endocytosed.

Exemplary moieties that specifically recruit an E3 ligase as well as suitable linkers for use in compositions and methods of the present invention are described in Toure and Crews, Small-Molecule (2016) *PROTACS: New Approaches to Protein Degradation*, Agnew. Chem. Int. Ed. 2016, 55, 1966-1973, which is herein incorporated by reference in its entirety. In one embodiment, the moiety that specifically recruits an E3 ligase can have the formula:

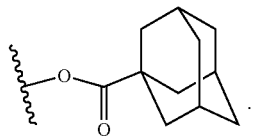 [SMILES: *OC(=O)C12CC3CC(CC(C3)C1)C2]

A moiety that specifically recruits an E3 ligase can be coupled either directly or indirectly to an EphA2 agonist. In some embodiments, the moiety that specifically recruits an E3 ligase is linked to an EphA2 agonist via a linker. A linker may be of variable length and composition so long as the two domains are bridged without serious steric interference. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof. In certain embodiments, the linker can include an (OCH2)$_n$ linker, wherein n=1-10. In certain embodiments, n=4.

In an exemplary embodiment, a PROTAC including EphA2 agonist is coupled to a moiety that specifically recruits an E3 ligase can have the formula:

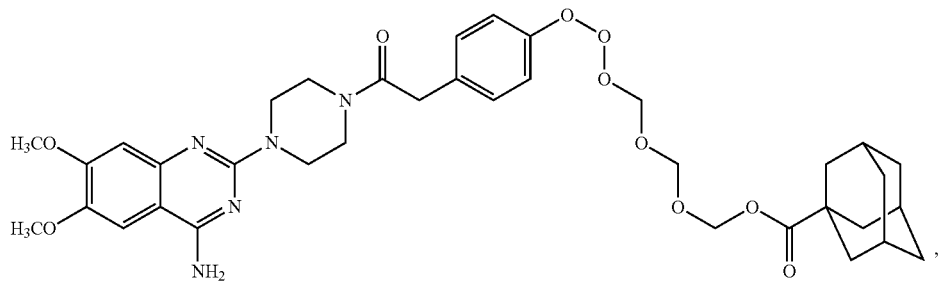 [SMILES: COc1cc2nc(N3CCN(C(=O)Cc4ccc(OOOCOCOCOC(=O)C56CC7CC(CC(C7)C5)C6)cc4)CC3)nc(N)c2cc1OC]

or a pharmaceutically acceptable salt thereof.

An agent having the general formulas described above and further modifications thereof can be assayed in order to determine the therapeutic efficacy of the agent. For example, exemplary agents may be assayed for one or more of the following activities: bind to an EphA2 receptor protein (e.g., a ligand binding domain or a dimerization domain of an EphA2 protein), stimulate tyrosine phosphorylation of an EphA2, enhance binding of an EphA2 ligand to an EphA2, enhance dimerization of an EphA2, enhance expression of an EphA2 (mRNA or protein), inhibit cancer cell proliferation, inhibit cancer cell adhesion, proliferation, spreading and/or migration, and/or suppress or inhibit signaling of the PI3/AKT pathway and/or MAPK/ERK1/2 pathway. These above-mentioned activities that characterize the agents of the present invention will also be referred to herein as "desired antitumor activity." Without being bound by theory, an agent identified by the subject methods as having one or more of the desired activities can be therapeutically effective in a method of treating cancer in a subject.

Assays for determining the therapeutic efficacy of a given agent can include cell free system assays. In many drug screening programs that test libraries of chemical compounds high throughput assays are desirable to increase the number of agents surveyed in a given period of time. Assays that are performed in cell-free systems, may be derived with purified or semi-purified proteins, are often preferred as "primary" screens in that they can be generated to permit rapid development and relatively easy detection of an alteration in a molecular target which is mediated by a test agent. Cell free systems include in vitro systems (preparations of proteins and agents combined in a test tube, Petri dish, etc.), as well as cell free systems such as those prepared from egg extracts or reticulocyte lysates. Moreover, the effects of cellular toxicity and/or bioavailability of the test agents can be generally ignored in such a system, the assay instead being focused primarily on the effect of the agent.

A primary screen can be used to narrow down agents that are more likely to have an effect on cancer progression, in vitro and/or in vivo. Such a cell free system for use in the present invention may include a biochemical assay measuring activity of an EphA2 protein. To further illustrate, an EphA2 polypeptide may be contacted with one or more agents and the ability of the agent to enhance the activity of the EphA2 polypeptide can be measured. The activity of the EphA2 polypeptide can be assessed by comparing the tyrosine phosphorylation level of the EphA2 polypeptide. One or more agents which increase the tyrosine phosphorylation level, in comparison to the tyrosine phosphorylation level of the EphA2 polypeptide in the absence of the one or more agents, is a candidate agent for use in the subject methods. Similarly, an EphA2 polypeptide may be contacted with one or more agents (e.g., individual candidate agents, combinations of two or more agents) and the ability of the agent to decrease the tyrosine phosphorylation level of an EphA2 can be measured.

The efficacy of a given agent can be assessed by generating dose response curves from data obtained using various concentrations of the test agent. Moreover, a control assay can also be performed to provide a baseline for comparison. Such candidates can be further tested for efficacy in inhibiting proliferation of cancer cells in vitro, for efficacy in inhibiting adhesion, spreading or migration of cancer cells in vitro, for efficacy in increasing the activity and/or expression of the EphA2 in other assays, for efficacy in tumor growth or spreading (e.g., prostate cancer) in vitro or in vivo. For example, the efficacy of the agent can be tested in vivo in any of the prostate or breast cancer animal models, as described herein.

In addition to cell-free assays, such as described above, the invention further contemplates the generation of cell-based assays for identifying agents having one or more of the desired anti-tumor activities. Cell-based assays may be performed as either a primary screen, or as a secondary screen to confirm the activity of agents identified in a cell free screen, as outlined in detail above. Such cell based assays can employ any cell-type. Exemplary cell types include cancer cell lines, primary tumor xenoplant cultures, and prostate cells. Cells in culture are contacted with one or more agents, and the ability of the one or more agents to inhibit cell proliferation or migration/adhesion is measured. Agents which inhibit cell proliferation or migration/adhesion are candidate agents for use in the subject methods of inhibiting cancer development.

One class of agents that may enhance the activity and/or expression of an EphA2 are agents having the general formula (I) which bind directly to an EphA2 protein. Accordingly, the present invention contemplates screening for agents having the general formula (I) which bind to, either directly or indirectly an EphA2 protein.

There are numerous approaches to screening for small molecule EphA2 agonistic therapeutic agents in tumor therapy. For example, an assay can be carried out to screen for compounds having formula (I) that specifically enhance binding of an EphA2 ligand to an EphA2 receptor. As used herein, the term EphA2 includes a full-length and a portion of an EphA2 polypeptide such as a ligand-binding domain. Compounds identified through this screening can then be tested in animal models of cancer (e.g., tumor xenografts implanted in nude mice) to assess their anti-tumor activity in vivo. For example, the identified agents can be tested in prostate cancer models such as the TRAMP (transgenic adenocarcinoma mouse prostate) mouse, the Nkx 3.1 gene knockout mouse, or any other suitable knockout animals.

In one embodiment of an assay to identify an agent that enhances interaction of two cell surface molecules (e.g., an ephrin A1 and EphA2), samples of cells expressing one type of cell surface molecule (e.g., EphA2, a soluble portion thereof, or a EphA2 fusion protein such as a fusion of the ligand-binding domain and the Fc domain of IgG) are contacted with either labeled ligand (e.g., ephrin A1) plus a test agent (or group of test agents). The amount of labeled ligand which has bound to the cells is determined. A higher amount of label (where the label can be, for example, a radioactive isotope, a fluorescent or colormetric label) in the sample contacted with the test agent(s) is an indication that the test agent(s) enhance or induce binding. The reciprocal assay using cells expressing an EphA2 ligand (e.g., ephrin A1 or a soluble form thereof) can be used to test for an agent that enhances or induces the binding of an EphA2 receptor or soluble portion thereof.

An assay to identify a substance which enhances interaction between an EphA2 receptor and an ephrin ligand can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein (e.g., an EphA2 receptor or an ephrin ligand) can be immobilized on a suitable affinity matrix by standard techniques, such as chemical cross-linking, or via an antibody raised against the isolated or purified protein, and bound to a solid support. The matrix can be packed in a column or other suitable container and is contacted with one or more agents (e.g., a mixture) to be tested under conditions suitable for binding of the agent to the protein. For example, a solution containing an agent having formula (I) can be made to flow through the matrix. The matrix can be washed with a suitable wash buffer to remove unbound agents and non-specifically bound agents. Agents which remain bound can be released by a suitable elution buffer. For example, a change in the ionic strength or pH of the elution buffer can lead to a release of agents. Alternatively, the elution buffer can comprise a release component or components designed to disrupt binding of agents (e.g., one or more ligands or receptors, as appropriate, or analogs thereof which can disrupt binding or competitively inhibit binding of test agent to the protein).

In other embodiments, other assays can be used for screening for effective agents that stimulate functions (e.g., phosphorylation or dimerization) of EphA2. Methods of detecting protein phosphorylation and dimerization can be achieved by techniques such as immunoprecipitations, Western blots, and cross-linking assays. In these cases, antibodies may be used in a variety of detection techniques. Detailed methods have been described in the working examples.

In certain embodiments, the invention relates to methods for selecting or screening for a small molecule agent having formula (I) capable of binding to an EphA2 receptor. The compound may be optionally derivatized with another compound. One advantage of this modification is that the derivatizing compound may be used to facilitate the EphA2/agent complex collection, e.g., after separation of compound and an EphA2 receptor. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof.

Methods of Treatment

The present invention provides methods of treating an individual suffering from cancer through administering to the individual a therapeutically effective amount of an EphA2 agonist compounds described herein. The present invention provides methods of preventing or reducing the onset of cancer in an individual through administering to the individual an effective amount of an EphA2 agonist compounds. These methods are particularly aimed at therapeutic and prophylactic treatments of animals, and more particularly, humans.

In some embodiments, the therapeutically effective amount of a small molecule agonist of EphA2 receptor is the amount effective to activate and internalize EphA2 receptors in cancer cells of the subject. In some embodiments, the therapeutically effective amount of a small molecule agonist of EphA2 receptor is the amount effective to inhibit tumor growth associated with EphA2 tumorgenesis in the subject.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

Cancers and related disorders that can be treated, prevented, or managed by methods including the administration of EphA2 agonist compounds described herein include but are not limited to cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Accordingly, the methods and EphA2 agonist compounds described herein are also useful in the treatment or prevention of a variety of cancers or other abnormal proliferative diseases, including (but not limited to) the following: carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, rectum, breast, prostate, bladder, kidney, pancreas, ovary, or uterus. In other specific embodiments, sarcoma, melanoma, or leukemia is treated or prevented.

In some embodiments, the cancer is malignant and overexpresses EphA2. In other embodiments, the disorder to be treated is a pre-cancerous condition associated with cells that overexpress EphA2. In specific embodiments, the pre-cancerous condition is high-grade prostatic intraepithelial neoplasia (PIN), fibroadenoma of the breast, fibrocystic disease, or compound nevi.

In certain embodiments, EphA2 agonist compounds described herein can be delivered to cancer cells by site-specific means. Cell-type-specific delivery can be provided by conjugating a therapeutic agent to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In certain embodiments, one or more EphA2 agonist compounds can be administered, together (simultaneously) or at different times (sequentially). In addition, therapy by administration of one or more EphA2 agonist compounds is combined with the administration of one or more therapies such as, but not limited to, chemotherapies, radiation therapies, hormonal therapies, and/or biological therapies/immunotherapies. Prophylactic/therapeutic agents include, but are not limited to, proteinaceous molecules, including, but not limited to, peptides, polypeptides, proteins, including post-translationally modified proteins, antibodies etc.; or small molecules (less than 2500 daltons), inorganic or organic compounds; or nucleic acid molecules including, but not limited to, double-stranded or single-stranded DNA, or double-stranded or single-stranded RNA, as well as triple helix nucleic acid molecules. Prophylactic/therapeutic agents can be derived from any known organism (including, but not limited to, animals, plants, bacteria, fungi, and protista, or viruses) or from a library of synthetic molecules.

In a specific embodiment, the methods encompass administration of an EphA2 agonist compound having formula (I) in combination with the administration of one or more prophylactic/therapeutic agents that are inhibitors of kinases such as, but not limited to, ABL, ACK, AFK, AKT (e.g., AKT-1, AKT-2, and AKT-3), ALK, AMP-PK, ATM, Auroral, Aurora2, bARKI, bArk2, BLK, BMX, BTK, CAK, CaM kinase, CDC2, CDK, CK, COT, CTD, DNA-PK, EGF-R, ErbB-1, ErbB-2, ErbB-3, ErbB-4, ERK (e.g., ERK1, ERK2, ERK3, ERK4, ERK5, ERK6, ERK7), ERT-PK, FAK, FGR (e.g., FGF1R, FGF2R), FLT (e.g., FLT-1, FLT-2, FLT-3, FLT-4), FRK, FYN, GSK (e.g., GSK1, GSK2, GSK3-alpha, GSK3-beta, GSK4, GSK5), G-protein coupled receptor kinases (GRKs), HCK, HER2, HKII, JAK (e.g., JAKI, JAK2, JAK3, JAK4), JNK (e.g., JNK1, JNK2, JNK3), KDR, KIT, IGF-1 receptor, IKK-1, IKK-2, INSR (insulin receptor), IRAK1, IRAK2, IRK, ITK, LCK, LOK, LYN, MAPK, MAPKAPK-1, MAPKAPK-2, MEK, MET, MFPK, MHCK, MLCK, MLK3, NEU, NIK, PDGF receptor alpha, PDGF receptor beta, PHK, PI-3 kinase, PKA, PKB, PKC, PKG, PRK1, PYK2, p38 kinases, p135tyk2, p34cdc2, p42cdc2, p42mapk, p44 mpk, RAF, RET, RIP, RIP-2, RK, RON, RS kinase, SRC, SYK, S6K, TAK1, TEC, TIE1, TIE2, TRKA, TXK, TYK2, UL13, VEGFR1, VEGFR2, YES, YRK, ZAP-70, and all subtypes of these kinases (see e.g., Hardie and Hanks (1995) The Protein Kinase Facts Book, I and II, Academic Press, San Diego, Calif.). In other embodiments, an EphA2 agonist compound is administered in combination with the administration of one or more prophylactic/therapeutic agents that are inhibitors of Eph receptor kinases (e.g., EphA2, EphA4). In still another embodiment, an EphA2 agonist compound is administered in combination with the administration of one or more prophylactic/therapeutic agents that are inhibitors of EphA2.

In another specific embodiment, the methods of the invention encompass administration of EphA2 agonist compounds in combination with the administration of one or more prophylactic/therapeutic agents that are angiogenesis inhibitors such as, but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-.beta.); Vasculostatin; Vasostatin (calreticulin fragment); ZD6126; ZD6474; farnesyl transferase inhibitors (FTI); and bisphosphonates.

In another specific embodiment, the methods of the invention encompass administration of EphA2 agonist compounds in combination with the administration of one or more prophylactic/therapeutic agents that are anti-cancer agents such as, but not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3,5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogens, antiestrogens, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflomithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1 based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, R11 retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer. Preferred additional anti-cancer drugs are 5-fluorouracil and leucovorin.

In more particular embodiments, the present invention also comprises the administration of one or more EphA2 therapeutic agents in combination with the administration of one or more therapies such as, but not limited to anti-cancer agents such as those disclosed.

The invention also encompasses administration of the EphA2 therapeutic agents in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the Physician's Desk Reference (66th ed., 2012).

In one specific embodiment, patients with breast cancer can be administered an effective amount of an EphA2 agonist compound described herein. In another embodiment, the EphA2 agonist compounds can be administered in combination with an effective amount of one or more other agents useful for breast cancer therapy including but not limited to: doxorubicin, epirubicin, the combination of doxorubicin and cyclophosphamide (AC), the combination of cyclophosphamide, doxorubicin and 5-fluorouracil (CAF), the combination of cyclophosphamide, epirubicin and 5-fluorouracil (CEF), herceptin, tamoxifen, the combination of tamoxifen and cytotoxic chemotherapy, taxanes (such as docetaxel and paclitaxel). In a further embodiment, EphA2 agonist compounds can be administered with taxanes plus standard doxorubicin and cyclophosphamide for adjuvant treatment of node-positive, localized breast cancer.

In another specific embodiment, patients with pre-cancerous fibroadenoma of the breast or fibrocystic disease can be administered EphA2 agonist compounds to treat the disorder and decrease the likelihood that it will progress to malignant breast cancer. Additionally, patients refractory to treatment, particularly hormonal therapy, more particularly tamoxifen therapy, can be administered EphA2 agonist compounds to treat the cancer and/or render the patient non-refractory or responsive.

In another embodiment, patients with colon cancer can be administered an effective amount of one or more EphA2 agonist compounds. In yet another embodiment, EphA2 therapeutic agents can be administered in combination with an effective amount of one or more other agents useful for colon cancer therapy including but not limited to: the combination of 5-FU and leucovorin, the combination of 5-FU and levamisole, irinotecan (CPT-11) or the combination of irinotecan, 5-FU and leucovorin (IFL).

In other embodiments, patients with prostate cancer can be administered an effective amount of one or more EphA2 agonist compounds. In another embodiment, the EphA2 agonist compounds can be administered in combination with an effective amount of one or more other agents useful for prostate cancer therapy including but not limited to: external-beam radiation therapy, interstitial implantation of radioisotopes (i.e., $I^{125}$, palladium, iridium), leuprolide or other LHRH agonists, non-steroidal antiandrogens (flutamide, nilutamide, bicalutamide), steroidal antiandrogens (cyproterone acetate), the combination of leuprolide and flutamide, estrogens such as DES, chlorotrianisene, ethinyl estradiol, conjugated estrogens U.S.P., DES-diphosphate, radioisotopes, such as strontium-89, the combination of external-beam radiation therapy and strontium-89, second-line hormonal therapies such as aminoglutethimide, hydrocortisone, flutamide withdrawal, progesterone, and ketoconazole, low-dose prednisone, or other chemotherapy regimens reported to produce subjective improvement in symptoms and reduction in PSA level including docetaxel, paclitaxel, estramustine/docetaxel, estramustine/etoposide, estramustine/vinblastine, and estramustine/paclitaxel.

In a specific embodiment, patients with pre-cancerous high-grade prostatic intraepithelial neoplasia (PIN) are administered an EphA2 agonist compounds to treat the disorder and decrease the likelihood that it will progress to malignant prostate cancer.

In specific embodiments, patients with melanoma are administered an effective amount of EphA2 agonist compounds described herein. In another embodiment, the EphA2 agonist compounds can be administered in combination with an effective amount of one or more other agents useful for melanoma cancer therapy including but not limited to: dacarbazine (DTIC), nitrosoureas such as carmustine (BCNU) and lomustine (CCNU), agents with modest single agent activity including vinca alkaloids, platinum compounds, and taxanes, the Dartmouth regimen (cisplatin, BCNU, and DTIC), interferon alpha (IFN-A), and interleukin-2 (IL-2). In a specific embodiment, an effective amount of one or more EphA therapeutic agents can be administered in combination with isolated hyperthermic limb perfusion (ILP) with melphalan (L-PAM), with or without tumor necrosis factor-alpha (TNF-alpha) to patients with multiple brain metastases, bone metastases, and spinal cord compression to achieve symptom relief and some shrinkage of the tumor with radiation therapy.

In a specific embodiment, patients with pre-cancerous compound are administered EphA2 agonist compounds to treat the disorder and decrease the likelihood that it will progress to malignant melanoma.

In specific embodiments, patients with ovarian cancer are administered an effective amount of one or more EphA2 agonist compounds. In another embodiment, the EphA2 agonist compounds can be administered in combination with an effective amount of one or more other agents useful for ovarian cancer therapy including but not limited to: intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. It is contemplated that an effective amount of one or more EphA2 therapeutic agents can be administered in combination with the administration Taxol for patients with platinum-refractory disease. Included is the treatment of patients with refractory ovarian cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

In specific embodiments, patients with small lung cell cancer are administered an effective amount of one or more EphA2 agonist compounds. In another embodiment, the antibodies of the invention can be administered in combination with an effective amount of one or more other agents useful for lung cancer therapy including but not limited to: thoracic radiation therapy, cisplatin, vincristine, doxorubicin, and etoposide, alone or in combination, the combination of cyclophosphamide, doxorubicin, vincristine/etoposide, and cisplatin (CAV/EP), local palliation with endobronchial laser therapy, endobronchial stents, and/or brachytherapy.

In other specific embodiments, patients with non-small lung cell cancer are administered an effective amount of one or more EphA2 therapeutic agents in combination with an effective amount of one or more other agents useful for lung cancer therapy including but not limited to: palliative radiation therapy, the combination of cisplatin, vinblastine and mitomycin, the combination of cisplatin and vinorelbine, paclitaxel, docetaxel or gemcitabine, the combination of carboplatin and paclitaxel, interstitial radiation therapy for endobronchial lesions or stereotactic radiosurgery.

Administration and Pharmaceutical Compositions

EphA2 agonist compounds described herein can be administered in various forms, depending on the disorder to be treated and the age, condition, and body weight of the patient, as is well known in the art. For example, where the compounds can be formulated in a pharmaceutical composition with a pharmaceutically acceptable carrier. When administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the EphA2 agonist compounds that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of a therapeutic agent as an active ingredient. A compound may also be administered as a bolus, electuary or paste.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

The therapeutic agent can be alternatively administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the therapeutic agent across the skin. The rate of such flux can be controlled by either providing a rate controlling membrane or dispersing the peptidomimetic in a polymer matrix or gel.

Pharmaceutical compositions for parenteral administration can include one or more EphA2 agonist compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of subject therapeutic agent in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the EphA2 agonist compounds are administered as pharmaceuticals to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories.

These EphA2 agonist compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The invention now being generally described, it will be more readily understood by reference to the following examples which are included merely for purposes of illustration of certain aspects and embodiments of the present invention, and are not intended to limit the invention.

EXAMPLE 1

Characterization of Doxazosin as an EphA2 Agonist

We have sought to identify small molecule agonists using a combination of structure-based virtual screening and cell based assays. We report the discovery and characterization of doxazosin as a novel agonist for EphA2 and EphA4. Moreover, in a newly established orthotopic xenograft model of metastatic prostate cancer, systemic administration of doxazosin significantly suppressed distal metastasis and prolonged overall survival. To our knowledge, this is the first example of a small molecule RTK agonist with anti-cancer efficacy in vitro and in vivo.

Materials and Methods

Cell Lines and Reagents

Doxazosin, Labetalol, Dobutamine, and Phenoxybenzamine were all purchased from SIGMA. Other compounds from the virtual screening high scoring list were obtained from Butt Park, Ltd and Chembridge Corporation. Ephrin-A1-Fc, ephrin-B1-Fc, ephrin-A5-Fc and rabbit anti-pEphA/B antibody were produced as described previously. Sources of antibodies include Santa Cruz Biotechnology (rabbit polyclonal anti-EphA2 and anti-ERK1, mouse anti-pERK1/2), Cell Signaling Technologies (antipS473-Akt and anti-Akt), R&D Systems (goat anti EphA1, -EphA3, -EphA4, -EphB3 antibodies) and Millipore [mouse monoclonal EphA2 (clone D7)]. Rabbit polyclonal anti-EphB3 antibody was a gift from Dr. Elena Pasquale. All cell lines HEK 293, MDA-MB-231, A172 and PC-3 were purchased from ATCC. PC-3-DAB2IP shRNA knockdown cells were established and described. Cells were maintained in either Dulbecco's Modified Eagle Medium (DMEM), or RPMI 1640 (PC-3 and PC3-DAB2IP KD) supplemented with 10% FBS, 10 mg/ml glutamine, 100 U/ml penicillin, and 0.1 mg/ml streptomycin.

In Silico Screening of Compounds

For in silico screening we have used compounds from the NCI database (~250000 compounds), Sigma database of rare chemicals (~100000 compounds) and Available Chemical Directory (ACD) (http://mdl.com) (~350,000 commercially available). A total of ~700,000 molecules were preprocessed before docking using the FILTER utility from the OpenEye software package (http://eyesopen.com) in order to eliminate toxic or reactive chemicals and molecules without drug-like properties. This left about 100,000 compounds for which multiple conformations were generated using the OMEGA utility (OpenEye) for rigid docking. The Gasteiger-Marsili atomic charges were assigned using BABEL freeware utility. The 3D structure of the EphA2 receptor ligand binding domain was obtained by homology modeling as described previously.

The in silico screening was done using DOCK5.1 software. DOCK5.1 implements a geometry-based approach for the docking of the small ligands. Connolly molecular surface of the EphA2 receptor structure was calculated using a probe radius of 1.4 Å. The negative image of the binding site was created using the SPHGEN module, which generates the spheres of a certain radii and calculates the best match of these spheres with the molecular surface of the protein docking site. The DOCK module was used to fit the small molecules from the database to the centers of these spheres and the best obtained configurations were scored in terms of energy using the AMBER force field. The virtual screening was carried out on Beowulf cluster of Linux machines at the Ohio Supercomputer Center.

Surface Plasmon Resonance Analysis

Binding analysis was carried out using standard biosensor chips and the SR7000DC Dual Channel SPR System (Reichert Life Sciences, Depew, NY). The extracellular domain (ECD) of EphA2 was coupled to the chip by standard amine coupling using 1-ethyl-3-(3-dimethylaminopropyl) carbodiimide (EDC) and N-hydroxysuccinimide (NHS), followed by ethanolamine wash. In the case of doxazosin, Neutravidin was coupled to the chip, followed by ethanolamine wash and addition of minimally biotinylated EphA2 ECD to properly orient the protein. Different concentrations of dobutamine, labetalol, and doxazosin in running buffer (PBS, 0.05% Tween-20, 1% DMSO) were flown over the chip at a rate of 75-90 ml/min and binding analyzed in real-time. After approximately 60 seconds, running buffer was flown over the chip to dissociate the compounds from the coupled protein (downward slope of curve). Binding data were analyzed and KD values determined using Clamp software (BioLogic Software Pty Ltd).

Cell Stimulation, Immunoprecipitation, Immunoblotting, and Immunofluorescence Staining Cells were plated in 24-well dishes at a density of 100,000 cells/well and grown for 24 hours prior to stimulation with appropriate compounds and ephrins for the given amounts of time. Compounds were prepared in DMSO at 500 times the final concentrations and 0.2% DMSO was used as vehicle control. Following treatment, cells were lysed directly in SDS Gel Loading Buffer and immunoblotted as described previously. Immunoprecipitation and immunofluorescence staining was performed as described. For immunoprecipitation, 300,000 cells/well were plated in 6-well dishes and lysed in modified RIPA Buffer (20 mM Tris-HCl pH 7.4, 20 mM NaF, 150 mM NaCl, 10% glycerol, 0.1% SDS, 0.5% DCA, 2 mM EDTA, 1% Triton X-100) following treatment. Either 10 μg of ephrin-A1-Fc, or 4 mg of EphA2 mouse monoclonal antibody (Clone D7, Millipore) were used, and mouse IgG was used as a negative control for EphA2 IP.

ITC and NMR Characterization of the Binding of the EphA4 LBD with Doxazosin

Production of the 181-residue EphA4 ligand binding domain (LBD, residues 29-209) and isothermal titration calorimetry (ITC) experiments were performed as previously described. To characterize the binding of the EphA4 LBD and doxazosin by NMR, two-dimensional $^1$H-$^{15}$N HSQC spectra of the $^{15}$N-labeled EphA4 LBD were acquired at 25° C. with a protein concentration of 100 μM in the absence and presence of Doxazosin at molar ratios of 1:1; 1:2, 1:4, 1:5 and 1:6 (EphA4/DZ). By superimposing HSQC spectra, the shifted HSQC peaks could be identified and further assigned to the corresponding residues of the EphA4 ectodomain. The degree of perturbation was measured by an integrated chemical shift index (CSI) calculated by the formula $[(\Delta H)^2 + (\Delta N)^2/5]^{1/2}$.

In Vivo Metastasis Assay

PC-3 cells (from ATCC) engineered to express both GFP and DAB2IP shRNA were characterized previously. Cells were suspended in serum free medium and 2,000 cells injected directly into the prostate glands of 7 week old NCr athymic nu/nu mice. Three days after injection, mice were divided into two groups, one receiving vehicle alone (5% DMSO/10% Cremophor/PBS) and another 50 mg/kg doxazosin via intraperitoneal injection daily for 10 days. Mice were sacrificed 14 days later and intact primary tumors were imaged under a UV light box with a Digital camera. Lungs were dissected into separate lobes and GFP-expressing metastases were imaged using an inverted fluorescent microscope (Leica). Metastases were enumerated in the two largest lung lobes and placed into size categories based upon their diameters, measured in number of cells (1-10 cells). Total metastatic burden was calculated in each mouse using the following equation: [burden=Σ (# of foci×focus diameter)].

Statistical Analyses

Significance of results was determined using Student's two-tailed t-test. Differences were considered significant when P≤0.05.

Results

Structure-Based Virtual Screening and Cell-Based Assays Identifies Doxazosin as an Agonist Capable of Inducing Catalytic Activation of EphA2 Receptor Tyrosine Kinase To identify small molecule agonists for EphA2, we took a structure-based in silico screening approach. Our molecular modeling of the EphA2 ligand-binding domain (LBD) based on the crystal structure of the EphB2 LBD revealed that the binding pocket of EphA2 can incorporate up to 4 amino acids, suggesting that it could accommodate small molecules with a molecular weight (MW) of about 500 Dalton. This notion was confirmed recently by determination of the crystal structure of the EphA2/ephrin-A1 complex (FIG. 1B). The size falls in the range of common drugs, making EphA2 LBD a desirable target for drug discovery. Toward this end, we initiated in silico screening to search for small molecules that interact favorably with the ligand-binding pocket of EphA2 derived from molecular modeling before the crystal structure became available. Multiple conformations for each structure were generated with OMEGA (OpenEye) and each conformation was docked individually using DOCK. Our initial screening of over 750,000 compounds identified a number of small molecules that could potentially interact with the ligand-binding pocket. The commercially available top-scoring compounds were screened for their ability to induce EphA2 activation in MDAMB-231 breast cancer cells. Because MDA-MB-231 cells express endogenous EphA2 as well as other Eph receptors, including EphA1, we overexpressed EphA2 in order to minimize the contribution from other Eph receptors in our analysis. The cells were stimulated with the compounds at 50 mM. Total cell lysates were probed with a previously described antibody that recognizes the activated Eph receptors. FIG. 1C shows the results from a representative subset of compounds with structures. Among the small molecules tested, compound 11, or doxazosin, activated EphA2 to the greatest extent.

Originally developed as an antagonist for α1-adrenoreceptor, doxazosin (FIG. 1D) is an FDA-approved drug (CARDURA) for treating hypertension and benign prostate hyperplasia (BPH). To confirm specific EphA2 activation by doxazosin, we analyzed levels of activated Eph receptor in MDA-231-A2 cells following treatment with multiple doses of doxazosin and EphA2 immunoprecipitation. Doxazosin activated EphA2 receptor in a dose-dependent manner Activation was detectable at 25 mM and became stronger at 50 mM or higher (FIG. 1E). Similar to the native ligands, there was also degradation of EphA2 following exposure to high doses of doxazosin, which is characteristic of most RTKs upon ligand induced activation including Ephs.

Doxazosin Induces Catalytic Activation of EphA2 Independent of α1-Adrenoreceptor Antagonism Because doxazosin is a well-characterized antagonist of α1-adrenoreceptor, a question arose whether EphA2 catalytic activation by doxazosin might be due to an indirect effect of its α1-adrenoreceptor antagonism. To address this question, we pretreated MDA-231-A2 cells with the well-characterized irreversible α1-adrenoreceptor inhibitor, phenoxybenzamine and then assayed for induction of EphA2 phosphorylation by doxazosin. MDA-231-A2 cells were chosen because they have previously been shown to express both α1a and α1b-adrenoreceptors. No difference in EphA2 activation by doxazosin was observed following phenoxybenzamine pretreatment versus no pretreatment (FIG. 1F), demonstrating that doxazosin directly activates EphA2 independent of its α1-adrenoreceptor antagonism.

Two other top-scoring compounds, dobutamine and labetalol (Compounds 9 and 10), function as a β1-adrenoreceptor agonist and an α/β-adrenoreceptor antagonist, respectively. Treatment with dobutamine failed to activate EphA2 up to 500 mM, while labetalol failed to activate even at 500 mM, confirming that doxazosin is indeed more potent and that activation is not a direct result of general adrenoreceptor binding.

Doxazosin Directly Interacts with the EphA2 LBD

Because doxazosin was discovered via virtual screening targeting the ligand binding pocket of EphA2, it was expected to directly bind to the domain. To test this, binding of doxazosin to the previously described recombinant LBD of EphA2 was analyzed using Surface Plasmon Resonance (SPR). We found that doxazosin directly bound to the EphA2 LBD with a dissociation constant (KD) of 47.6 mM (FIG. 1G). Binding of both dobutamine and labetalol was also tested and shown to occur with much lower affinity than doxazosin (KD=1.5 mM and 0.44 mM, respectively). Taken together, these results demonstrate that doxazosin directly binds to the EphA2 LBD. Upon the recent determination of the X-ray crystal structure of the EphA2-LBD in complex with ephrin-A1, we compared it with the homology model of EphA2 used in the original screening. Despite some expected differences, the EphA2 binding site of the homology model was overall similar to the one in the crystal structure, supporting general validity of the molecular model for the virtual screening. Next, we repeated the docking of doxazosin into the ligand binding site from the EphA2 crystal structure. FIG. 1H shows doxazosin docked into the EphA2 crystal structure, in an orientation similar to that in the NMR structure of the EphA2-doxazosin complex. A new round of virtual screening was also conducted using the EphA2 LBD crystal structure. However, of the 30 new top-scoring compounds tested, we did not find agonists that displayed better activities than doxazosin.

Doxazosin Activates EphA2 Receptor in Different Cell Types

To determine whether the EphA2 agonist activity of doxazosin is cell-context specific, we evaluated the effects of doxazosin on additional cell types. We first utilized HEK 293 cells overexpressing EphA2 (HEK 293-A2) that we described previously. HEK 293 cells express low levels of endogenous EphA receptors; overexpression of EphA2 in these cells allows further demonstration of specific activation of the exogenous kinase. Similar to MDA-231-A2 cells, significant activation of EphA2 was seen in HEK 293-A2 cells upon treatment with doxazosin starting at 25 µM (FIG. 2A). Next we tested PC-3 cells that express high levels of endogenous EphA2 receptor. Doxazosin also activated endogenous EphA2 in PC-3 cells, although it was not evident until 50 µM. The different kinetics among these cell types may be due, in part, to the different expression levels of EphA2 in the three different cell lines or the specific cellular context. In addition, EphA2 activation in PC-3 cells further supports the α1-adrenoreceptor-independent mechanism, as these cells lack detectable α1a-adrenoreceptor expression. We next evaluated the time-course of activation in both MDA-231-A2 and HEK 293-A2 cells upon treatment with a single 50 µM dose of doxazosin. Significant EphA2 activation could be detected as early as 5 min after treatment in the MDA-231-A2 cell line, which peaked around 30 min (FIG. 2B). EphA2 activation also became evident after 10 min treatment with doxazosin in HEK 293-A2 cells, although it followed a slower kinetics.

Doxazosin Preferentially Activates EphA2 and EphA4 Kinases

There are 14 mammalian Eph receptors that share significant sequence homology. This led us to investigate whether doxazosin may also activate other Eph receptors. For this purpose, HEK 293 cell lines overexpressing EphA1, EphA2, EphA3, EphA4, and EphB3 kinases were utilized. We found that doxazosin activated both EphA2 and EphA4 kinases following a similar dose-response relationship (FIG. 2C). However, no activation of EphA1 was seen at the same concentrations, and activation of EphA3 was weak compared to that of EphA2 and EphA4. EphB3 has higher basal levels of activation (FIG. 2C), which was not further activated. In fact, there was a notable decrease in EphB3 activation upon doxazosin exposure. There is also a moderate level of endogenous EphB4 expression in HEK 293 cells; the lack of activated Eph kinase signals following doxazosin exposure in vector control cells indicated that the endogenous EphB4 was not activated either (FIG. 2C). This data shows that doxazosin preferentially activates EphA2 and EphA4 among the various Eph receptors tested.

NMR Structure Reveals Extensive Direct Interactions of Doxazosin with EphA4

The dual selectivity of doxazosin for EphA2 and EphA4 opened up a possibility to investigate the structural basis of the interactions using NMR spectroscopy. Because the EphA2 LBD expressed in *E. coli* was completely insoluble and could not be refolded after repeated attempts, we focused on the interactions of the EphA4 LBD with doxazosin. First, we assessed EphA4 binding to doxazosin by isothermal calorimetry. The dissociation constant ($K_D$) was calculated to be 12.4 µM, similar to that of EphA2/doxazosin interactions measured by SPR (FIG. 1G). Far-UV circular dichroism showed that doxazosin binding induces no significant secondary structure change in the EphA4 LBD.

To characterize the binding interface, we acquired a series of 1H-15N heteronuclear single quantum coherence (HSQC) spectra of the EphA4 LBD upon adding doxazosin at different molar ratios. A gradual addition of doxazosin resulted in progressive shifts of a subset of HSQC peaks (FIG. 3A), consistent with the relatively low affinity interaction. Most of these HSQC peaks did not exhibit further shifts at molar ratios beyond 1:5. Therefore, the chemical shift index (CSI) at this ratio was calculated (FIG. 3B). Upon binding to doxazosin, multiple clusters of residues underwent dramatic shifts. While some of the shifts overlap with the previously described C1 antagonists of EphA4, many of the shifts were unique to doxazosin (FIG. 3B). The additional shifts are distributed over the convex surface of the ephrin-binding channel, including Val72-Cys73-Asn74 on E-strand, Thr104-Leu105-Arg106 on G-strand, Leu166 on K-strand and Ile192-Ala193 on M-strand. The larger contact area may account for the higher affinity of doxazosin for EphA4 than that of C1.

To visualize the EphA4-doxazosin interaction interface, we constructed models of the EphA4-doxazosin complex with the HADDOCK software in combination with CNS, as described previously for the EphA4-C1 complex Doxazosin has extensive interactions with the EphA4 residues on the D-E and J-K loops, as well as contacts with the convex b-strands composed of Val72-Cys73-Asn74, Thr104-Leu105-Arg106 and Ile192-Ala193 (FIGS. 3C, D). FIG. 3E highlights the interactions between the two doxazosin methoxy groups and EphA4 hydrophobic residues Met60 and Ile159. Interestingly, EphA4 has an additional binding pocket characterized by a positively-charged Arg106 that surrounds the electronegative oxygen atoms in benzodioxin and carbonyl groups on doxazosin (FIG. 3D, E, F). Together the structural studies demonstrate direct interactions between EphA4 and doxazosin, and the KD is in similar concentration range required for cellular activation of the receptor (FIG. 2).

Binding to Doxazosin Stabilizes the Backbone of the EphA4 LBD

Recent evidence shows that protein dynamics beyond the static structure play an important role in various biological processes including signal transmission. To gain structural insight on how doxazosin may function as an EphA2 agonist, we characterized the backbone dynamics of the EphA4 LBD in the free state vs. that in complex with doxazosin. Briefly, we measured the backbone $^{15}N$ relaxation data T1, T2 and heteronuclear NOE values, which were then analyzed by "Model-free" formulism. The analysis generated "squared generalized order parameters", $S^2$, which reflect the backbone rigidity on the ps-ns time scale. Increased $S^2$ values for a larger number of residues upon EphA4 binding to doxazosin compared with free EphA4. Many of the residues with significantly higher S2 values were mapped to the backbone of EphA4 (FIG. 3G). This observation indicates that doxazosin stabilized the backbone of the EphA4 LBD on the ps-ns time scale.

Further evidence supporting the stabilization of the EphA4 LBD by doxazosin came from the chemical exchange rate, Rex, that reflects the conformational changes on the ms-ms time scale of individual residues. Many residues across the EphA4 LBD in the free state exhibited significant Rex values, indicating that they undergo extensive conformational changes. By contrast, binding to doxazosin significantly reduced Rex values for most residues, except for Asn74-Val75 and Thr121. The changes in Rex values were then mapped back to the EphA4 structure (FIG. 3H), demonstrating dramatic decreases in conformational changes in the doxazosin-bound vs. free state. In aggregate, our structural analysis and protein dynamics modeling demonstrate that doxazosin causes significant stabilization of the EphA4 LBD, which may contribute to the agonistic functions of doxazosin.

A New Model for the EphA2-Doxazosin Complex Predicts Additional Agonists

Next, we modeled EphA2-doxazosin interactions incorporating the constraints from the EphA4-doxazosin structure. Sequence and structural alignments revealed residues conserved between EphA2 and EphA4 LBDs that showed significant peak shifts in EphA4 upon binding to doxazosin. These correspond to Ile58, Met59, Val69, Cys70, Asn71, Thr101, Val102, Arg103, Arg159, Leu163, Val189 and Ala190 of EphA2. FIG. 3I illustrates the structure of the EphA2-doxazosin complex built with the HADDOCK software. Similar to the EphA4-doxazosin complex, the methoxy groups of doxazosin interact with the hydrophobic surface formed by Ile58, Met59 and Ala158, while Arg103 of EphA2 interacts with the carbonyl group and the oxygen atoms of the benzodioxin part of doxazosin (FIG. 3I). In addition, the benzyl ring of the benzodioxin sits in a hydrophobic cavity of EphA2 mainly constituted by Cys70, Thr101 and Ala190 side chains (FIG. 3I). Remarkably, in the recently determined X-ray co-crystal structure of the EphA2-ephrin-A1 complex, ephrin-A1 also interacts with the hydrophobic pocket and Arg103 of EphA2 (FIG. 1B), suggesting that doxazosin can recapitulate two distinct modes of receptor interactions by the native ligand.

Doxazosin Triggers EphA2-Dependent Inhibition of ERK and Akt Kinase Activities

Activation of EphA2 receptor by ephrin-A1 ligand inhibits both ERK1/2 and Akt kinase activities in most normal cells and a subset of cancer cells. Having demonstrated that doxazosin could mimic ephrin-A1 in binding to and activating EphA2 receptor, we asked whether doxazosin treatment could inhibit ERK1/2 and Akt activation as well. We first tested this by utilizing the A172 glioma cells engineered to overexpress EphA2 receptor (A172-A2). Unlike MDA-MB-231 cells that have activated Ras and are resistant to ephrin-A1-Fc induced inhibition of ERK1/2, A172 cells harbor wild type Ras and exhibit high basal activation levels of ERK1/2 and Akt, which were sensitive to ephrin-A1-induced inhibition (FIG. 4A, far fight lane). Similar to other cell types tested (FIGS. 1 and 2), doxazosin also activated EphA2 on A172 glioma cells in a dose-dependent manner starting around 25 µM (FIG. 4A). Moreover, treatment with 50 µM and 100 µM doxazosin was sufficient to cause significant inhibition of Akt and ERK1/2 activation. The effects on Akt inhibition coincided with EphA2 activation in these cells, and a higher concentration was needed for ERK1/2 inhibition (FIG. 4A). Similar to MDA-231-A2 cells (FIG. 1E), we observed degradation of EphA2 following doxazosin treatment in A172 cells.

While the results above showed that doxazosin treatment could suppress Akt and ERK activation, a key question remained whether this effect results specifically from EphA2 activation. To address this question, we utilized an immortalized liver epithelial cell line, LK133A, isolated from a hepatoma induced by DEN in EphA2 knockout mice. Retroviral vector was used to restore EphA2 expression in these cells (LK133A-A2), and cells transduced with an empty vector were used as control (LK133AVec). FIG. 4B shows that, in the absence of EphA2, neither doxazosin nor ephrin-A1-Fc was able to inhibit ERK and Akt activities in LK133A-Vec cells (FIG. 4B). In fact, there was a notable increase in ERK and Akt activation by doxazosin. Reintroduction of EphA2 expression restored ERK and Akt inhibition not only by ephrin-A1-Fc but also by doxazosin, which was accompanied by EphA2 activation. Similar to our findings in A172-A2 cells, doxazosin inhibited Akt more strongly than ERK1/2 and at a lower dose of doxazosin, again suggesting differential inhibition of these pathways by EphA2. Together, these data demonstrate that the inhibition of Akt and ERK1/2 by doxazosin is dependent on EphA2, and doxazosin is capable of triggering important downstream signaling events in a similar fashion as the native ligand, ephrin-A1.

Doxazosin Stimulates EphA2 Receptor Internalization and Causes Cell Rounding Similar to Ephrin-A1

Similar to other receptor tyrosine kinases, activation of the EphA2 receptor by its ligand, ephrin-A1, results in receptor internalization and eventual degradation. The decreased total level of EphA2 following doxazosin treatment in MDA-231-A2 cells (FIG. 1E), A172 cells (FIG. 4A), and EphA2 KO cells with restored expression (FIG. 4B) suggests that the receptor is also being internalized and degraded. To directly demonstrate this at the cellular level, we used immunofluorescence to monitor localization of EphA2 following doxazosin treatment. This was first performed using the U373 glioma cell line engineered to overexpress EphA2. This cell line spreads well in culture, thereby facilitating immunofluorescence detection of cell surface and intracellular EphA2. Ephrin-A1-Fc was used as a positive control, which induced nearly complete internalization of EphA2 within 60 min (FIG. 5A). Consistent with its agonistic activities, doxazosin also stimulated significant EphA2 internalization (FIG. 5A). We further tested EphA2 internalization by doxazosin in parental MDA-MB-231 cells, and found that two hours of treatment with 50 µM doxazosin caused significant internalization of the endogenous EphA2, as well (FIG. 5B). Together, these data confirm that doxazosin indeed triggers EphA2 receptor internalization in keeping with its agonistic activities.

As we first reported in 2000, EphA2 activation on PC-3 cells by ephrin-A1 induced rapid cell rounding, a phenomenon that is correlated with inhibition of integrin function. To investigate if doxazosin could also recapitulate this aspect of native ligand function, PC-3 cells were stimulated with 50 mM doxazosin and monitored for morphological changes. We found doxazosin also caused rounding of PC-3 cells, which was similar to ephrin-A1, albeit with a slower kinetics (FIG. 5C).

Doxazosin Inhibits Haptotactic and Chemotactic Migration of Multiple Cancer Cell Types One of the well-established functions of Eph receptors is the ligand-dependent repulsive guidance of cell migration. As a ligand-mimicking agonist for EphA2, doxazosin is expected to activate EphA2 on tumor cells and repulse migrating tumor cells in vitro. To test this possibility, we first investigated the effects of doxazosin on integrin-mediated haptotactic cell migration toward fibronectin in a modified Boyden chamber cell migration assay. As shown in FIG. 6, a dose-dependent inhibition of cell migration was observed in MDA-MB-231 breast cancer cells (FIG. 6A), A172-A2 glioma cells (FIG. 6B), as well as PC-3 prostate cancer cells that were rendered highly migratory and metastatic via DAB2IP knockdown, (PC3-DAB2IP KD, see below) (FIG. 6C). The inhibitory effects were observed when doxazosin was presented either in the bottom chamber, or in both top and bottom chambers in the Transwell assay system. Next, we examined chemotactic cell migration toward hepatocyte growth factor (HGF) and found dose-dependent inhibition by doxazosin in all three cell lines as well, albeit to a lesser degree than those observed in the haptotactic migration assay. Therefore, doxazosin can recapitulate a key function attributed to its native ligands, i.e., negative regulation of cell migration.

Systemic Administration of Doxazosin Suppresses Distal Metastasis of Prostate Cancer In Vivo As tumor cell migration is involved at multiple steps leading to distal tumor metastasis, the potent inhibition of cell migration by doxazosin prompted us to examine whether it could have antimetastatic efficacy in vivo. Historically, studies of prostate cancer metastasis in the preclinical setting have been hampered by the lack of human cell lines that can produce significant metastasis in a reproducible manner It was recently reported that knockdown of DAB2IP, a known prostate tumor suppressor gene that is often lost in aggressive prostate cancer patients, confers PC-3 cells highly migratory and metastatic properties in vitro and in vivo. We took advantage of this newly established model system to test how doxazosin can affect metastasis of prostate cancer. To this end, PC3-DAB2IP KD cells were injected orthotopically into the prostate glands of nude mice. Three days later, recipient mice were subject to systemic treatment by daily i.p. injection of either vehicle control, or 50 mg/kg doxazosin for 10 days. Since these cells also expressed green fluorescent protein (GFP), freshly dissected primary tumors could be readily visualized in a GFP light box (FIG. 7A top panels), and distal metastases to lungs and lymph nodes could be observed and quantified under a fluorescent microscope (FIG. 7A lower panels).

Remarkably, doxazosin treatment caused a significant reduction in the number of lung metastases compared to vehicle control (FIG. 7A, B). The sizes of lung metastases were also significantly smaller in doxazosin-treated mice than those from vehicle-treated mice (FIG. 7C). Total metastatic burden, taking into account both numbers and sizes of metastases, was even more significantly reduced in doxazosin-treated mice (FIG. 7D). Tumor cell dissemination to local lymph nodes was also reduced, but not to a significant extent. Consistent with earlier reports doxazosin-treated mice showed no notable side effects; there were no changes in body weight compared with vehicle control (FIG. 7E), nor were there any signs of behavioral abnormalities, suggesting a lack of general toxicity at the dose used. Doxazosin has been previously shown to moderately decrease subcutaneous growth of DU145 and PC-3 cell xenografts independent of a1-adrenoreceptor. However, the direct target of doxazosin was not identified in those studies. A reduction in primary tumor sizes was also observed in doxazosin-treated mice, although the difference was not statistically significant (not shown), suggesting that the dramatically reduced metastasis was unlikely due to the smaller sizes of primary tumors.

Next, we determined whether doxazosin treatment might impact overall survival. Nude mice orthotopically implanted with the PC3-DAP2IP KD cells were treated for 10 days with either doxazosin, or vehicle control and monitored for survival. Consistent with earlier reports, the mice became moribund starting around three weeks after cell implantation. The Kaplan-Meier plot revealed an increase in overall survival of mice treated with doxazosin (70%) compared with vehicle-treated mice (30%) at 27 days after cell implantation (FIG. 7F). Taken together, these preclinical data demonstrate that doxazosin can inhibit metastasis of aggressive prostate cancer from the primary site and improve overall survival in vivo.

EXAMPLE 2

Design and Synthesis of Small Molecule Agonists of EhpA2 Receptor

We optimized Doxazosin to activate EphA2 with higher potency and reduce the original targeting effect of Doxazosin on adrenoceptor. Several new analogs of Doxazosin showed significantly increased potency to activate EphA2 and induce subsequent receptor internalization. A detailed structure-activity relationship (SAR) was summarized based on the diversely modified structures and the activities. One particular compound 27 with a dimeric structure showed superior activity within the new compound pool.

Lead Optimization and Summarization of the SAR

Previous efforts to develop small molecule EphA2 agonist led to the identification of Doxazosin (2-[4-(2,3-Dihydro-1,4-benzodioxine-2-carbonyl)piperazin-1-yl]-6,7-dimethoxy-quinazolin-4-amine), an α1-selective alpha blocker, used to treat high blood pressure and urinary retention associated with benign prostatic hyperplasia (BPH). Doxazosin significantly activated EphA2 at 50 μM in vitro, and inhibited prostate tumor metastasis in the mouse model. Here, a total of 33 new derivatives based on Doxazosin were synthesized using combinatorial chemistry strategy. First, we kept A and B moieties, and changed C moiety systematically (FIG. 26). Subsequently, we synthesized several symmetric molecules with the best C moiety on both sides of the piperazine ring to determine if the whole A and B parts are necessary for the activity, which is adapted from a recent report about a dimeric EphA2 agonist showing promising activity. Based on the symmetric molecular hypothesis, we also designed larger symmetric structures as illustrated by the dimers (FIG. 26). We then modified A moiety to ethoxy, B moiety to substituted amines to generate diverse structures and enrich the SAR for the future structure optimization.

In the newly designed derivatives, we explored other different structures at C domain including aromatic rings and alky groups. For the aromatic rings, we also synthesized extended linkers. The synthesis of C moiety substituted derivatives is illustrated in Scheme 1.

Scheme 1. Synthesis of C moiety substituted Doxazosin analogs

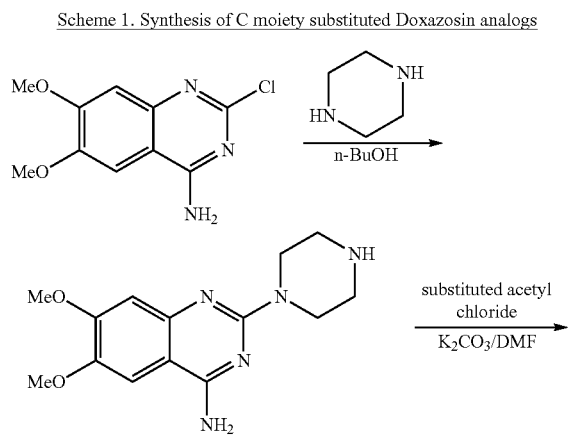

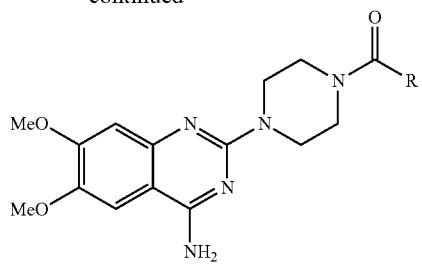

1  R = 2-Naphthyl (72%)
2  R = 4-Biphenyl (73%)
3  R = 5-Benzo[1,3]dioxolyl(71%)
4  R = 4-Methoxy-benzyl (65%)
5  R = 3-Methoxy-benzyl (60%)
6  R = Benzyl (96%)
7  R = 2-Methylnaphthyl (70%)
8  R = 2-Phenylethyl (82%)
9  R = Pyridin-2-yl (42%)
10 R = Pyridin-4-yl (32%)
11 R = 4-Ethyl-phenyl (84%)
12 R = 4-Iodophenyl (85%)
13 R = 4-Nitro-3-chloro-phenyl (91%)
14 R = Methyl (88%)
15 R = Ethyl (63%)
16 R = Propyl(72%)
17 R = Cyclohexanyl (89%)
18 R = 2-Furyl (66%)
19 R = 2-Thiophenyl (56%)
20 R = Isoxazolyl(43%)
21 R = 4-Methoxy-phenyl (85%)
22 R = 4-Bromophenyl (83%)
23 R = Pentyl (73%)
24 R = 1-(benzyloxy)-4-methylbenzyl(89%)

Scheme 2. Synthesis of symmetric structure based on piperazine ring as the core structure

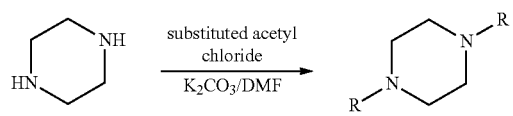

25 R = Methoxy-phenyl (86%)
26 R = 4-Methylsulfane-phenyl (91%)

As illustrated in FIG. 26, we also synthesized dimers with piperazine ring as the core scaffold. A and B whole moiety was replaced by a C moiety structure. The symmetric hypothesis led us to explore the possibility of a bigger dimer based on the whole left domain of the lead compound Doxazosin. Therefore, we synthesized compounds 27 and 28 using different linkers as illustrated in Scheme 3.

Scheme 3. Synthesis of dimer 27 and 28

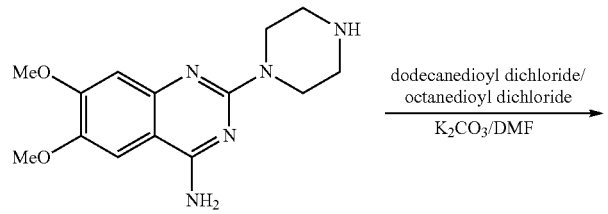

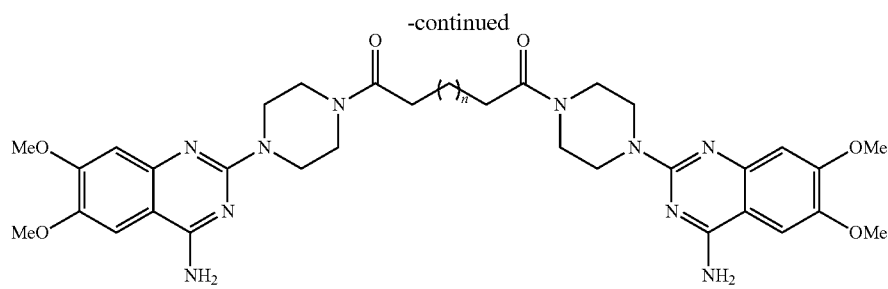

27 n = 8 (68%)
28 n = 4 (77%)

To investigate if the primary amino group on the pyrimidine ring is needed for the activity, we modified the B moiety into different structures. First, we acetylated Doxazosin and compound 24 to generate compounds 29 and 30, respectively (Scheme 4).

Scheme 4. Synthesis of B moiety acetylated analogs

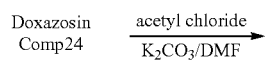

Scheme 5. Synthesis of B moiety modified analogs

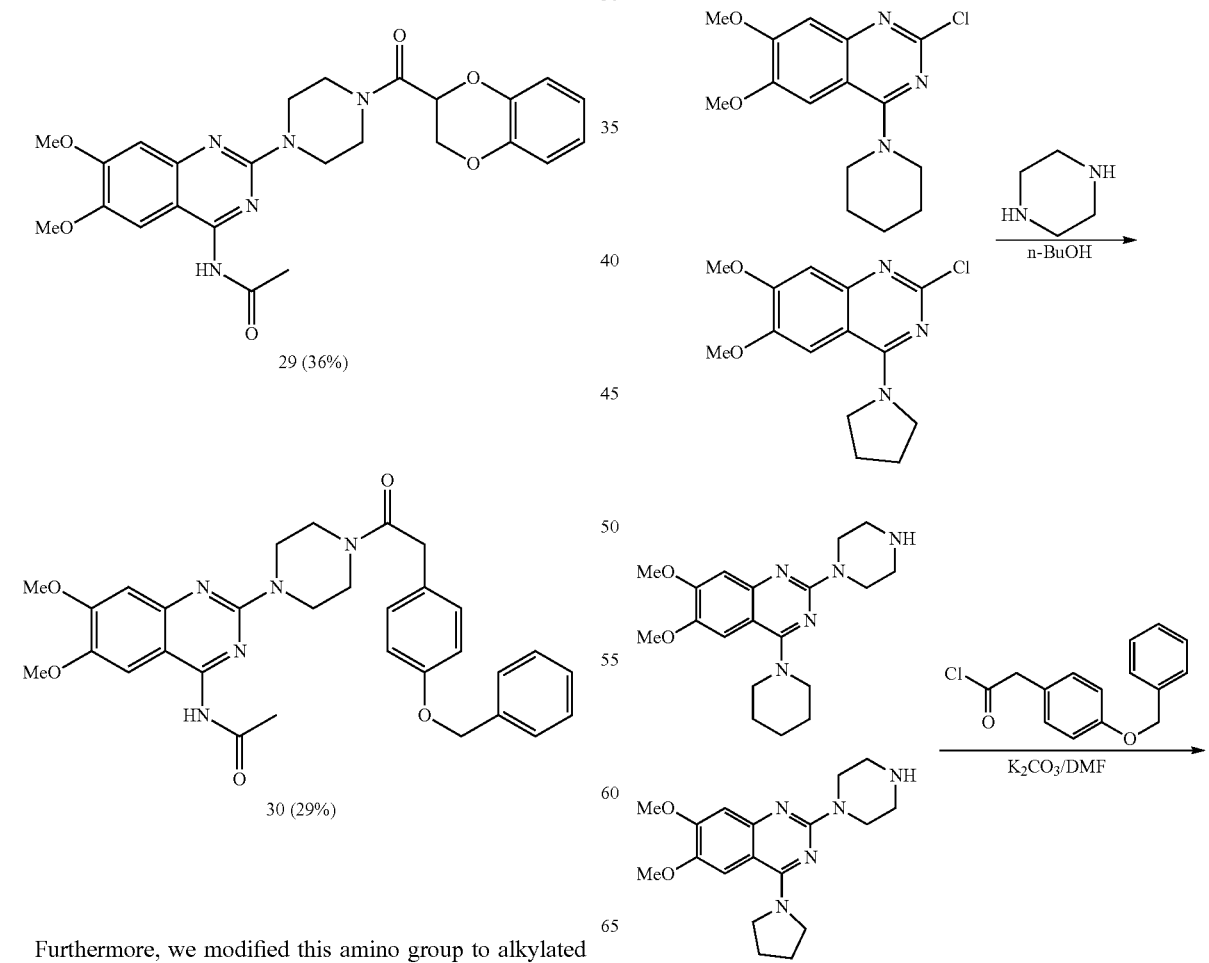

Furthermore, we modified this amino group to alkylated analogs as illustrated in Scheme 5.

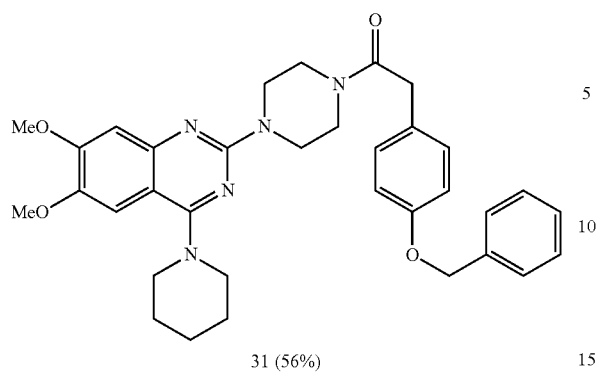

31 (56%)

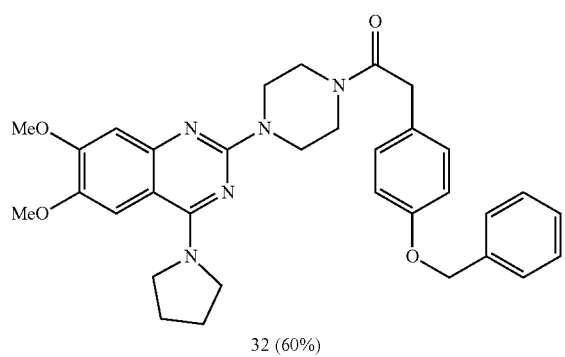

32 (60%)

At last, we modified A moiety to ethoxy group to examine if methoxy is required for the activity. The synthesis is illustrated in Scheme 6.

Scheme 6. Synthesis of A moiety modified analog

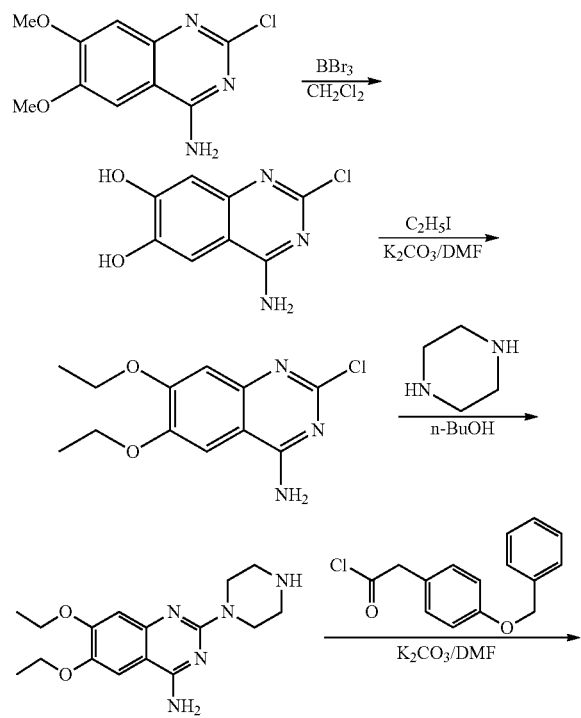

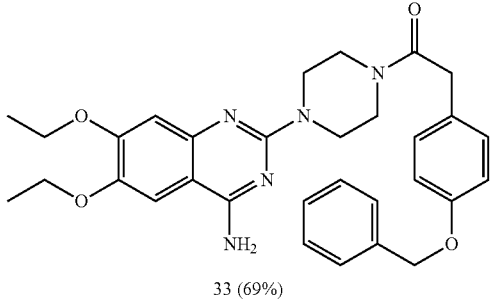

33 (69%)

The 33 new analogs show diverse substitution on the three identified structural moieties, and the biological results of the compounds can provide us a detail SAR to elucidate the structure requirement for the activation of EphA2.

Figure 27:
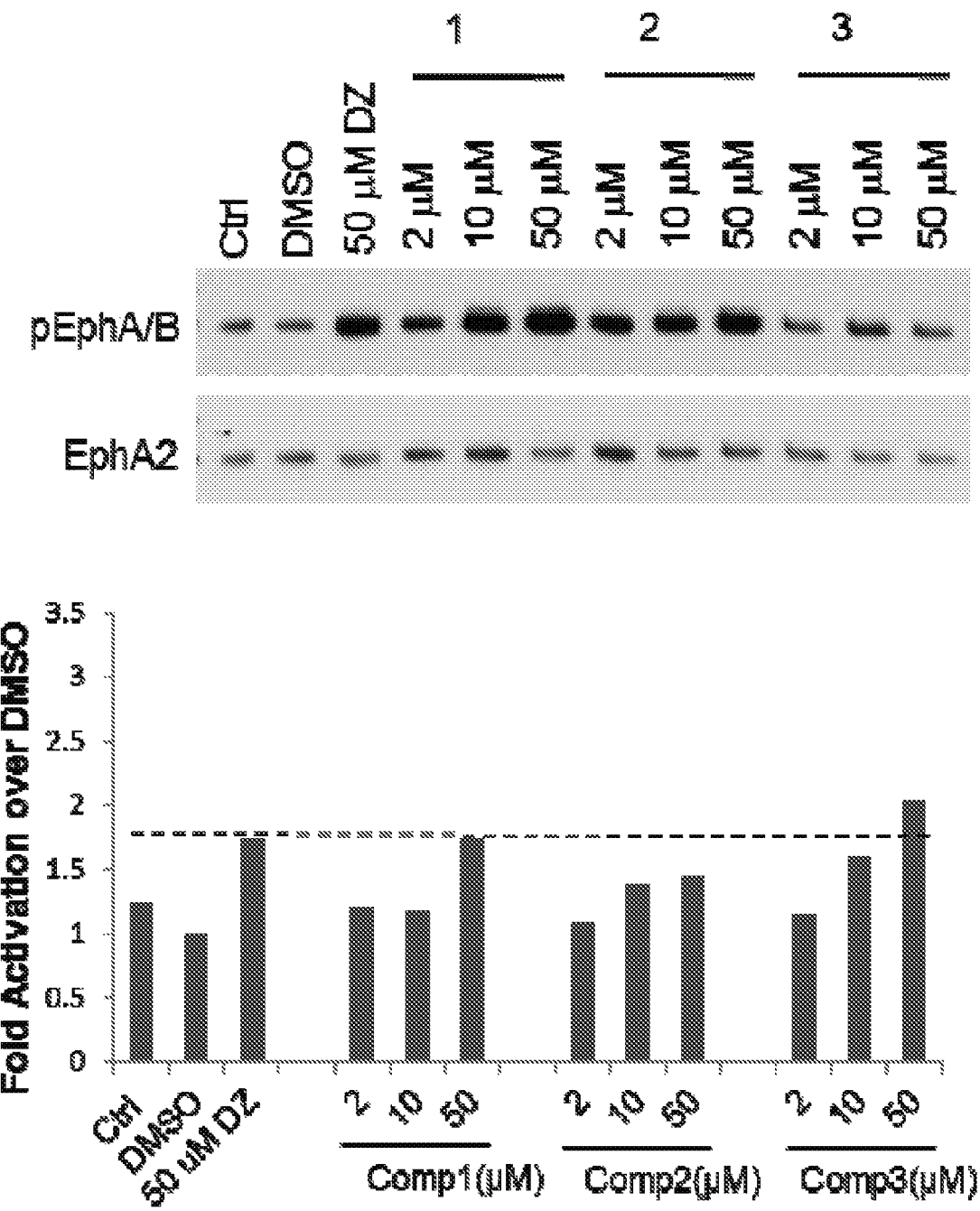
FIG. 27 illustrates EphA2 activation of Doxazosin derivatives in MDA-MB-231-EphA2 cells. Cells were treated with the compounds with three doses (in 0.5% DMSO) for 30 minutes and cell lysates were subject to immunoprecipitation and immunoblot for phosphorylated EphA/B kinases (pEphA/B) and total EphA2. Treatment with 1 μg/ml ephrin-A1-Fc (EA1-Fc) or Doxazosin (DZ) 50 μM were served as positive controls. Treatment with 0.5% DMSO was served as vehicle control.
Figure 27:
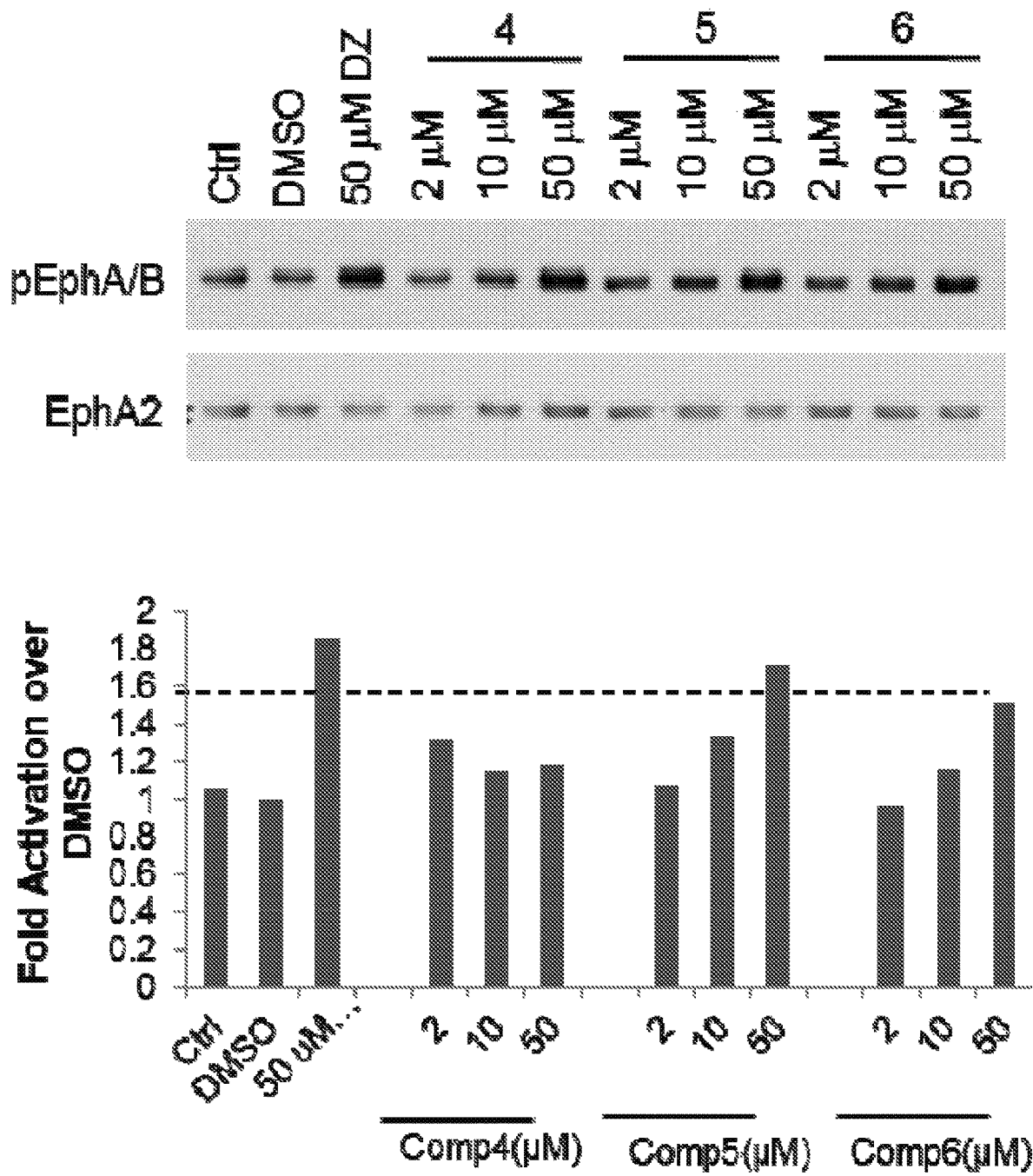
Figure 27:
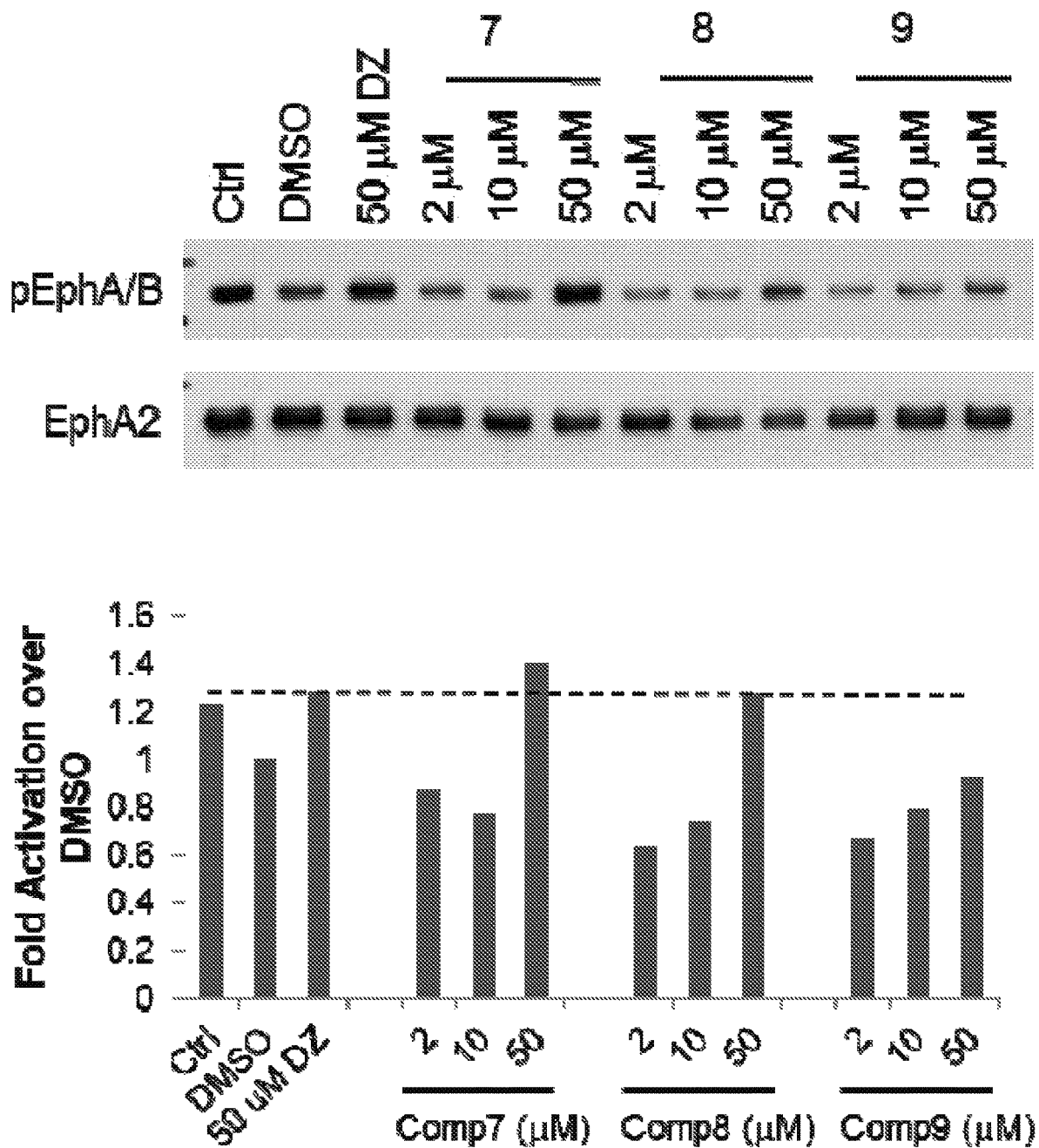
Figure 27:
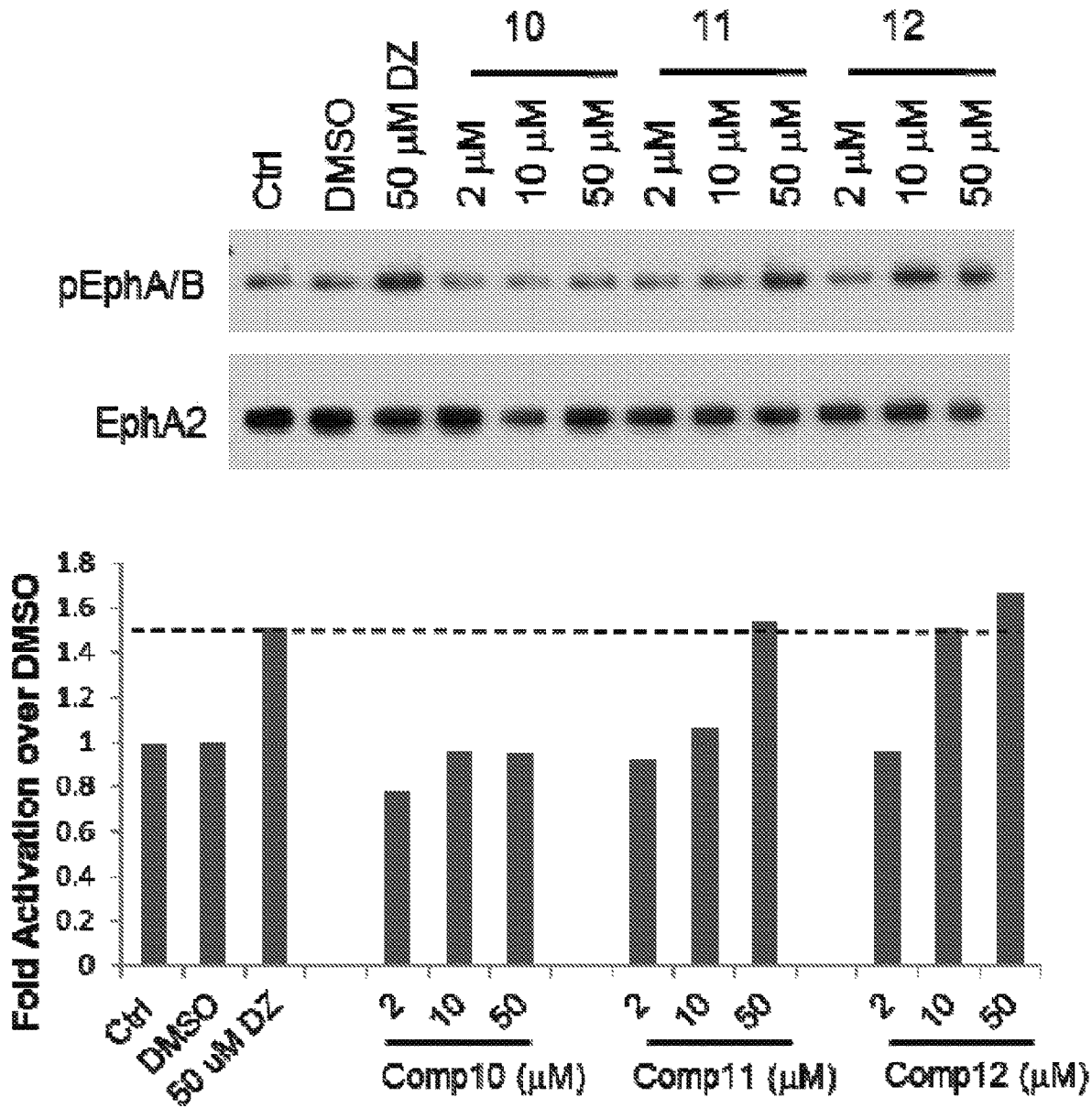
Figure 27:
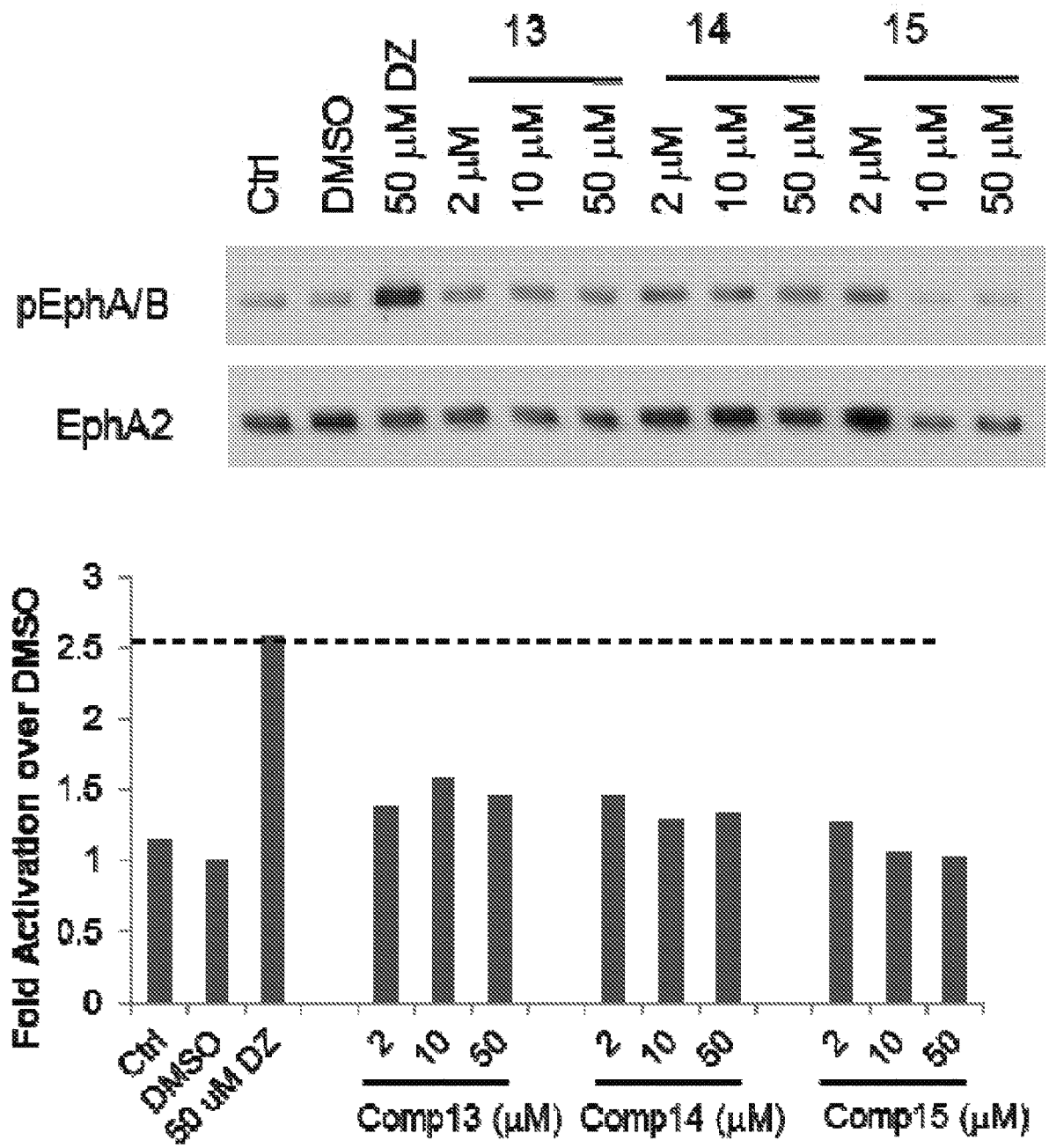
Figure 27:
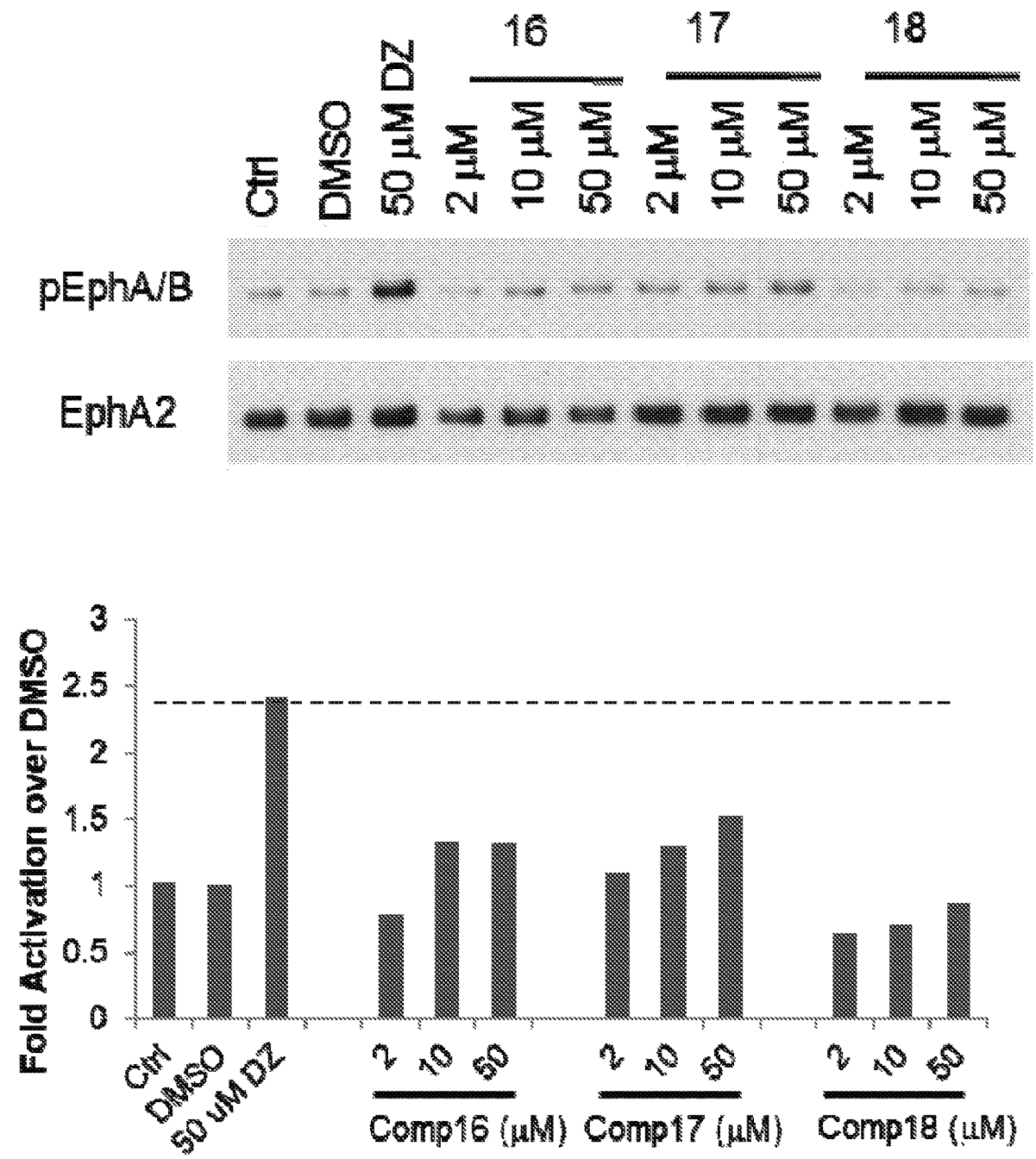
Figure 27:
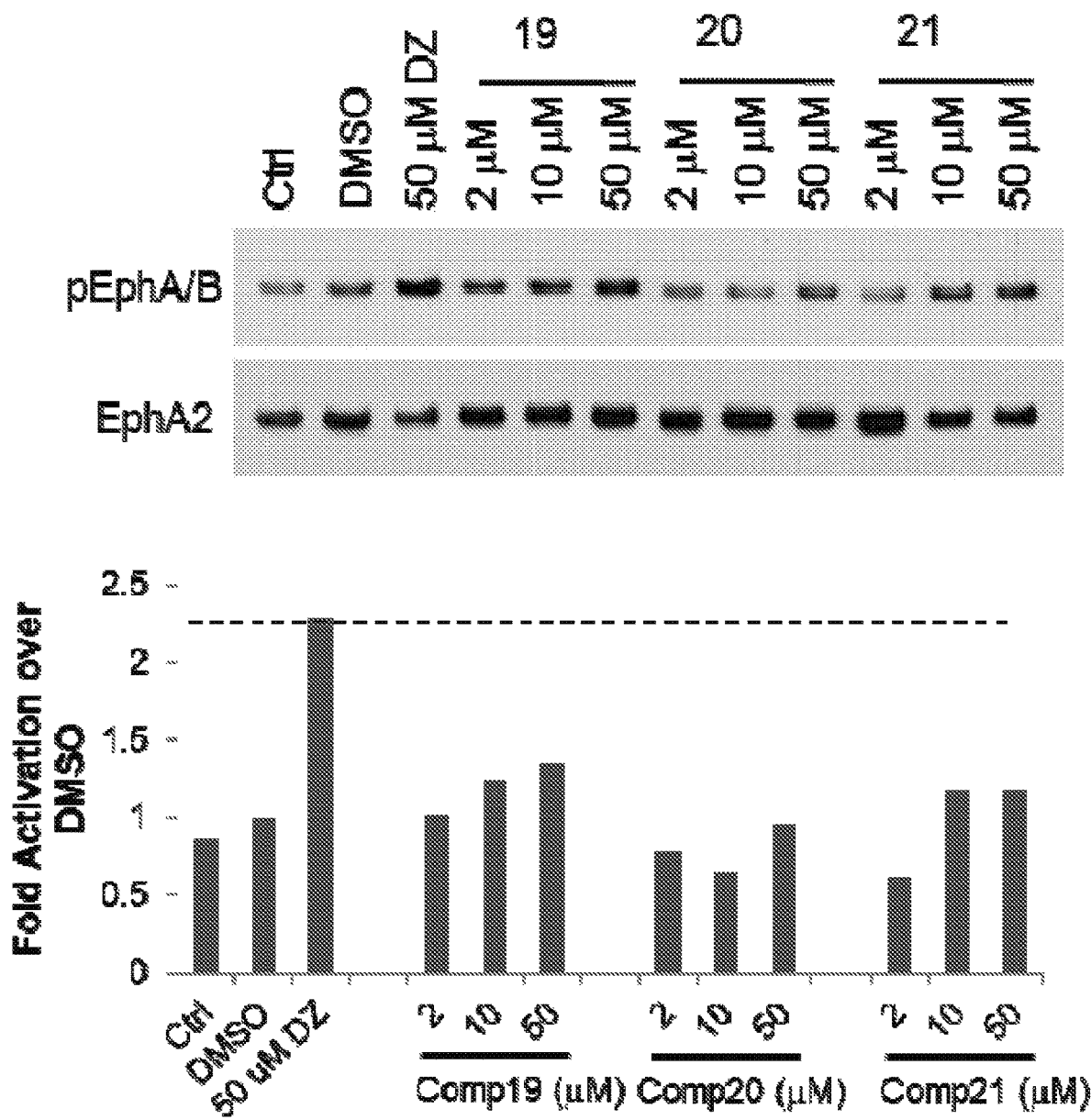
Figure 27:
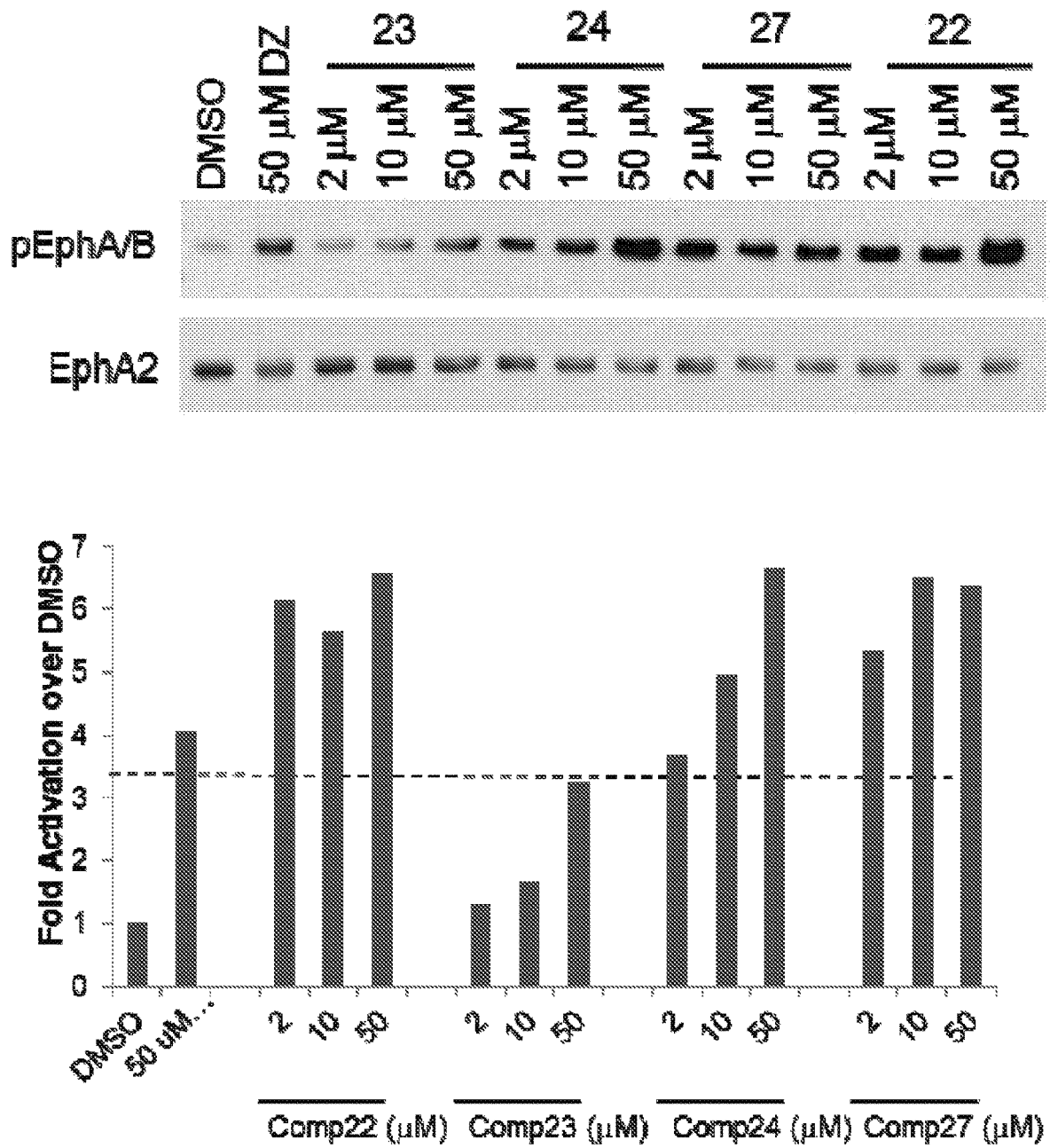
Figure 27:
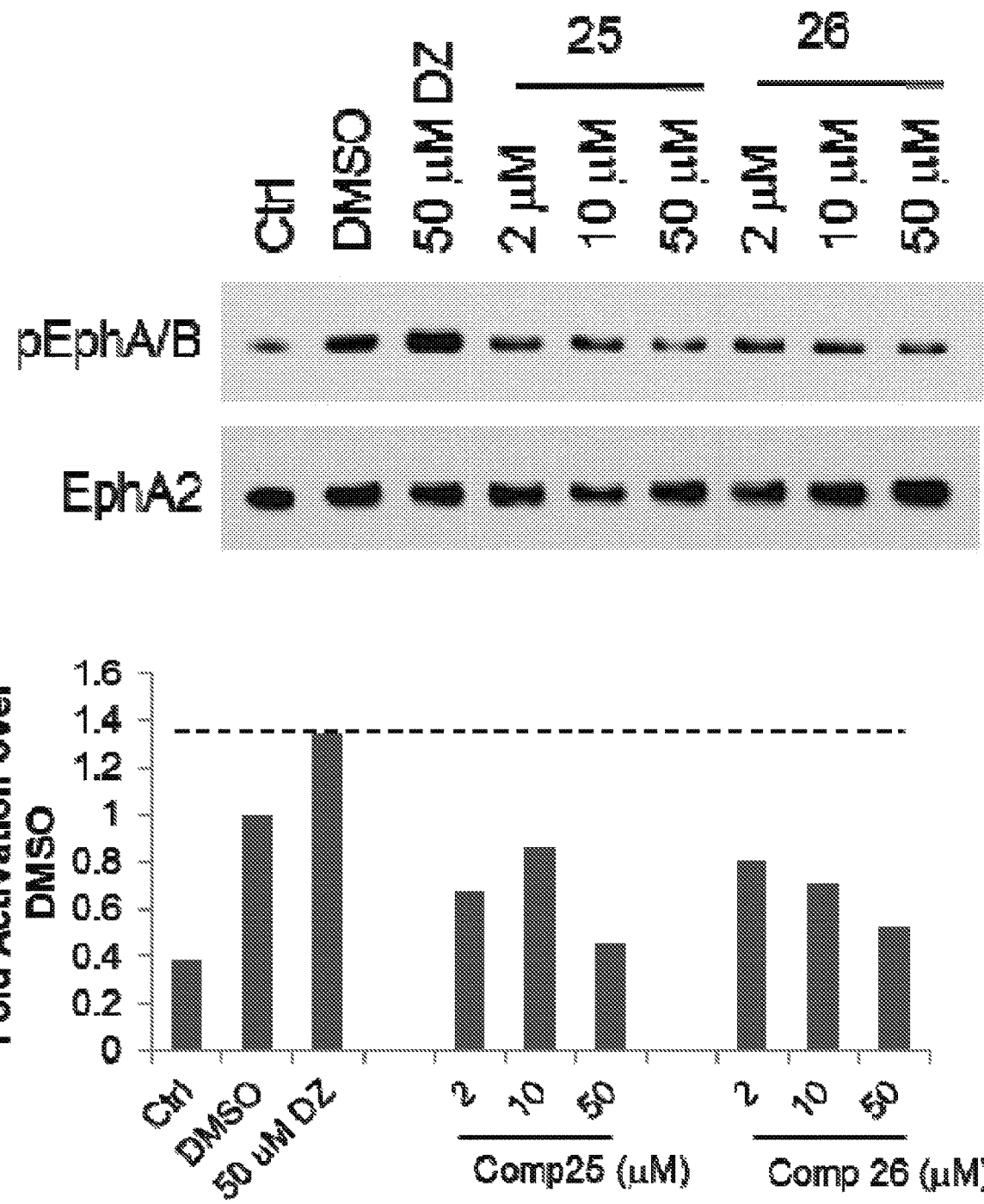
Figure 27:
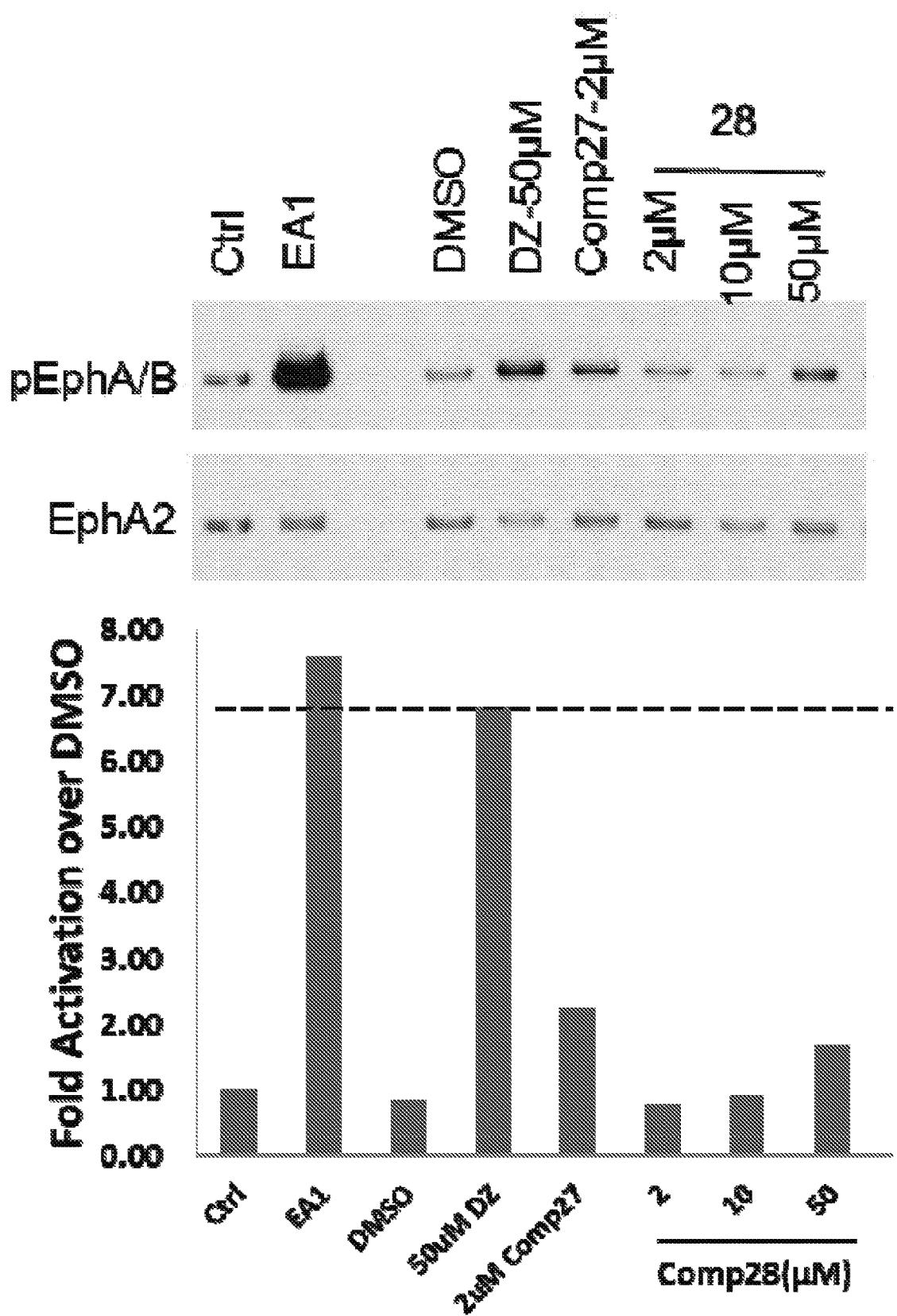
Figure 27:
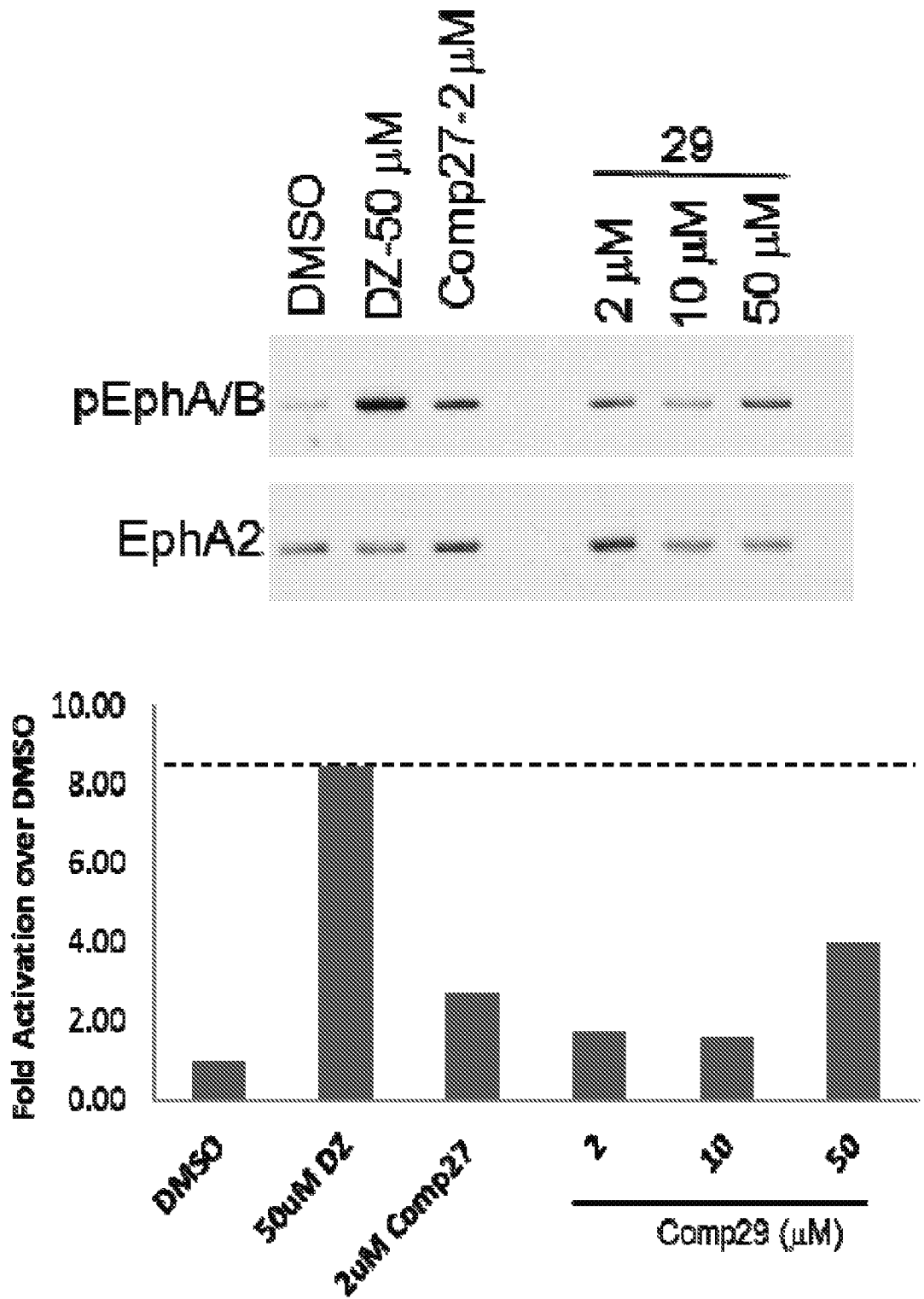
Figure 27:
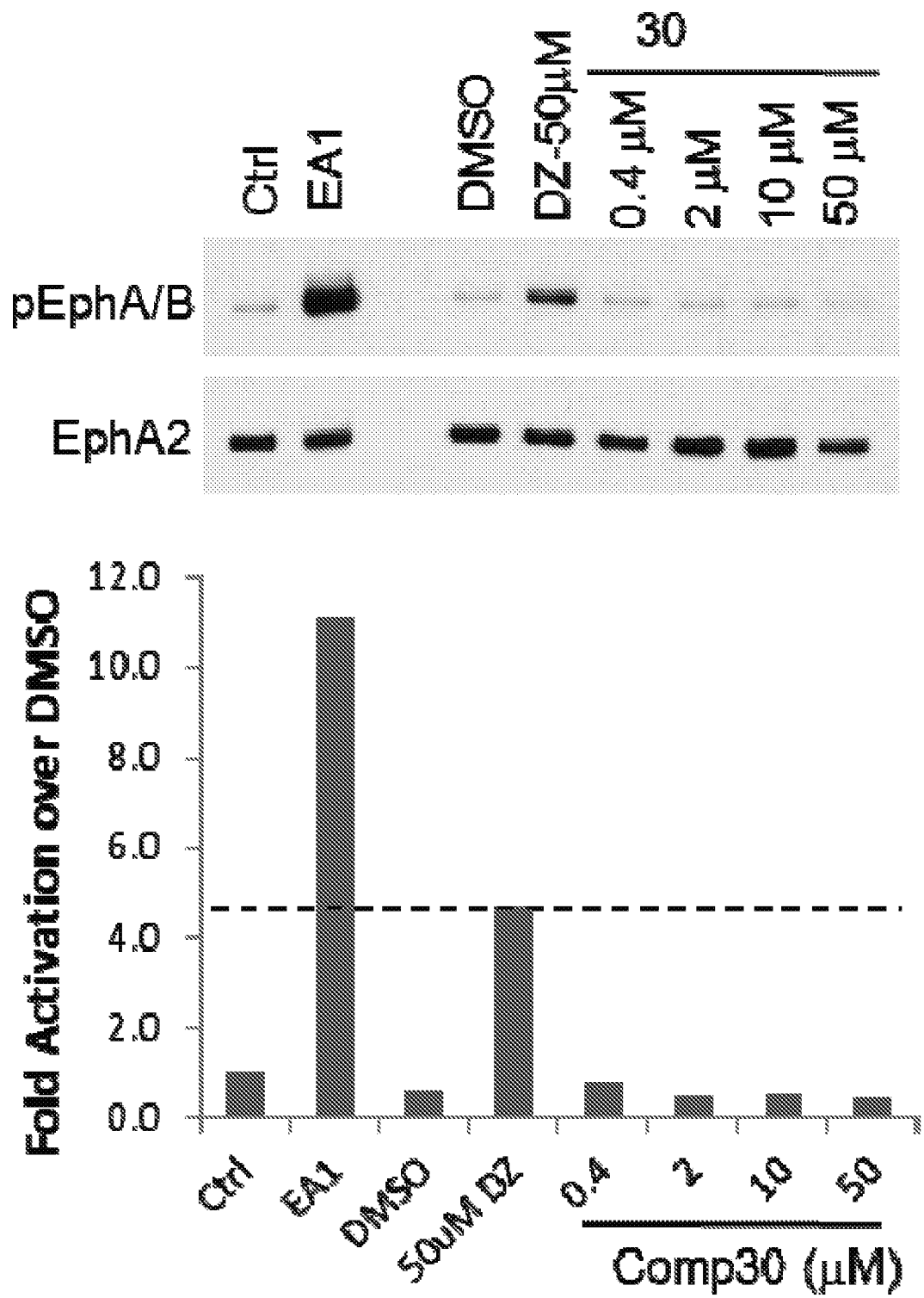
Figure 27:
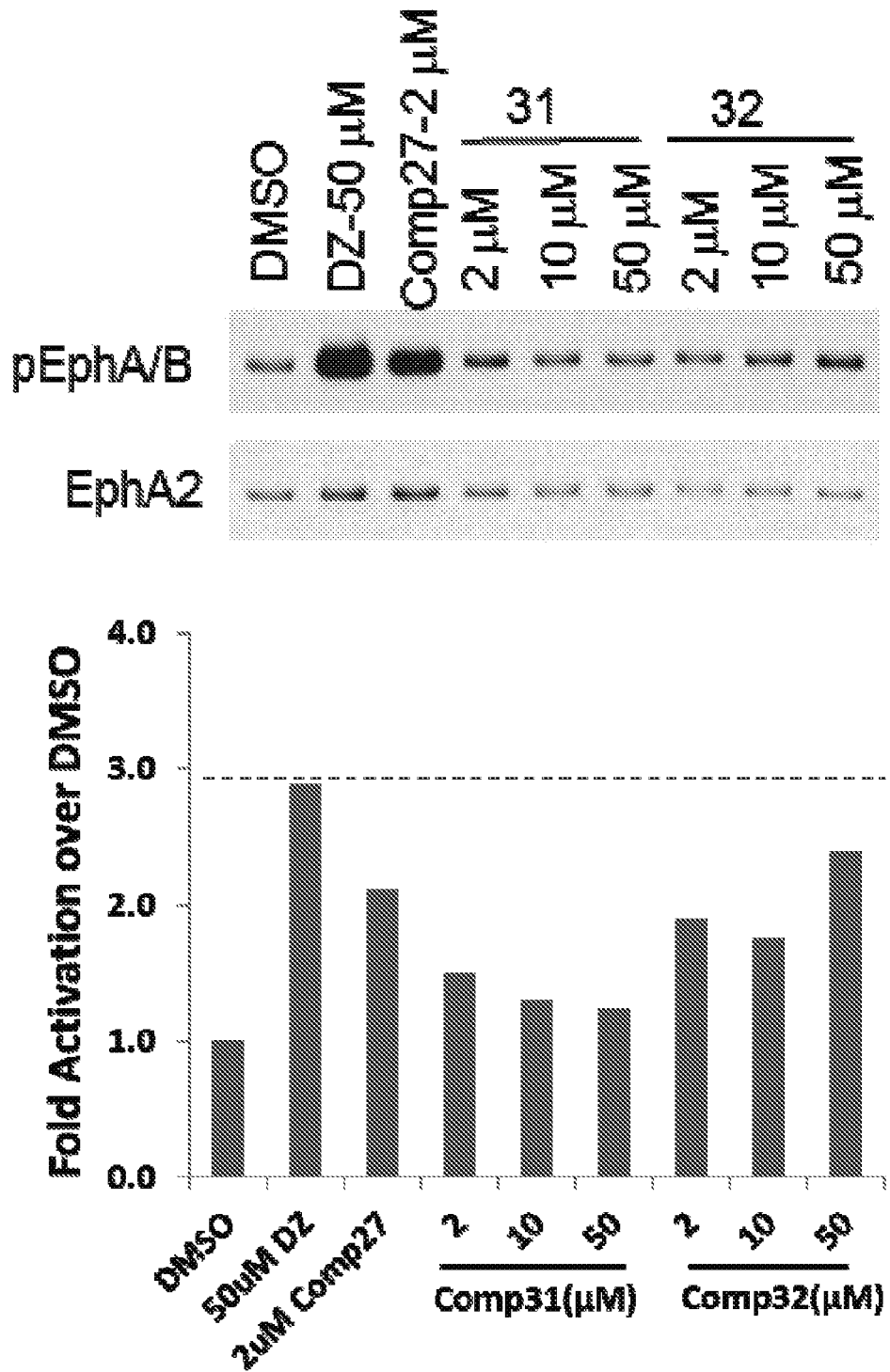
Figure 27:
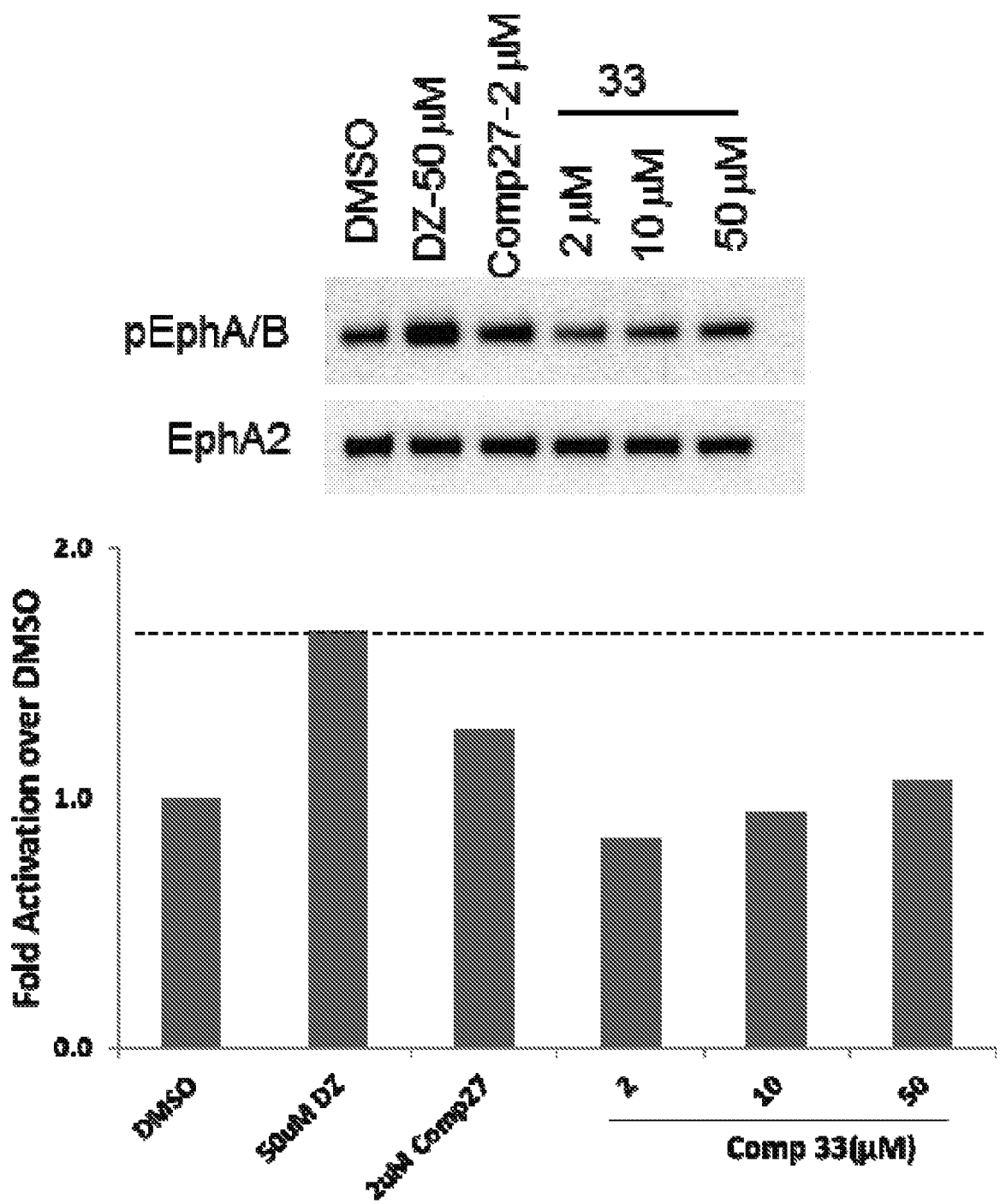

To evaluate the compounds, we utilized a MDA-MB-231 breast cancer cell line which overexpresses EphA2 receptor (MDA-MB-231-A2). The ratio of phosphorylated EphA2 protein over total EphA2 protein was measured after treatment with the various compounds as the readout for receptor activation. All the compounds were examined with doses of 2, 10, and 50 μM, and we used 50 μM Doxazosin and 0.5% DMSO as the positive and negative control, respectively (FIG. 27). EphA2 activation by 50 μM Doxazosin was used as the cutoff to identify more potent analogs. Compounds BW1-24 all showed different substitution at the C moiety as indicated in Scheme 1. Compounds 1 and 2 with bulky C domain seemed to show higher activity than compound 3. However, 50 μM compounds 1 and 2 did not show a much higher activity than the lead compound Doxazosin at 50 μM. Compounds 4-8 all have one carbon extension at C moiety, and the activity of these compounds are comparable to Doxazosin. Compounds 9, 10, 18, 19 and 20 that have heteroaromatic ring at C moiety showed decreased activity, which rules out other possible substitution with heteroaromatic ring in the future. Compounds 11, 12, 22 and 24 have slightly or very bulky and electron donating substitute group at the aromatic ring of C moiety, and compounds 22 and 24 show similar or significantly increased activity compared to Doxazosin, whereas compound 13 with electron withdrawing substitution group decreases the activity. However, compound 21 shows decreased activity even with an electron donating group at 4' aromatic ring of C moiety. Compounds BW14-17 all have alky substitute groups at C moiety and show decreased activity, suggesting that small non-aromatic substitution at C moiety diminishes the activity and should be avoided in the future modification. Compound 23 has a long alky chain at C moiety and shows slightly decreased activity. Based on the structure of 23, we designed dimer structures as demonstrated by compounds 27 and 28. Compound 27 shows significantly increased activity compared to Doxazosin, whereas compound 28 with short linkage shows decreased activity, suggesting that the length of the linkage of the dimer is critical for the activity. Inspired by the dimer design, we also generated dimer structure based on the piperazine ring as the core as illustrated by compounds 25 and 26. However, both compounds show significantly decreased activity.

Besides C moiety, we also modified the structures of the A and B moieties. Compounds 29 and 30 were based on compounds Doxazosin and 24, respectively. The amino group was acetylated to generate the new analogs. The results indicate that the amino group seems critical for the activity, and the acetylation significantly diminishes the activity. In compounds 31 and 32, we replaced the amino group with piperidine and pyrrolidine groups, respectively, and all of these changes harm the EphA2 activation. For the A moiety, we changed the dimethoxy of compound 24 to generated compound 33. Unfortunately, this modification diminishes the activity as well. The structure activity relationship demonstrates that A and B moieties of Doxazosin are critical for the activity and C moiety is an open area for further optimization. In addition, the dimer structure of compound 27 provides a new platform to design new core structures for a group of new analogs to activate EphA2.

EphA2 Internalization

EphA2 overexpression has been identified in various different malignant cells. Decreased levels of EphA2-ligand binding in cancer cells lead to the aggressive growth of the tumor, which can be overcome in vitro by using either monoclonal antibodies, or small molecule ligand. In our previous studies, we have demonstrated that EphA2 ligands negatively regulate tumor cell growth and invasiveness. Ligand binding could even reverse the oncogenic effects of EphA2 overexpression. How did EphA2 ligands reverse the oncogenic effects of EphA2 overexpression. Previous studies have demonstrated that ligand binding causes EphA2 to be internalized and degraded. Since we have developed small molecule EphA2 ligands based on Doxazosin as the lead compound and they can effectively activate the kinase, it is necessary to determine if the ligand could cause EphA2 internalization.

Figure 28:
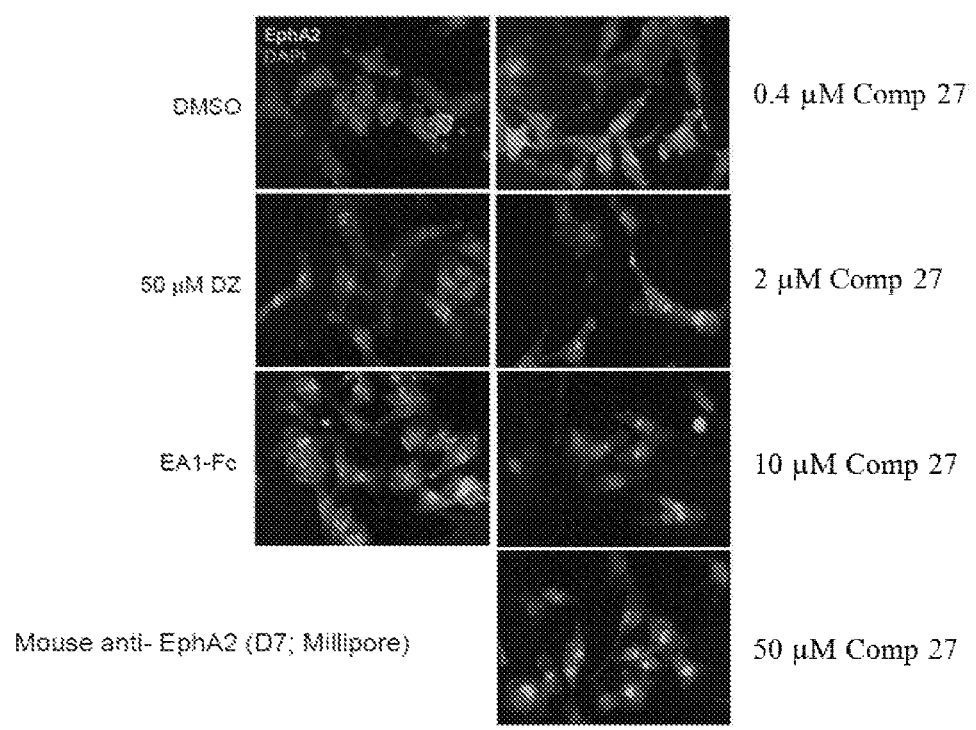
FIG. 28 illustrates Immunofluorescence staining of MDA-MB-231 cells for EphA2 receptor (green) after treatment for 60 minutes with various concentration of compound 27 in 0.5% DMSO. Treatment with 1 ug/mL ephrin-A1-Fc, 50 uM Doxazosin and 0.5% DMSO served as positive and negative controls, respectively. DAPI nuclear staining is shown in blue. Scale bars, 25 um. Cells were seeded on 24-well plates and stimulated after 24-48 hours. The experiment was repeated three times independently, and the representative one is listed.

To directly demonstrate this phenomenon at the cellular level, we used immunofluorescence to monitor localization of EphA2 following the small molecule treatment. This was performed using the MDA-MB-231 cell line. This cell line spreads well in culture, thereby facilitating immunofluorescence detection of cell surface and intracellular EphA2 (FIG. 28). Ephrin-A1-Fc was used as a positive control, which induced nearly complete internalization of EphA2 within 60 min. Consistent with its agonistic activities, Doxazosin also stimulated significant EphA2 internalization at 50 µM. Compound 27, the most active one in the SAR study, was chosen to perform the internalization study. The results showed that EphA2 internalization by compound 27 even happened in very low concentration as 0.4 µM, which indicates that compound 27 has much better potency to induce EphA2 internalization than Doxazosin. Together, these data confirm that the new analog indeed triggers EphA2 receptor internalization in keeping with its agonistic activities.

Compound 27 Inhibits Cancer Cell Colony Formation

Figure 29:
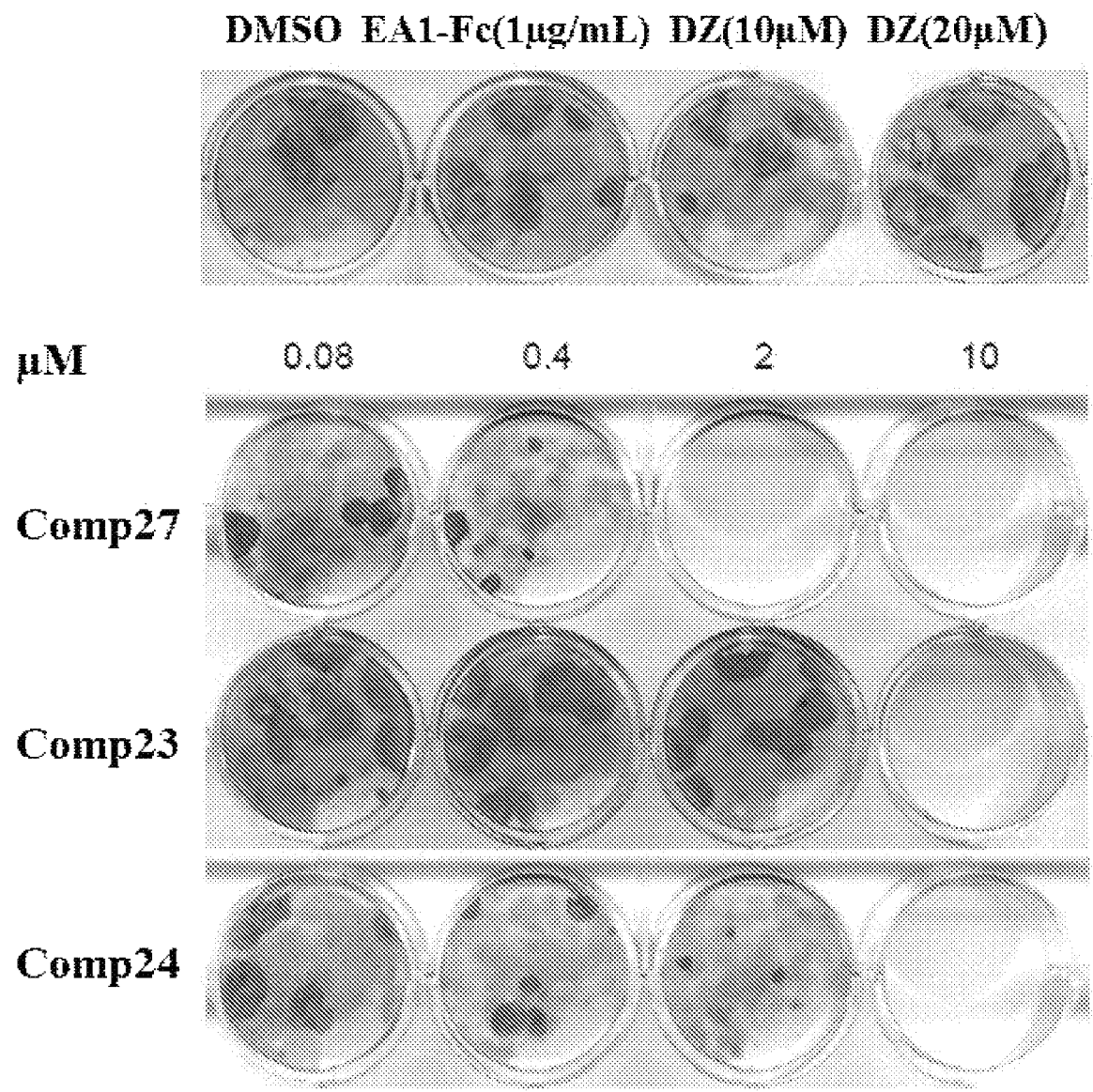
FIG. 29 illustrates that compound 27 inhibits cancer cell colony formation in MD-MB-213 cells. MDA-MB-231 cells (1000 cells/well) were seeded in 12-well plates and cultured for 24 h, followed by treatment with various concentrations of the Doxazosin analogs (0, 0.08, 0.4, 2 and 10 μM) for 14 days. EA1-Fc (1 μg/mL) and Doxazosin (10 μM and 20 μM) were used as positive controls. After washing with PBS, colonies were fixed and stained with crystal violet. The experiment was repeated three times independently, and the representative one is listed.

EphA2 is involved in tumorigenesis, growth and metastasis. Compound 27 can activate EphA2 and induce the internalization of the receptor. Next, we examined if the compound could inhibit tumor growth with a colony formation assay. The same MDA-MB-231 breast cancer cells were treated with compound 27 at various concentrations for two weeks (FIG. 29). The results indicated that the compound inhibited colony formation even at nanomolar concentrations. We also determined the activity of compounds 23 and 24. Compound 23 is the monomer of compound 27 and compound 24 showed potent EphA2 activation in the SAR study. The results revealed that compound 23 showed moderate activity to inhibit the colony formation, and compound 24 showed slightly weaker activity compared to compound 27.

Docking of Compounds 24 and 27 to EphA2

Doxazosin has been demonstrated as a small molecule ligand of EphA2, and the docking domain has been identified with NMR approach and other biological assays. Compounds 24 and 27 showed improved EphA2 activation compared to Doxazosin. We would like to see if the new ligand shows any stronger interaction to the binding domain of Doxazosin in EphA2. To further elucidate the binding characteristics of the compounds with EphA2, we performed docking studies with Doxazosin, 24, and 27 with the crystal structure (PDB:3FL7) of the EphA2 extracellular domain. As illustrated in FIG. 30 upper panel, the aromatic amino group of Doxazosin forms hydrogen bonds with GLY51, SER68; the oxygen of the Dioxane ring forms hydrogen bond with ARG103. In addition to the polar interaction, the dihydrobenzo-dioxine moiety sits inside a hydrophobic pocket. Compared to Doxazosin, compound 24 forms more hydrogen bonds (FIG. 30, middle panel). The methoxy group forms hydrogen bond with GLY51, the aromatic amino group forms hydrogen bonds with GLY51, SER68. The ketone of the amide bond forms hydrogen bond with ARG103. The binding characteristics of compound 24 are quite similar to Doxazosin, and the aromatic group of the amide bond sits inside the same hydrophobic pocket. However, the aromatic group of compound 24 is bulkier than Doxazosin, which pushes the structure a little bit out, and makes the methoxy group closer to GLY51 to form the extra hydrogen bond. The results suggest that compound 24 may have higher binding affinity to EphA2 than Doxazosin, which is consistent with previous EphA2 activation study. However, the most potent compound 27 has very different structure scaffold compared to Doxazosin and compound 24. The binding manner of this ligand looks very different to Doxazosin and compound 24 (FIG. 30, low panel). Due to the bulkiness of the structure, it does not fit into the hydrophobic pocket anymore. The molecule adapts itself into two grooves of the protein. Besides the regular hydrophobic interaction, it forms 4 hydrogen bonds as well. One of the nitrogens in the quinazoline ring forms two hydrogen bonds with ARG159, and one of the ketone forms two hydrogen bonds with ARG103. To fit into the two grooves, the length of the linker seems quite critical, and short linker could not provide enough flexibility for the structure to bind to the groove. Compared to compound 27, compound 28 has a shorter multiple carbon linker and does not show any activity to activate EphA2, and could not fit into the two grooves.

Adrenoceptor Binding Activity

Figure 31:
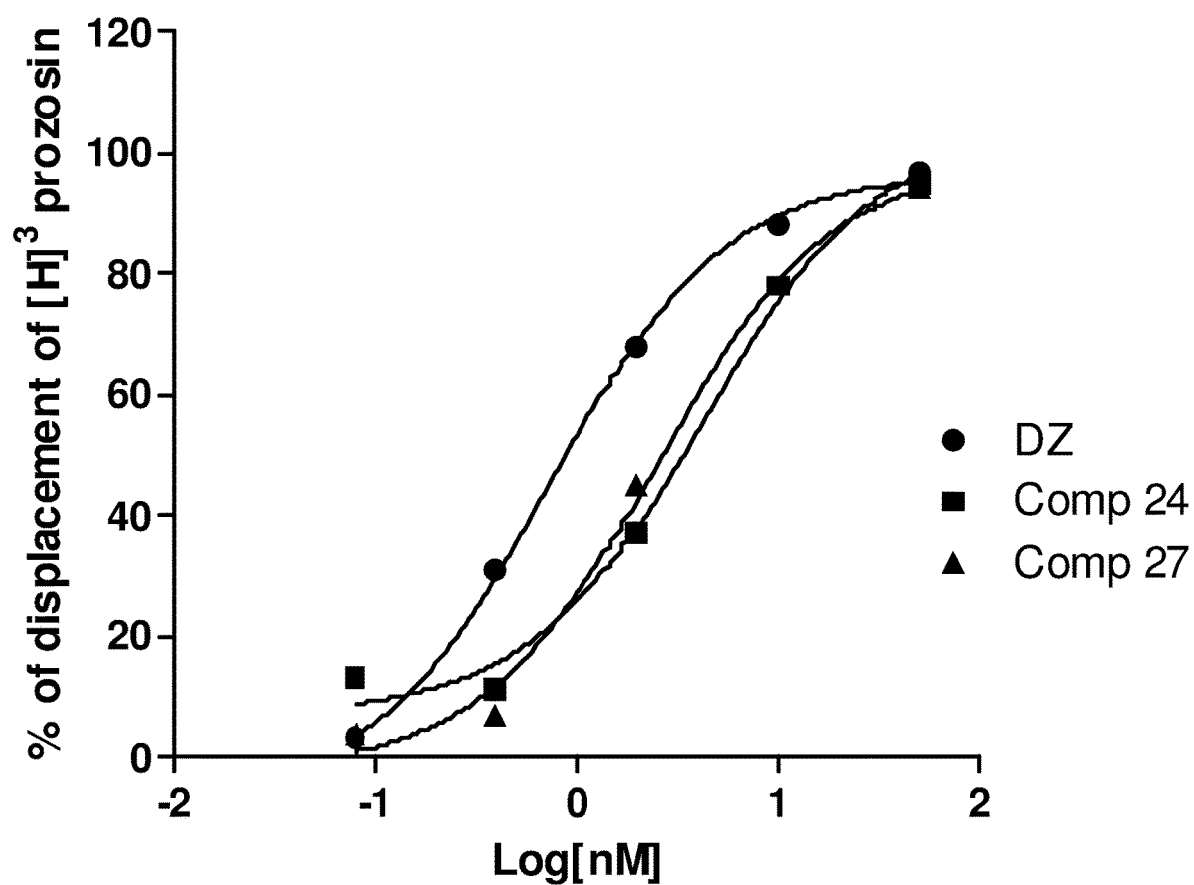
FIG. 31 illustrates compounds 27, 24 and Doxazosin binding with α-adrenoceptor. The compounds were tested in triplication. IC50s of the three compounds were listed as mean±SD.

Doxazosin is an α-adrenoceptor antagonist, and is well used in clinic for the treatment of hypertension or benign prostate hyperplasia. The EphA2 activation of Doxazosin is independent of the α-adrenoceptor activity. During the lead optimization process, we would like to gradually eliminate the α-adrenoceptor binding activity of Doxazosin, and improve the EphA2 activation potency in the new derivatives. To examine if our new analogs still show α-adrenoceptor binding activity, we performed the competition experiments with these ligands. We used Doxazosin as the positive control for the binding assay, and Prazosin as the competitor to the receptor. As shown in FIG. 31, Doxazosin shows an $IC_{50}$ of 0.74±0.30 nM, whereas compounds 24 and 27 show $IC_{50}$s of 4.28±3.10 nM and 2.50±1.62 nM, respectively. The results suggest that these modifications actually decreased the α-adrenoceptor binding affinity. Although we won't be able to summarize a structure activity relationship about the α-adrenoceptor binding activity at this stage, the lead optimization process at least showed the feasibility to eliminate the α-adrenoceptor activity of the new derivatives in the future The two most potent new compounds, 24 and 27, inhibit the colony formation of the cancer cells expressing high level of EphA2. Our molecular docking study revealed that the new compounds may possess stronger interaction to the protein than Doxazosin based on the hydrogen bonds formed between the ligands and EphA2. Finally, the new derivatives showed relatively weaker binding affinity to α-adrenoceptor, suggesting that our lead optimization decreased the original targeting effect of Doxazosin.

Materials and Methods

Chemistry

Chemicals were commercially available and used as received without further purification unless otherwise noted. Moisture sensitive reactions were carried out under a dry argon atmosphere in flame-dried glassware. Solvents were distilled before use under argon. Thin-layer chromatography was performed on precoated silica gel F254 plates (Whatman). Silica gel column chromatography was performed using silica gel 60 Å (Merck, 230-400 Mesh), and hexane/ethyl acetate was used as the elution solvent. Mass spectra were obtained on the electrospray mass spectrometer at Cleveland State University MS facility Center. The molecular weight of the compounds was examined with LC-MS. All the NMR spectra were recorded on a Bruker 400 MHz in either DMSO-$d_6$ or CDCl$_3$. Chemical shifts (δ) for $^1$H NMR spectra are reported in parts per million to residual solvent protons.

Compounds 1-24, 27 and 28 were Prepared as the Following Procedure

The dimethoxyquinazolin and piperazine were dissolved in n-BuOH with 1 to 5 mole ratio, and the mixture was heated to 100° C. for 24 hours, then it was cooled down to room temperature. The precipitated while solid was collected via filtration and washed with n-BuOH. After it was dried, the solid was mixed with various different substituted acetyl chloride and K$_2$CO$_3$ in DMF. It was stirred until the reaction was completed. The reaction was quenched with Na$_2$CO$_3$ aqueous solution and stirred overnight, and the precipitated product was collected via filtration and washed with water and dried to give the corresponding compounds.

(4-(4-amino-6,7-dimethoxyquinazolin-2-yl)piperazin-1-yl)(naphthalen-2-yl)methanone (1)

White solid, 72% yield for the last step; $^1$H-NMR (400 MHz, DMSO-$d_6$) δ 8.016 (4H, m), 7.580 (3H, m), 7.440 (1H, s), 7.167 (2H, br), 6.745 (1H, s), 3.795 (12H, m), 3.490 (2H, br). $^{13}$C-NMR (100 MHz, DMSO-$d_6$) δ 169.642, 161.632, 158.757, 154.699, 149.117, 145.535, 133.709, 132.754, 130.970, 129.745, 128.525, 127.826, 125.353, 105.645, 104.111, 103.460, 67.487, 56.294, 66.889, 25.592. DUIS-MS calculated for C$_{25}$H$_{25}$N$_5$O$_4$ [M+M]$^+$: 444.1, found: 443.5.

[1,1'-biphenyl]-3-yl(4-(4-amino-6,7-dimethoxyquinazolin-2-yl)piperazin-1-yl)methanone (2)

White solid, 73% yield for the last step; $^1$H-NMR (400 MHz, DMSO-$d_6$) δ 7.735 (4H, m), 7.498 (6H, m), 7.152 (2H, br), 6.740 (1H, s), 3.794 (12H, m), 3.464 (2H, m). $^{13}$C-NMR (100 MHz, DMSO-$d_6$) δ 169.475, 161.620, 158.802, 154.687, 149.184, 145.519, 140.765, 139.825, 137.207, 129.509, 128.279, 127.297, 126.522, 125.633, 105.669, 104.085, 103.455, 56.287, 66.879. DUIS-MS calculated for C$_{27}$H$_{27}$N$_5$O$_3$ [M+H]$^+$: 470.1, found: 469.2.

(4-(4-amino-6,7-dimethoxyquinazolin-2-yl)piperazin-1-yl)(benzo[d][1,3]dioxol-5-yl)methanone (3)

White solid, 71% yield for the last step; $^1$H-NMR (400 MHz, DMSO-$d_6$) δ 7.431 (1H, s), 7.145 (2H, br), 6.981 (3H, m), 6.736 (1H, s), 6.094 (2H, s), 3.791 (10H, m), 3.541 (4H, br). $^{13}$C-NMR (100 MHz, DMSO-$d_6$) δ 169.133, 161.610, 158.769, 154.682, 149.187, 148.700, 147.605, 145.499, 130.049, 121.990, 108.458, 105.666, 104.094, 103.440, 101.901, 56.503, 56.283, 55.878, 44.074, 19.023. DUIS-MS calculated for C$_{22}$H$_{23}$N$_5$O$_5$ [M+H]$^+$: 438.1, found: 437.5.

1-(4-(4-amino-6,7-dimethoxyquinazolin-2-yl)piperazin-1-yl)-2-(4-methoxyphenyl)ethanone (4)

White solid, 65% yield for the last step; $^1$H-NMR (400 MHz, DMSO-$d_6$) δ 7.422 (1H, s), 7.168 (4H, m), 6.881 (2H, d, J=8.8 Hz), 6.734 (1H, s), 3.831 (3H, s), 3.788 (3H, s), 3.729 (3H, s), 3.671 (4H, m), 3.601 (2H, br), 3.532 (4H, br). $^{13}$C-NMR (100 MHz, DMSO-$d_6$) δ 169.795, 161.584, 158.522, 154.669, 149.169, 145.485, 130.419, 128.163, 114.233, 105.668, 104.061, 103.412, 56.276, 55.662, 45.928, 44.254, 43.886, 41.754. DUIS-MS calculated for C$_{23}$H$_{27}$N$_5$O$_4$ [M+H]$^+$: 438.1, found: 437.5.

1-(4-(4-amino-6,7-dimethoxyquinazolin-2-yl)piperazin-1-yl)-2-(3-methoxyphenyl)ethanone (5)

White solid, 60% yield for the last step; $^1$H-NMR (400 MHz, DMSO-$d_6$) δ 7.423 (1H, s), 7.231 (1H, m), 7.143 (1H, br), 6.817 (3H, m), 6.737 (1H, s), 3.830 (3H, s), 3.788 (3H, s), 3.738 (5H, m), 3.598 (9H, m). $^{13}$C-NMR (100 MHz, DMSO-$d_6$) δ 169.382, 161.590, 159.707, 158.745, 154.676, 149.159, 145.495, 137.832, 129.834, 121.631, 115.114, 112.281, 105.662, 104.060, 103.416, 67.488, 56.275, 55.643, 45.977, 44.237, 43.878, 41.783. DUIS-MS calculated for C$_{23}$H$_{27}$N$_5$O$_4$ [M+H]$^+$: 438.1, found: 437.5.

1-(4-(4-amino-6,7-dimethoxyquinazolin-2-yl)piperazin-1-yl)-2-phenylethanone (6)

White solid, 96% yield for the last step; $^1$H-NMR (400 MHz, DMSO-$d_6$) δ 7.420 (1H, s), 7.272 (5H, m), 7.140 (2H, br), 6.733 (1H, s), 3.829 (3H, s), 3.786 (3H, s), 3.775 (2H, s), 3.607 (8H, m). $^{13}$C-NMR (100 MHz, DMSO-$d_6$) δ 169.500, 161.590, 158.759, 154.674, 149.173, 145.492, 136.385, 129.469, 128.807, 126.828, 105.672, 104.064, 103.419, 56.279, 55.877, 45.955, 44.239, 43.883, 41.778. DUIS-MS calculated for C$_{22}$H$_{25}$N$_5$O$_3$ [M+H]$^+$: 408.1, found: 407.2.

1-(4-(4-amino-6,7-dimethoxyquinazolin-2-yl)piperazin-1-yl)-2-(naphthalen-2-yl)ethanone (7)

White solid, 70% yield for the last step; $^1$H-NMR (400 MHz, DMSO-$d_6$) δ 7.862 (3H, m), 7.774 (1H, s), 7.436 (4H, m), 7.133 (2H, br), 6.725 (1H, s), 3.957 (2H, s), 3.823 (3H, s), 3.782 (3H, s), 3.610 (8H, m). $^{13}$C-NMR (100 MHz, CDCl$_3$-$d_6$) δ 169.688, 160.521, 158.510, 155.158, 149.759, 145.970, 133.577, 132.459, 128.540, 127.446, 126.517, 125.780, 105.814, 102.901, 101.134, 56.160, 46.256, 43.913, 41.707. DUIS-MS calculated for C$_{26}$H$_{27}$N$_5$O$_3$ [M+H]$^+$: 458.1, found: 457.5.

1-(4-(4-amino-6,7-dimethoxyquinazolin-2-yl)piperazin-1-yl)-2-phenylpropan-1-one (8)

White solid, 82% yield for the last step; $^1$H-NMR (400 MHz, DMSO-$d_6$) δ 7.400 (1H, s), 7.306 (5H, m), 7.112 (2H, br), 6.704 (1H, s), 4.155 (1H, q, J=6.8 Hz), 3.816 (3H, s), 3.775 (3H, s), 3.680-3.399 (6H, m), 3.007 (1H, m), 1.316 (3H, d, J=6.8 Hz). $^{13}$C-NMR (100 MHz, CDCl$_3$-$d_6$) δ

172.254, 160.514, 158.541, 155.142, 149.783, 145.917, 142.085, 128.993, 127.214, 126.849, 105.782, 102.866, 101.177, 56.091, 45.570, 43.777, 42.118, 20.719. DUIS-MS calculated for $C_{22}H_{23}N_5O_5$ [M+H]$^+$: 422.1, found: 421.5.

(4-(4-amino-6,7-dimethoxyquinazolin-2-yl)piperazin-1-yl)(pyridin-2-yl)methanone (9)

White solid, 42% yield for the last step; $^1$H-NMR (400 MHz, DMSO-d$_6$) δ 8.625 (1H, d, J=4.4 Hz), 7.952 (1H, t, J=8 Hz), 7.615 (1H, d, J=8 Hz), 7.507 (1H, m), 7.432 (1H, s), 7.156 (2H, br), 6.738 (1H, s), 3.831-3.726 (12H, m), 3.469 (2H, m). $^{13}$C-NMR (100 MHz, DMSO-d$_6$) δ 167.378, 161.623, 158.737, 154.599, 149.175, 148.901, 145.529, 137.864, 125.097, 123.712, 105.685, 104.109, 103.456, 56.299, 55.886, 47.042, 44.409, 43.866, 42.193. DUIS-MS calculated for $C_{20}H_{22}N_6O_3$ [M+H]$^+$: 395.1, found: 394.4.

(4-(4-amino-6,7-dimethoxyquinazolin-2-yl)piperazin-1-yl)(pyridin-4-yl)methanone (10)

White solid, 32% yield for the last step; $^1$H-NMR (400 MHz, DMSO-d$_6$) δ 8.697 (2H, d, J=4.8 Hz), 7.444 (3H, m), 7.163 (2H, br), 6.735 (1H, s), 3.830-3.710 (14H, m) (Note: it seems that two protons are missing but they may overlap with the peak from water). $^{13}$C-NMR (100 MHz, DMSO-d$_6$) δ 167.422, 161.632, 158.709, 154.711, 150.553, 149.161, 145.559, 143.952, 121.794, 105.669, 104.104, 103.463, 56.301, 55.896, 47.319, 44.215, 43.737, 41.990. DUIS-MS calculated for $C_{20}H_{22}N_6O_3$ [M+H]$^+$: 395.1, found: 394.4.

(4-(4-amino-6,7-dimethoxyquinazolin-2-yl)piperazin-1-yl)(4-ethylphenyl)methanone (11)

White solid, 84% yield for the last step; $^1$H-NMR (400 MHz, DMSO-d$_6$) δ 7.433 (1H, s), 7.370 (2H, d, J=8 Hz), 7.302 (2H, d, J=8 Hz), 7.154 (2H, br), 6.735 (1H, s), 3.831-3.445 (14H, m), 2.660 (2H, q, J=7.6 Hz), 1.214 (3H, t, J=7.6 Hz). $^{13}$C-NMR (100 MHz, DMSO-d$_6$) δ 169.768, 161.614, 158.774, 154.687, 149.181, 145.696, 133.742, 128.206, 127.749, 105.667, 104.088, 103.453, 56.284, 55.877, 28.458, 15.801. DUIS-MS calculated for $C_{23}H_{27}N_5O_3$ [M+H]$^+$: 422.1, found: 421.5.

(4-(4-amino-6,7-dimethoxyquinazolin-2-yl)piperazin-1-yl)(4-iodophenyl)methanone (12)

White solid, 85% yield for the last step; $^1$H-NMR (400 MHz, DMSO-d$_6$) δ 7.843 (2H, d, J=8 Hz), 7.423 (1H, s), 7.252 (2H, d, J=8 Hz), 7.144 (2H, br), 6.735 (1H, s), 3.841-3.716 (14H, m). $^{13}$C-NMR (100 MHz, DMSO-d$_6$) δ 168.865, 161.618, 158.734, 154.704, 149.161, 145.533, 137.730, 135.857, 129.657, 105.670, 104.110, 103.454, 96.865, 56.301, 55.893. DUIS-MS calculated for $C_{21}H_{22}IN_5O_3$ [M+H]$^+$: 520.0, found: 519.3.

(4-(4-amino-6,7-dimethoxyquinazolin-2-yl)piperazin-1-yl)(4-chloro-3-nitrophenyl)methanone (13)

White solid, 91% yield for the last step; $^1$H-NMR (400 MHz, DMSO-d$_6$) δ 8.179 (1H, s), 7.883 (1H, d, J=8 Hz), 7.792 (1H, d, J=8 Hz), 7.434 (1H, s), 7.159 (2H, br), 6.740 (1H, s), 3.833-3.401 (14H, m). $^{13}$C-NMR (100 MHz, DMSO-d$_6$) δ 166.451, 161.632, 158.722, 154.699, 149.143, 148.029, 145.547, 136.683, 132.589, 126.400, 124.905, 105.664, 104.089, 103.456, 56.293, 55.892. DUIS-MS calculated for $C_{21}H_{21}ClN_6O_5$ [M+H]$^+$: 473.0, found: 472.9.

1-(4-(4-amino-6,7-dimethoxyquinazolin-2-yl)piperazin-1-yl)ethanone (14)

White solid, 88% yield for the last step; $^1$H-NMR (400 MHz, DMSO-d$_6$) δ 7.426 (1H, s), 7.143 (2H, br), 6.745 (1H, s), 3.836-3.684 (10H, m), 3.490 (4H, m), 2.050 (3H, s). $^{13}$C-NMR (100 MHz, DMSO-d$_6$) δ 168.845, 161.606, 158.768, 154.682, 149.209, 145.469, 105.675, 104.106, 103.410, 56.289, 55.885, 46.158, 44.261, 43.872, 41.361, 21.803. DUIS-MS calculated for $C_{16}H_{21}N_5O_3$ [M+H]$^+$: 332.1, found: 331.4.

1-(4-(4-amino-6,7-dimethoxyquinazolin-2-yl)piperazin-1-yl)propan-1-one (15)

White solid, 63% yield for the last step; $^1$H-NMR (400 MHz, DMSO-d$_6$) δ 7.428 (1H, s), 7.141 (2H, br), 6.746 (1H, s), 3.837-3.686 (10H, m), 3.507 (4H, m), 2.366 (2H, q, J=7.2 Hz), 1.017 (3H, t, J=7.2 Hz). $^{13}$C-NMR (100 MHz, DMSO-d$_6$) δ 171.950, 161.602, 158.795, 154.682, 149.227, 145.466, 105.680, 104.110, 103.413, 56.289, 55.879, 45.251, 44.304, 43.930, 41.538, 26.125, 9.897. DUIS-MS calculated for $C_{17}H_{23}N_5O_3$ [M+H]$^+$: 346.1, found: 345.4.

1-(4-(4-amino-6,7-dimethoxyquinazolin-2-yl)piperazin-1-yl)butan-1-one (16)

White solid, 72% yield for the last step; $^1$H-NMR (400 MHz, DMSO-d$_6$) δ 7.426 (1H, s), 7.142 (2H, br), 6.743 (1H, s), 3.836 (3H, s), 3.791 (3H, s), 3.735 (2H, m), 3.683 (2H, m), 3.507 (4H, m), 2.337 (2H, t, J=7.2 Hz), 1.555 (2H, m), 0.914 (3H, t, J=7.6 Hz). $^{13}$C-NMR (100 MHz, DMSO-d$_6$) δ 171.13, 161.60, 158.78, 154.68, 149.23, 145.47, 105.68, 104.11, 103.41, 67.49, 56.29, 55.86, 45.41, 44.37, 43.96, 41.49, 34.76, 25.59, 18.69, 14.31. DUIS-MS calculated for $C_{18}H_{25}N_5O_3$ [M+H]$^+$: 360.1, found: 359.4.

(4-(4-amino-6,7-dimethoxyquinazolin-2-yl)piperazin-1-yl)(cyclohexyl)methanone (17)

White solid, 89% yield for the last step; $^1$H-NMR (400 MHz, DMSO-d$_6$) δ 7.429 (1H, s), 7.138 (2H, br), 6.740 (1H, s), 3.837 (3H, s), 3.792 (3H, s), 3.703 (4H, m), 3.520 (4H, m), 2.627 (1H, m), 1.701 (5H, m), 1.336 (4H, m), 1.174 (1H, m). $^{13}$C-NMR (100 MHz, DMSO-d$_6$) δ 174.107, 161.596, 158.774, 154.691, 149.220, 145.480, 105.684, 104.138, 103.432, 56.299, 55.879, 45.298, 44.640, 43.992, 41.567, 29.631, 26.081, 25.656, 19.020. DUIS-MS calculated for $C_{21}H_{29}N_5O_3$ [M+H]$^+$: 400.2, found: 399.5.

(4-(4-amino-6,7-dimethoxyquinazolin-2-yl)piperazin-1-yl)(furan-2-yl)methanone (18)

White solid, 66% yield for the last step; $^1$H-NMR (400 MHz, DMSO-d$_6$) δ 7.869 (1H, d, J=0.8 Hz), 7.438 (1H, s), 7.162 (2H, br), 7.037 (1H, d, J=3.2 Hz), 6.752 (1H, s), 6.652 (1H, dd, J=0.8, 3.2 Hz), 3.795 (14H, m). $^{13}$C-NMR (100 MHz, DMSO-d$_6$) δ 161.633, 158.862, 154.712, 149.213, 147.474, 145.521, 145.205, 116.020, 111.775, 105.700, 104.137, 103.463, 67.487, 56.302, 55.886, 44.153, 25.591. DUIS-MS calculated for $C_{19}H_{21}N_5O_4$ [M+H]$^+$: 384.1, found: 383.4,

(4-(4-amino-6,7-dimethoxyquinazolin-2-yl)piperazin-1-yl)(thiophen-2-yl)methanone (19)

White solid, 56% yield for the last step; $^1$H-NMR (400 MHz, DMSO-d$_6$) δ 7.784 (1H, d, J=4.8 Hz), 7.475 (1H, d, J=3.2 Hz), 7.438 (1H, s), 7.161 (3H, m), 6.750 (1H, s), 3.811(10H, m), 3.761 (4H, br). $^{13}$C-NMR (100 MHz, DMSO-d$_6$) δ 162.930, 161.637, 158, 732, 154.715, 149.215, 145.523, 137.835, 130.013, 129.650, 127.626, 105.698, 104.143, 103.465, 56.308, 55.892, 44.090. DUIS-MS calculated for C$_{19}$H$_{21}$N$_5$O$_3$S [M+H]$^+$: 400.1, found: 399.5.

(4-(4-amino-6,7-dimethoxyquinazolin-2-yl)piperazin-1-yl)(isoxazol-5-yl)methanone (20)

White solid, 43% yield for the last step; $^1$H-NMR (400 MHz, DMSO-d$_6$) δ 8.782 (1H, s), 7.442 (1H, s), 7.198 (2H, br), 6.984 (1H, s), 6.758 (1H, s), 3.839-3.611 (14H, m). $^{13}$C-NMR (100 MHz, DMSO-d$_6$) δ 161.661, 157.432, 151.435, 145.615, 106.739, 104.129, 103.462, 56.310, 55.916. DUIS-MS calculated for C$_{18}$H$_{20}$N$_6$O$_4$ [M+H]$^+$: 385.1, found: 384.4.

(4-(4-amino-6,7-dimethoxyquinazolin-2-yl)piperazin-1-yl)(4-methoxyphenyl)methanone (21)

White solid, 85% yield for the last step; $^1$H-NMR (400 MHz, DMSO-d$_6$) δ 7.420 (3H, m), 7.148 (2H, br), 7.007 (2H, d, J=8.4 Hz), 6.738 (1H, s), 3.813 (13H, m), 3.557 (4H, m). $^{13}$C-NMR (100 MHz, DMSO-d$_6$) δ 169.598, 161.623, 160.689, 158.790, 154.705, 149.211, 145.517, 129.628, 128.371, 114.131, 105.691, 104.134, 103.458, 56.302, 55.803, 44.140. DUIS-MS calculated for C$_{22}$H$_{25}$N$_5$O$_4$ [M+H]$^+$: 424.1, found: 423.5.

(4-(4-amino-6,7-dimethoxyquinazolin-2-yl)piperazin-1-yl)(4-bromophenyl)methanone (22)

White solid, 83% yield for the last step; $^1$H-NMR (400 MHz, DMSO-d$_6$) δ 7.665 (2H, d, J=8.4 Hz), 7.440 (1H, s), 7.407 (2H, d, J=8.4 Hz), 7.164 (2H, br), 6.744 (1H, s), 3.832 (3H, s), 3.793 (3H, s), 3.725 (6H, m), 3.388 (2H, br). $^{13}$C-NMR (100 MHz, DMSO-d$_6$) δ 168.663, 161.624, 158.747, 154.710, 149.178, 145.538, 136.589, 131.933, 129.770, 123.409, 105.679, 104.115, 103.4584, 56.303, 55.895. DUIS-MS calculated for C$_{21}$H$_{22}$N$_5$O$_3$Br [M+H]$^+$: 474.0, found: 472.5.

1-(4-(4-amino-6,7-dimethoxyquinazolin-2-yl)piperazin-1-yl)hexan-1-one (23)

White solid, 73% yield for the last step; $^1$H-NMR (400 MHz, DMSO-d$_6$) δ 7.427 (1H, s), 7.146 (2H, br), 6.743 (1H, s), 3.834 (3H, s), 3.790 (3H, s), 3.731 (2H, m), 3.679 (2H, m), 3.500 (4H, m), 2.335 (2H, t, J=7.2 Hz), 1.516 (2H, m), 1.287 (4H, m), 0.872 (3H, t, J=6.4 Hz). $^{13}$C-NMR (100 MHz, DMSO-d$_6$) δ 171.287, 161.603, 158.789, 154.690, 149.226, 145.478, 105.679, 104.123, 103.424, 56.294, 55.878, 45.433, 44.380, 43.959, 41.508, 32.789, 31.497, 24.984, 22.452, 14.356. DUIS-MS calculated for C$_{20}$H$_{29}$N$_5$O$_3$ [M+H]$^+$: 388.1, found: 387.5.

1-(4-(4-amino-6,7-dimethoxyquinazolin-2-yl)piperazin-1-yl)-2-(4-(benzyloxy)phenyl)ethanone (24)

White solid, 89% yield for the last step; $^1$H-NMR (400 MHz, DMSO-d$_6$) δ 7.381 (6H, m), 7.169 (4H, m), 6.958 (2H, d, J=8.4 Hz), 6.740 (1H, s), 5.071 (2H, s), 3.830 (3H, s), 3.789 (3H, s), 3.693-3.535 (10H, m). $^{13}$C-NMR (100 MHz, DMSO-d$_6$) δ 169.755, 161.602, 158.781, 157.409, 154.701, 149.206, 145.510, 137.636, 130.455, 128.410, 115.151, 105.703, 104.125, 103.441, 69.643, 67.493, 56.302, 55.879, 45.937, 44.274, 43.903, 41.764, 25.596. DUIS-MS calculated for C$_{29}$H$_{31}$N$_5$O$_4$ [M+H]$^+$: 514.2, found: 513.6.

1,12-bis(4-(4-amino-6,7-dimethoxyquinazolin-2-yl)piperazin-1-yl)dodecane-1,12-dione (27)

White solid, 68% yield for the last step; $^1$H-NMR (400 MHz, DMSO-d$_6$) δ 7.425 (2H, s), 7.145 (4H, br), 6.740 (2H, s), 3.831 (6H, s), 3.787 (6H, s), 3.700 (8H, m), 3.495 (8H, br), 2.331 (4H, t, J=7.2 Hz), 1.504 (4H, br), 1.267 (12H, br). $^{13}$C-NMR (100 MHz, DMSO-d$_6$) δ 171.277, 161.596, 158.786, 154.682, 149.221, 145.467, 105.680, 104.119, 103.417, 56.293, 55.880, 45.427, 44.380, 43.958, 41.504, 32.834, 29.358, 25.306. DUIS-MS calculated for C$_{40}$H$_{56}$N$_{10}$O$_6$ [M+H]$^+$: 774.0, found: 772.9.

1,6-bis(4-(4-amino-6,7-dimethoxyquinazolin-2-yl)piperazin-1-yl)hexane-1,6-dione (28)

White solid, 77% yield for the last step; $^1$H-NMR (400 MHz, DMSO-d$_6$) δ 7.424 (2H, s), 7.138 (4H, br), 6.743 (2H, s), 2.846-2.507 (28H, m), 2.393 (4H, br), 1.567 (4H, br). $^{13}$C-NMR (100 MHz, DMSO-d$_6$) δ 171.217, 161.602, 158.789, 154.683, 149.218, 145.471, 105.679, 104.105, 103.413, 56.293, 55.882, 45.433, 44.386, 43.962, 41.521, 32.759, 25.050. DUIS-MS calculated for C$_{34}$H$_{44}$N$_{10}$O$_6$ [M+H]$^+$: 689.1, found: 688.8.

Compounds 25 and 26 were Prepared as the Following Procedure

The substituted acetyl chloride and piperazine were dissolved in DMF and K$_2$CO$_3$ with 2 to 1 mole ratio, and the mixture was stirred at room temperature until the reaction was completed. The reaction was quenched with Na$_2$CO$_3$ aqueous solution and stirred overnight, and the precipitated product was collected via filtration and washed with water and dried to give the corresponding compounds.

piperazine-1,4-diylbis((4-methoxyphenyl)methanone) (25)

White solid, 86% yield for the last step; $^1$H-NMR (400 MHz, DMSO-d$_6$) δ 7.403 (4H, d, J=8.4 Hz), 6.994 (4H, d, J=8.4 Hz), 3.799 (6H, s), 3.542 (8H, br). $^{13}$C-NMR (100 MHz, DMSO-d$_6$) δ 169.643, 160.793, 129.640, 127.996, 114.152, 55.746. DUIS-MS calculated for C$_{20}$H$_{22}$N$_2$O$_4$ [M+H]$^+$: 355.1, found: 354.4.

piperazine-1,4-diylbis((4-(methylthio)phenyl)methanone) (26)

White solid, 91% yield for the last step; $^1$H-NMR (400 MHz, DMSO-d$_6$) δ 7.378 (4H, d, J=8.4 Hz), 7.315 (4H, d, J=8.4 Hz), 3.355 (6H, s), 3.533 (8H, br). $^{13}$C-NMR (100 MHz, DMSO-d$_6$) δ 169.394, 141.119, 132.045, 128.339, 125.694, 14.715. DUIS-MS calculated for C$_{20}$H$_{22}$N$_2$O$_2$S$_2$ [M+H]$^+$: 387.1, found: 386.5.

Compounds 29 and 30 were Prepared as the Following Procedure

Doxazosin or compound 24 were dissolved in DMF and K$_2$CO$_3$, and then acetyl chloride was added to the three reactions respectively with 1 to 5 mole ratio to the two compounds. The mixture was stirred until the reaction was completed. The reaction was quenched with Na$_2$CO$_3$ aqueous solution and stirred overnight, and the precipitated product was collected via filtration and washed with water and dried to give the corresponding compounds.

N-(2-(4-(2,3-dihydrobenzo[b][1,4]dioxine-2-carbonyl)piperazin-1-yl)-6,7-dimethoxyquinazolin-4-yl)acetamide (29)

White solid, 36% yield for the last step; $^1$H-NMR (400 MHz, DMSO-d$_6$) δ 10.464 (1H, s), 7.477 (1H, s), 6.874 (5H, m), 5.296 (1H, dd, J=2.4, 6.4 Hz), 4.427 (1H, dd, J=2.4, 11.6 Hz), 4.220 (1H, dd, J=6.8, 12 Hz), 3.899 (3H, s), 3.846 (3H, s), 3.713 (8H, m), 2.411 (3H, s). $^{13}$C-NMR (100 MHz, DMSO-d$_6$) δ 171.532, 165.464, 157.725, 156.160, 151.018, 146.535, 143.432, 121.912, 117.443, 105.629, 103.741, 69.985, 65.205, 56.267, 45.373, 44.592, 43.964, 41.858, 25.802. DUIS-MS calculated for C$_{25}$H$_{27}$N$_5$O$_6$ [M+H]$^+$: 494.1, found: 493.5.

N-(2-(4-(2-(4-(benzyloxy)phenyl)acetyl)piperazin-1-yl)-6,7-dimethoxyquinazolin-4-yl)acetamide (30)

White solid, 29% yield for the last step; $^1$H-NMR (400 MHz, DMSO-d$_6$) δ 10.436 (1H, s), 7.382 (6H, m), 7.181 (2H, d, J=8.4 Hz), 6.958 (2H, d, J=8.4 Hz), 6.897 (1H, s), 5.076 (2H, s), 3.889 (3H, s), 3.838 (3H, s), 3.704 (6H, m), 3.583 (4H, br), 2.394 (3H, s). $^{13}$C-NMR (100 MHz, CDCl$_3$-d$_6$) δ 170.048, 157.680, 156.151, 154.624, 151.293, 147.091, 136.950, 129.637, 128.582, 127.556, 115.237, 105.657, 100.764, 70.084, 56.270, 45.968, 44.102, 41.715, 40.284, 25.679. DUIS-MS calculated for C$_{31}$H$_{33}$N$_5$O$_5$ [M+H]$^+$: 556.2, found: 555.6.

Compounds 31 and 32 were Prepared as the Following Procedure

The dichloro-dimethoxyquinazolin and piperidine or pyrrolidine were dissolved in n-BuOH with 2 to 1 mole ratio, and the mixture was heated to 70° C. for 24 hours, then it was cooled down to room temperature. The precipitated while solid was collected via filtration and washed with n-BuOH to get the corresponding intermediates. After it was dried, the intermediates and piperazine were dissolved in n-BuOH with 1 to 5 mole ratio, respectively. The two reactions were all heated to 100° C. for 24 hours, then it was cooled down to room temperature. The precipitated while solid was collected via filtration and washed with n-BuOH to get two new intermediates, 6,7-dimethoxy-2-(piperazin-1-yl)-4-(piperidin-1-yl)quinazoline, 6,7-dimethoxy-2-(piperazin-1-yl)-4-(pyrrolidin-1-yl)quinazoline. Last, the two intermediates were mixed with 2-(4-(benzyloxy)phenyl)acetyl chloride (1:1 mole ratio) and K$_2$CO$_3$ in DMF, respectively. The reactions were stirred until completed, and were quenched with Na$_2$CO$_3$ aqueous solution and stirred overnight. The precipitated products were collected via filtration and washed with water and dried to give the corresponding compounds 31, 32.

2-(4-(benzyloxy)phenyl)-1-(4-(6,7-dimethoxy-4-(piperidin-1-yl)quinazolin-2-yl)piperazin-1-yl)ethanone (31)

White solid, 56% yield for the last step; $^1$H-NMR (400 MHz, DMSO-d$_6$) δ 7.383 (5H, m), 7.182 (2H, d, J=8.8 Hz), 6.958 (2H, d, J=7.2 Hz), 6.848 (1H, s), 5.077 (2H, s), 3.861 (3H, s), 3.813 (3H, s), 3.561 (15H, m), 1.687 (6H, br). $^{13}$C-NMR (100 MHz, DMSO-d$_6$) δ 169.778, 165.057, 157.608, 154.765, 151.037, 145.215, 137.534, 130.440, 128.408, 115.157, 106.105, 105.426, 104.824, 69.631, 56.021, 55.906, 50.828, 45.820, 44.325, 43.913, 41.647, 25.832, 24.832. DUIS-MS calculated for C$_{34}$H$_{39}$N$_5$O$_4$ [M+H]$^+$: 582.2, found: 581.7.

2-(4-(benzyloxy)phenyl)-1-(4-(6,7-dimethoxy-4-(pyrrolidin-1-yl)quinazolin-2-yl)piperazin-1-yl)ethanone (32)

White solid, 60% yield for the last step; $^1$H-NMR (400 MHz, DMSO-d$_6$) δ 7.382 (6H, m), 7.179 (2H, d, J=8.4 Hz), 6.958 (2H, d, J=8.4 Hz), 6.793 (1H, s), 5.075 (2H, s), 3.815 (10H, m), 3.623 (10H, m), 1.939 (4H, m). $^{13}$C-NMR (100 MHz, DMSO-d$_6$) δ 169.772, 159.752, 157.638, 154.027, 150.966, 144.298, 137.636, 130.425, 128.517, 115.166, 106.435, 105.506, 69.638, 56.086, 55.829, 50.454, 25.716. DUIS-MS calculated for C$_{33}$H$_{37}$N$_5$O$_4$ [M+H]$^+$: 568.2, found: 567.7.

Compound 33 was Prepared as the Following Procedure

A solution of 4-amino-2-chloro-6,7-dimethoxyquinazoline in CH$_2$Cl$_2$ was cooled to −70° C. under argon, and boron tribromide (1:1.2 mole ratio) was added. The mixture was allowed to warm to room temperature over a period of 4 h and was then cooled to −70° C.; methanol was added to quench the reaction, and the solution was concentrated. The solid residue was washed with ethyl acetate to obtain the intermediate 4-amino-2-chloro-6,7-dihydroxyquinazoline. A mixture of the intermediate, ethyl iodine and K$_2$CO$_3$ in DMF was stirred overnight and purified by silica gel chromatography to afford 4-amino-2-chloro-6,7-diethoxyquinazoline. The diethoxyquinazoline and piperazine were dissolved in n-BuOH with 1 to 5 mole ratio, and the mixture was heated to 100° C. for 24 hours, then it was cooled down to room temperature. The precipitated while solid was collected via filtration and washed with n-BuOH. After it was dried, the solid was mixed with 2-(4-(benzyloxy)phenyl)acetyl chloride (1:1 mole ratio) and K$_2$CO$_3$ in DMF. It was stirred until the reaction was completed. The reaction was quenched with Na$_2$CO$_3$ aqueous solution and stirred overnight, and the precipitated product was collected via filtration and washed with water and dried to give compound 33.

1-(4-(4-amino-6,7-diethoxyquinazolin-2-yl)piperazin-1-yl)-2-(4-(benzyloxy)phenyl)ethanone (33)

White solid, 69% yield for the last step; $^1$H-NMR (400 MHz, DMSO-d$_6$) δ 7.383 (6H, m), 7.177 (2H, d, J=8.4 Hz), 7.112 (2H, br), 6.958 (2H, d, J=8.4 Hz), 6.714 (1H, s), 5.075 (2H, s), 4.066 (4H, m), 3.590 (6H, m), 1.369 (6H, m). $^{13}$C-NMR (100 MHz, CDCl$_3$-d$_6$) δ 170.017, 136.987, 129.646, 128.580, 127.739, 115.192, 103.529, 70.075, 65.149, 46.164, 41.904, 40.295, 29.705, 14.666. DUIS-MS calculated for C$_{31}$H$_{31}$N$_5$O$_4$ [M+H]$^+$: 542.2, found: 541.6.

Cell Culture and Antibodies

MDA-MB-231 cells were obtained from ATCC (Rockville, MD). The generation of overexpression EphA2 protein in the cells was reported in our previous study. The cells were maintained in Dulbecco's Modified Eagle Medium (DMEM) supplemented with 10% fetal bovine serum (FBS), 10 mg/ml L-Glutamine, 100 U/mL penicillin-streptomycin, and 0.1 mg/ml streptomycin. EphA2 overexpression cells were grown in the presence of 1 μg/ml puromycin. Cell cultures were grown at 37° C., in a humidified atmosphere of 5% $CO_2$ in a Thermo $CO_2$ incubator (Grand Island, NY).

Antibodies used included rabbit polyclonal antibodies against pEphA/B (synthesized as described previously) and EphA2 (Santa Cruz, Santa Cruz, CA), as well as mouse monoclonal antibody to EphA2 (clone D7, Millipore, Billerica, MA). Secondary antibodies used were goat anti-rabbit conjugated to HRP (Santa Cruz) and donkey anti-mouse conjugated to Alexa Fluor 488 (Thermo Fisher, Grand Island, NY).

EphA2 Activation

MDA-MB-231 EphA2-overexpressing cells were plated in 12-well dishes at a density of 100,000 cells/well and grown for 24 hours prior to stimulation with appropriate compounds and ephrins for 30 min and 10 min, respectively. Compounds were prepared in DMSO at 200 times the final concentrations and 0.5% DMSO was used as vehicle control. Following treatment, cells were washed and lysed in modified RIPA Buffer (20 mM Tris-HCl pH 7.4, 20 mM NaF, 150 mM NaCl, 10% glycerol, 0.1% SDS, 0.5% DCA, 2 mM EDTA, 1% Triton X-100, 2 mM $Na_3VO_4$, and protease inhibitors, including 1 mM phenylmethylsulphonyl fluoride, and 2 μg/ml each of aprotinin and leupeptin) for 20 min, followed by immunoprecipitation. For immunoprecipitation, lysates were combined with 10 μg of ephrin-A1-Fc and 10-15 μl of Gamma-Bind Protein G beads (GE Healthcare Bioscience, Pittsburgh, PA) and rotated for 3 hours at 4° C. 10 μg of human unconjugated Fc was used as a negative control. Beads were pelleted at 9,000 rpm for 2 min at 4° C., and washed twice with 1 ml of IP Wash Buffer (20 mM Tris, pH 7.4, 10% glycerol, 50 mM NaCl, 0.2% Triton X-100, 0.5 mM $Na_3VO_4$, 0.5 mM PMSF). All wash buffer was removed and beads were resuspended in 25 μl of 4× LDS Loading Buffer (Thermo Fisher, Grand Island, NY) with 4 μl of 10× Bolt Sample Reducing Agent (Thermo Fisher), followed by Western Blotting. Samples were boiled 5 min and run on 4-12% Bis-Tris Plus gels (Thermo Fisher), followed by transfer to Immobilon-P PVDF membranes (Millipore, Billerica, MA). Membranes were blocked 1 hr at room temperature in 3% BSA in TBS containing 0.05% Tween-20 (TBS-T) followed by overnight incubation with pEphA/B (1:500) and EphA2 (Santa Cruz) (1:1000) primary antibodies. Membranes were washed in TBS-T and incubated with goat anti-rabbit-HRP (1:5000) secondary antibody 1 hr at room temperature, followed by washing and developing with Luminol Reagent (Santa Cruz). Band intensities were quantified using Quantity One software (Bio-Rad, Hercules, CA).

EphA2 Internalization

MDA-MB-231 cells were plated in 24-well plates on 10 mm square coverslips coated with 10 μg/ml fibronectin and incubated 24-48 hrs before treatment with 50 μM Doxazosin and various doses of compound 27 (0.4, 2, 10, 50 μM) in 0.5% DMSO for 1 hr. As another positive control, cells were treated with 2 μg/ml ephrin-A1-Fc. Cells were then washed with PBS and fixed with 4% paraformaldehyde (Electron Microscopy Sciences, Hatfield, PA) on ice for 10 min, followed by washing and permeabilization with 0.4% NP-40 for 10 min on ice. Non-specific binding sites were blocked with 50 mM $NH_4Cl$ on ice for 10 min, followed by washing with PBS and 0.1% BSA in PBS. Cells were then incubated in primary mouse EphA2 antibody (D7, 1:100) in 0.1% BSA/PBS for 1 hr at room temperature, washed in PBS and BSA/PBS, followed by incubation in secondary donkey anti-mouse Alexa Fluor 488 antibody (1:300) in BSA/PBS for 30 min at room temperature. Cells were washed in PBS and BSA/PBS, followed by mounting in DAPI Mounting Medium (Electron Microscopy Sciences). Images were taken with a Leica microscope.

Clonogenic Assay

MDA-MB-231 cells (1000 cells/well) were seeded in 12-well plates and cultured for 24 h, followed by treatment with various concentrations of the Doxazosin analogs (0, 0.08, 0.4, 2 and 10 μM) in 0.5% DMSO for 14 days. After washing with PBS, colonies were fixed in 4% paraformaldehyde in PBS, washed in 20% methanol, and stained with 0.5% crystal violet.

Docking Investigation

Docking studies were done to gain insight into the possible mode of interaction between the compounds and EphA2. The structures were drawn with Marvin Sketch (www.ChemAxon.com) and energy minimized in MOE 2010 (www.chemcomp.com) using the MMFF94s force field. The database of compounds was then used for the docking studies. The protein crystal structure of 3FL7.pdb was prepared for docking by adjusting the pH of the system to a pH of 7.4. The binding site in EphA2 was delineated by Doxazosin. After docking, only the top docked pose of each compound was retained for analysis.

Adrenoceptor Binding Activity

Analysis of Doxazosin and analog binding to rat α1a adrenergic receptor was performed by Eurofins Panlabs Taiwan, Ltd. (Taiwan). [$^3$H]-prazosin at 0.25 nM was used as the radioligand. Compounds 24, 27, and Doxazosin at 5 different doses ranging from 0.08 nM-3 μM in 0.1% DMSO were incubated with [$^3$H]-prazosin in a final volume of 1 ml of assay buffer (50 mM Tris-HCl, pH 7.4, 0.5 mM EDTA) for 1 h at 25° C. Non-specific binding was defined by use of 10 μM phentolamine. Incubations were terminated by vacuum filtration over 0.1% PEI pretreated glass fiber filters and filters were washed for 10 s with ice cold 0.1M NaCl and radioactivity retained on the filters was determined by liquid scintillation spectrometry. $IC_{50}$ values were determined by a non-linear regression analysis using GraphPad Prism v.5 (GraphPad).

Having described the invention, the following is claimed:

1. A pharmaceutical composition comprising:
a compound having the formula:

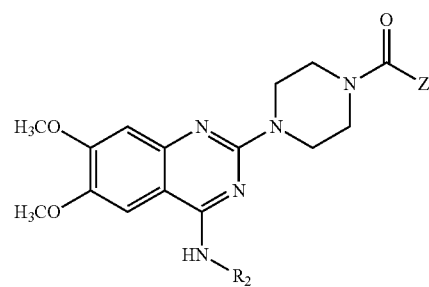

wherein $R^2$ is selected from H, an alkoxy or a $C_{1-6}$ alkyl group,

Z is selected from the group consisting of
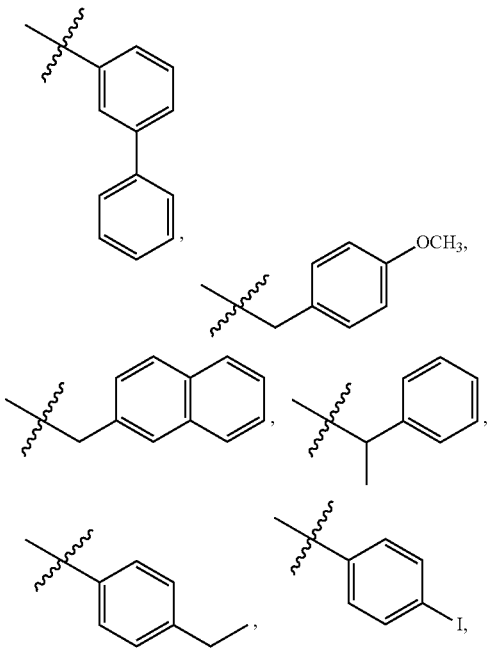
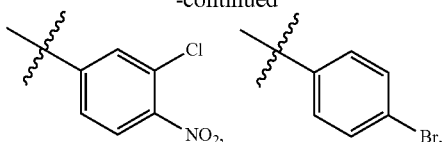
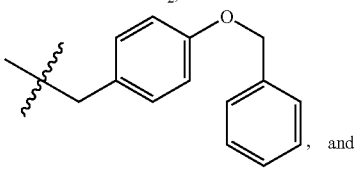
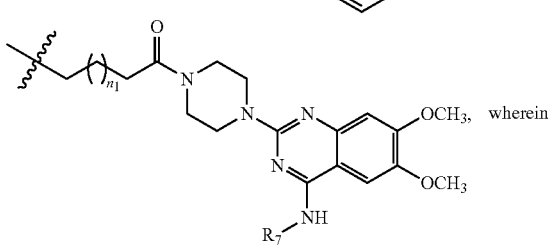
$R^7$ is selected from H, an alkoxy or a $C_{1-6}$ alkyl group, and $n_1$ is an integer from 1-20, and pharmaceutically acceptable salts thereof; and
a pharmaceutically acceptable carrier.
2. The pharmaceutical composition of claim 1, the compound selected from the group consisting of:
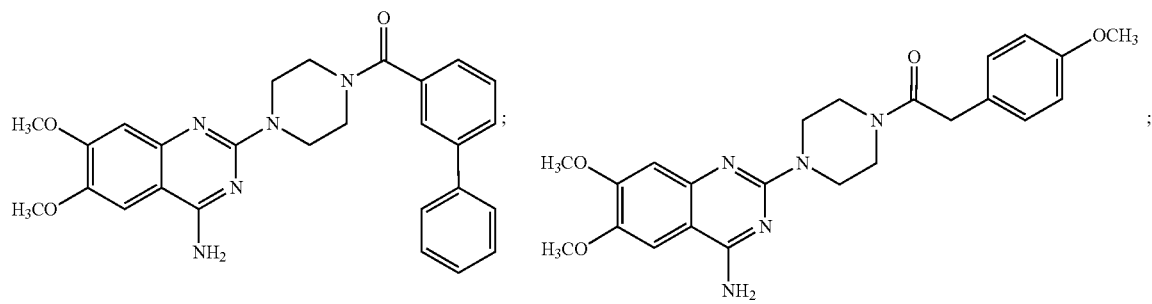
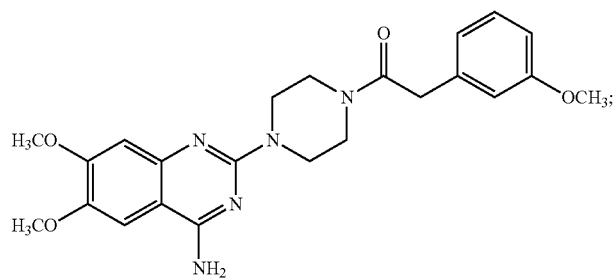
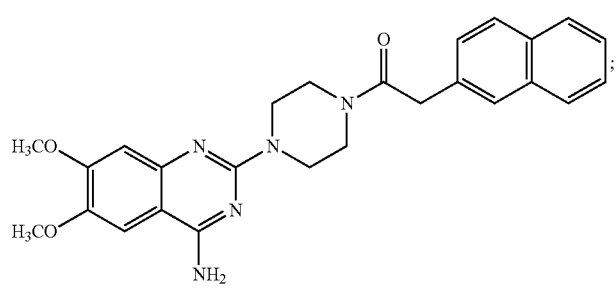
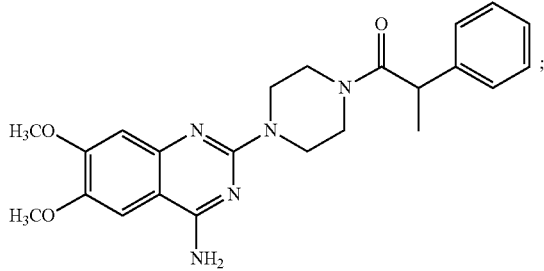

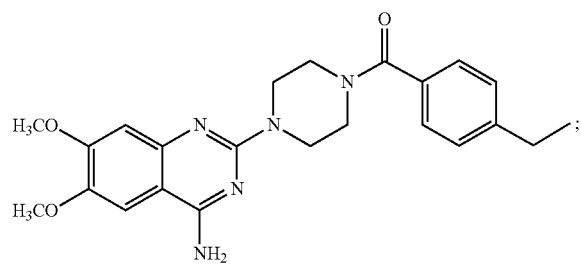
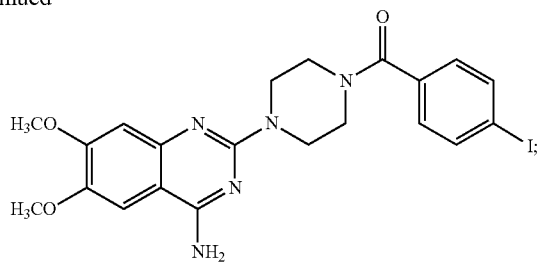
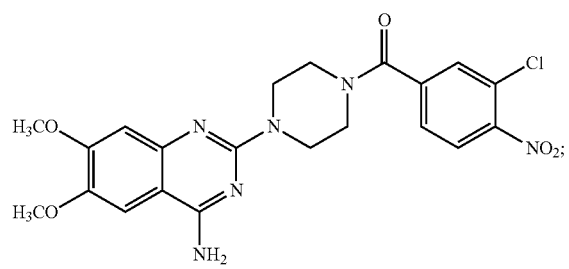
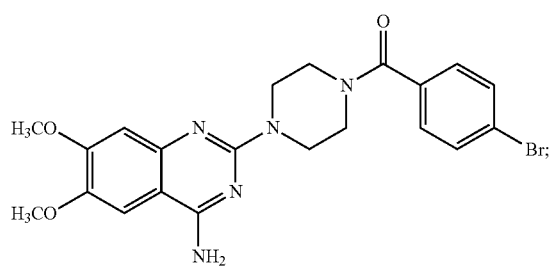
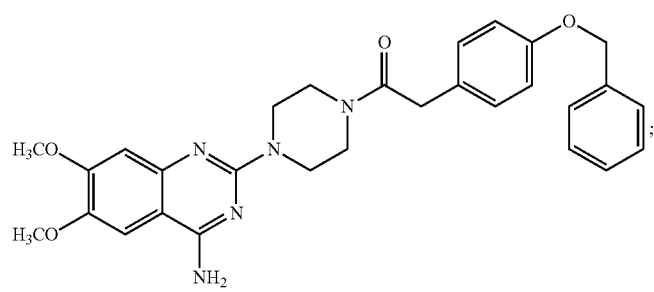
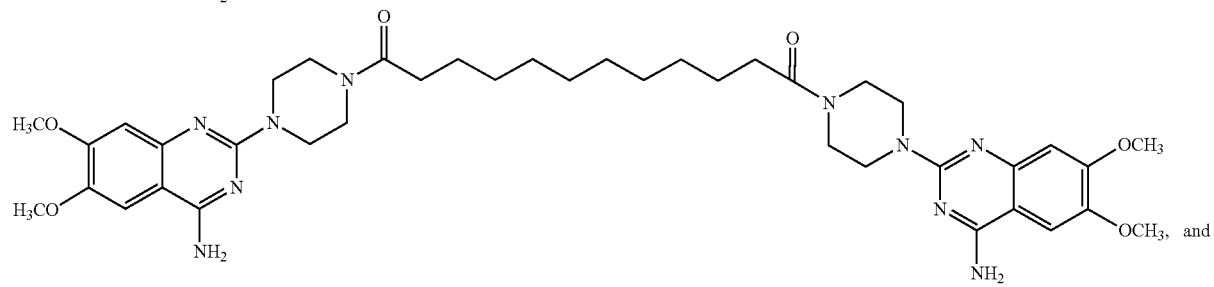
pharmaceutically acceptable salts thereof.
3. The pharmaceutical composition of claim 2, the compound having the formula:
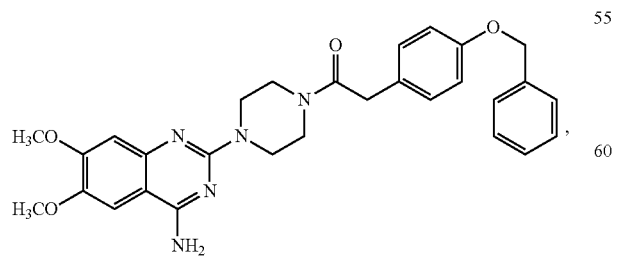
or a pharmaceutically acceptable salt thereof.

4. The pharmaceutical composition of claim 2, the compound having the formula:
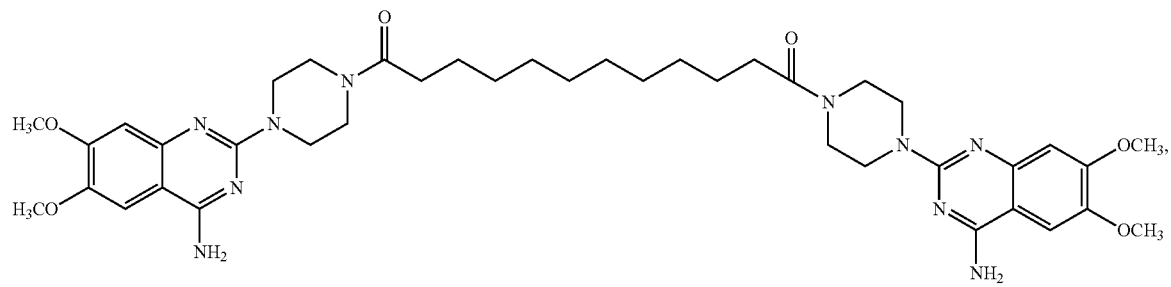 [SMILES: COc1cc2nc(N3CCN(C(=O)CCCCCCCCCCC(=O)N4CCN(c5nc(N)c6cc(OC)c(OC)cc6n5)CC4)CC3)nc(N)c2cc1OC]
or a pharmaceutically acceptable salt thereof.
5. The pharmaceutical composition of claim 1, the compound selected from the group consisting of:
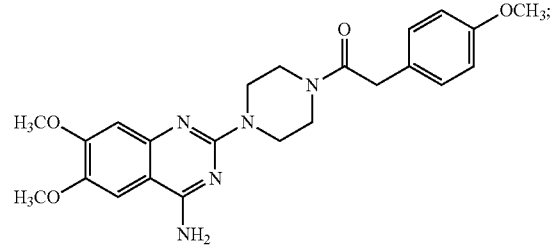
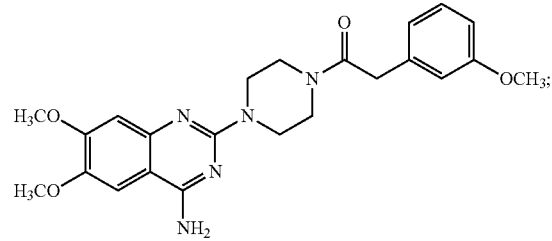
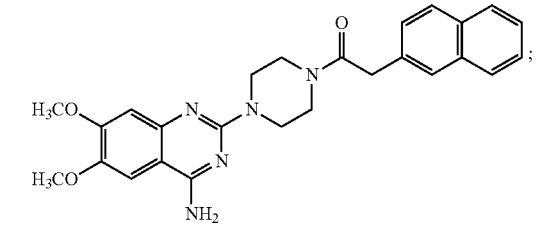
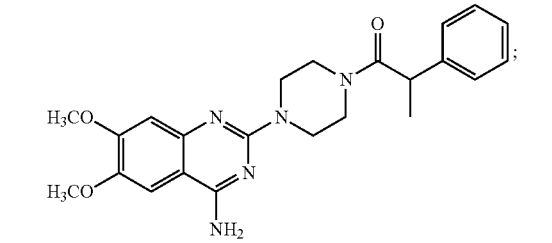
-continued
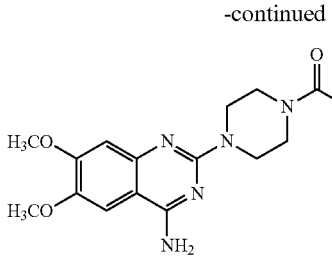
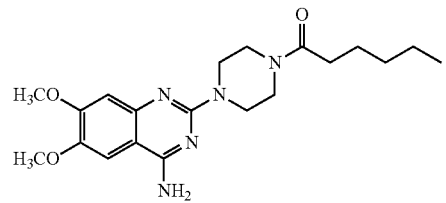
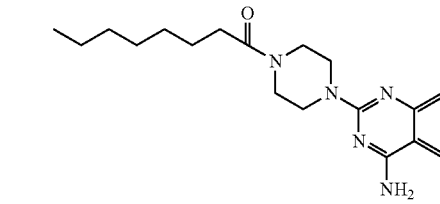
and pharmaceutically acceptable salts thereof.

6. The pharmaceutical composition of claim 1, the compound selected from the group consisting of:
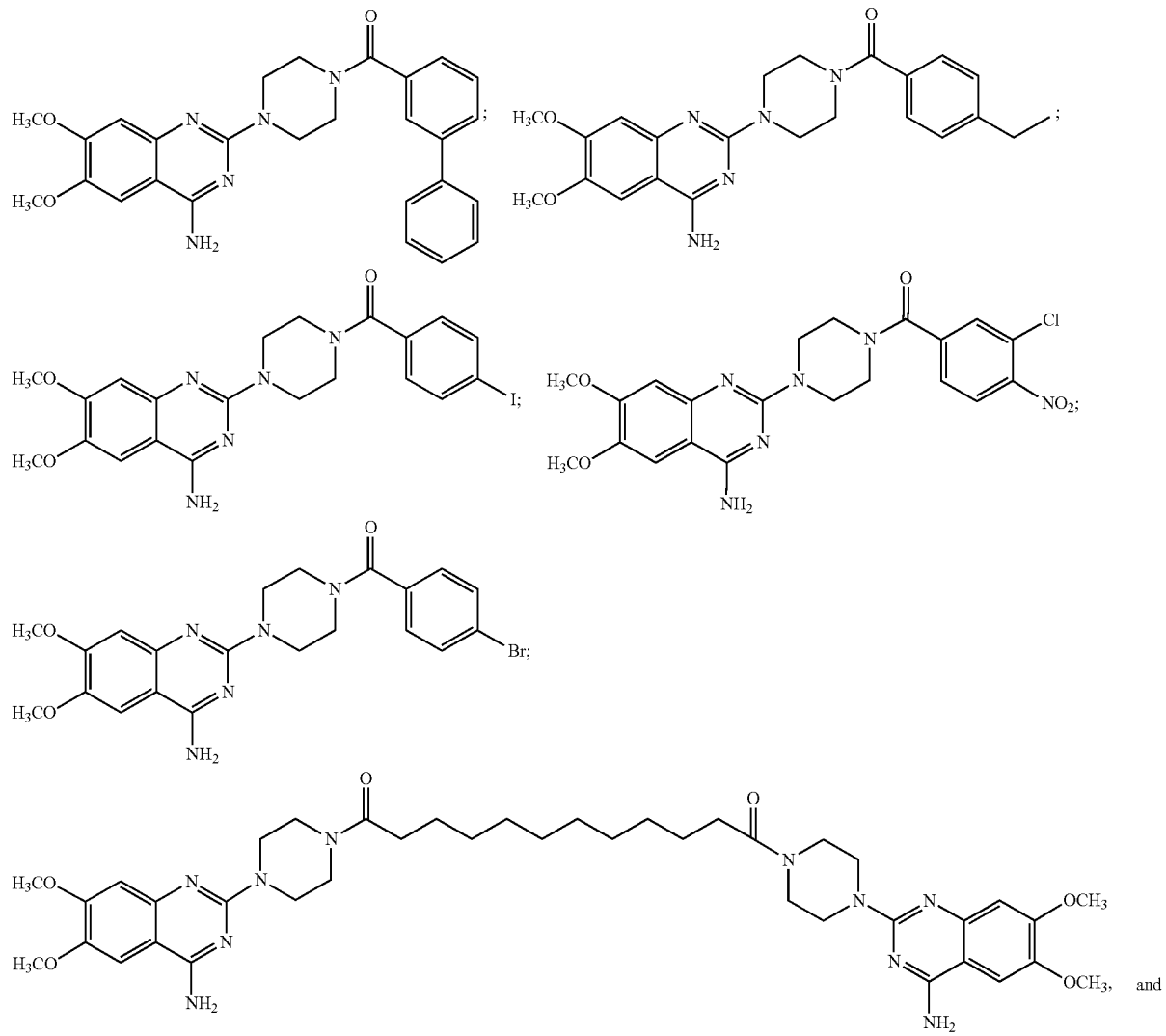
pharmaceutically acceptable salts thereof.
* * * * *